(12) United States Patent
Ventura et al.

(10) Patent No.: US 7,993,350 B2
(45) Date of Patent: *Aug. 9, 2011

(54) SHAPEABLE OR STEERABLE GUIDE SHEATHS AND METHODS FOR MAKING AND USING THEM

(75) Inventors: Christine P. Ventura, San Jose, CA (US); Alfonso N. Pulido, Palo Alto, CA (US); Stephen A. Leeflang, Sunnyvale, CA (US); Christian S. Eversull, Palo Alto, CA (US)

(73) Assignee: Medtronic, Inc., Minneapolis, MN (US)

( * ) Notice: Subject to any disclaimer, the term of this patent is extended or adjusted under 35 U.S.C. 154(b) by 1026 days.

This patent is subject to a terminal disclaimer.

(21) Appl. No.: 11/746,639

(22) Filed: May 9, 2007

(65) Prior Publication Data

US 2008/0015625 A1    Jan. 17, 2008

Related U.S. Application Data

(60) Provisional application No. 60/798,915, filed on May 9, 2006.

(51) Int. Cl.
*A61F 11/00* (2006.01)
(52) U.S. Cl. ...................................................... 606/108
(58) Field of Classification Search .................. 606/108, 606/198; 600/585
See application file for complete search history.

(56) References Cited

U.S. PATENT DOCUMENTS

| | | | |
|---|---|---|---|
| 1,060,665 A | 5/1913 | Bell | |
| 2,574,840 A | 11/1951 | Pieri et al. | |
| 2,688,329 A | 9/1954 | Wallace | |
| 3,162,190 A | 12/1964 | Gizzo | |
| 3,452,740 A | 7/1969 | Muller | |
| 3,974,834 A | 8/1976 | Kane | |
| 4,033,331 A | 7/1977 | Guss et al. | |
| 4,224,929 A | 9/1980 | Furihata | |
| 4,392,853 A | 7/1983 | Muto | |
| 4,401,433 A | 8/1983 | Luther | |
| 4,406,656 A | 9/1983 | Hattler et al. | |

(Continued)

FOREIGN PATENT DOCUMENTS

EP    0283661 A2    9/1988

(Continued)

OTHER PUBLICATIONS

PCT International Search Report for PCT/US2004/032374, Applicant: Acumen medical, Inc., Form PCT/ISA/210, dated May 13, 2005 (4 pages).

(Continued)

*Primary Examiner* — Gary Jackson
*Assistant Examiner* — Eric Blatt

(57) ABSTRACT

Apparatus and methods are provided for providing access to a body lumen, e.g., to deliver a pacing lead within a patient's heart. The apparatus includes a tubular member including a proximal end, a distal end sized for insertion into a body lumen, and a lumen extending therebetween. An elongate member extends from the distal end of the tubular member. An expandable sheath extends along at least a portion of the elongate member, the sheath being expandable from a contracted condition to facilitate insertion into a body lumen, and an enlarged condition wherein the sheath at least partially defines a lumen communicating with the tubular member lumen. A stylet or other shaped element is insertable into the elongate member for changing a shape of at least a distal tip of the elongate member, e.g., for accessing side branches extending from a body lumen, e.g., within a patient's coronary venous system.

13 Claims, 38 Drawing Sheets

U.S. PATENT DOCUMENTS

| | | |
|---|---|---|
| 4,451,256 A | 5/1984 | Weikl et al. |
| 4,470,407 A | 9/1984 | Hussein |
| 4,569,347 A | 2/1986 | Frisbie |
| 4,581,017 A | 4/1986 | Sahota |
| 4,601,713 A | 7/1986 | Fuqua |
| 4,619,247 A | 10/1986 | Inoue et al. |
| 4,650,472 A | 3/1987 | Bates |
| 4,689,041 A | 8/1987 | Corday et al. |
| 4,710,181 A | 12/1987 | Fuqua |
| 4,715,545 A | 12/1987 | Hanifl |
| 4,717,387 A | 1/1988 | Inoue et al. |
| 4,723,936 A | 2/1988 | Buchbinder |
| 4,738,666 A | 4/1988 | Fuqua |
| 4,774,949 A | 10/1988 | Fogarty |
| 4,779,611 A | 10/1988 | Grotters et al. |
| 4,781,681 A | 11/1988 | Sharrow et al. |
| 4,784,113 A | 11/1988 | Mackin |
| 4,798,193 A | 1/1989 | Giesy |
| 4,886,067 A | 12/1989 | Palermo |
| 4,898,577 A | 2/1990 | Badger et al. |
| 4,921,479 A | 5/1990 | Grayzel |
| 4,960,411 A | 10/1990 | Buchbinder |
| 4,961,738 A | 10/1990 | Mackin |
| 4,976,710 A | 12/1990 | Mackin |
| 4,995,878 A | 2/1991 | Rai |
| 5,015,239 A | 5/1991 | Browne |
| 5,029,574 A | 7/1991 | Shimamura et al. |
| 5,060,660 A | 10/1991 | Gambale et al. |
| 5,090,959 A | 2/1992 | Samson et al. |
| 5,114,414 A | 5/1992 | Buchbinder |
| 5,116,317 A | 5/1992 | Carson, Jr. et al. |
| 5,125,895 A | 6/1992 | Buchbinder et al. |
| 5,137,519 A | 8/1992 | Littrell et al. |
| 5,147,317 A | 9/1992 | Shank |
| 5,160,559 A | 11/1992 | Scovil |
| 5,176,660 A | 1/1993 | Truckai |
| 5,188,596 A | 2/1993 | Condon et al. |
| 5,201,756 A | 4/1993 | Horzewski et al. |
| 5,203,772 A | 4/1993 | Hammerslag et al. |
| 5,209,728 A | 5/1993 | Kraus |
| 5,234,425 A | 8/1993 | Fogarty et al. |
| 5,246,420 A | 9/1993 | Kraus et al. |
| 5,254,084 A | 10/1993 | Geary et al. |
| 5,254,088 A | 10/1993 | Lundquist et al. |
| 5,256,150 A | 10/1993 | Quiachon et al. |
| 5,263,932 A | 11/1993 | Jang |
| 5,267,958 A | 12/1993 | Buchbinder |
| 5,271,383 A | 12/1993 | Wilk |
| 5,273,535 A | 12/1993 | Edwards et al. |
| 5,275,151 A | 1/1994 | Shockey et al. |
| 5,304,134 A | 4/1994 | Kraus et al. |
| 5,318,525 A | 6/1994 | West et al. |
| 5,345,937 A | 9/1994 | Middleman et al. |
| 5,346,504 A | 9/1994 | Ortiz et al. |
| 5,358,478 A | 10/1994 | Thompson et al. |
| 5,358,479 A | 10/1994 | Wilson |
| 5,389,073 A | 2/1995 | Imran |
| 5,391,147 A | 2/1995 | Imran et al. |
| 5,395,349 A | 3/1995 | Quiachon et al. |
| 5,409,469 A | 4/1995 | Schaerf |
| 5,409,483 A | 4/1995 | Campbell et al. |
| 5,413,560 A | 5/1995 | Solar |
| 5,431,676 A | 7/1995 | Dubrul et al. |
| 5,447,497 A | 9/1995 | Sogard et al. |
| 5,468,225 A | 11/1995 | Teirstein |
| 5,472,418 A | 12/1995 | Palestrant |
| 5,489,270 A | 2/1996 | Van Erp |
| 5,498,329 A | 3/1996 | Galel et al. |
| 5,505,686 A | 4/1996 | Willis |
| 5,549,556 A | 8/1996 | Ndondo-Lay |
| 5,573,517 A | 11/1996 | Bonutti et al. |
| 5,593,405 A | 1/1997 | Osypka |
| 5,599,305 A | 2/1997 | Hermann |
| 5,611,777 A | 3/1997 | Bowden et al. |
| 5,618,267 A | 4/1997 | Palestrant |
| 5,669,924 A | 9/1997 | Shaknovich |
| 5,674,240 A | 10/1997 | Bonutti et al. |
| 5,713,853 A | 2/1998 | Clark |
| 5,713,867 A | 2/1998 | Morris |
| 5,735,831 A | 4/1998 | Clark |
| 5,738,649 A | 4/1998 | Macoviak |
| 5,741,320 A | 4/1998 | Thornton et al. |
| 5,749,889 A | 5/1998 | Bacich |
| 5,749,890 A | 5/1998 | Shaknovich |
| 5,752,518 A | 5/1998 | McGee et al. |
| 5,752,934 A | 5/1998 | Campbell |
| 5,762,604 A | 6/1998 | Kieturakis |
| 5,772,628 A | 6/1998 | Bacich |
| 5,795,331 A | 8/1998 | Cragg |
| 5,810,776 A | 9/1998 | Bacich |
| 5,824,041 A | 10/1998 | Lenker |
| 5,827,227 A | 10/1998 | DeLago |
| 5,857,760 A | 1/1999 | Pelton |
| 5,863,366 A | 1/1999 | Snow |
| 5,876,373 A | 3/1999 | Giba et al. |
| 5,876,426 A | 3/1999 | Kume et al. |
| 5,904,670 A | 5/1999 | Schreiner |
| 5,908,435 A | 6/1999 | Samuels |
| 5,910,154 A | 6/1999 | Tsugita |
| 5,911,702 A | 6/1999 | Romley |
| 5,935,102 A | 8/1999 | Bowden et al. |
| 5,935,122 A | 8/1999 | Fourkas |
| 5,944,691 A | 8/1999 | Querns et al. |
| 5,961,499 A | 10/1999 | Bonutti et al. |
| 5,972,441 A | 10/1999 | Campbell |
| 5,997,508 A | 12/1999 | Lunn et al. |
| 6,007,517 A | 12/1999 | Anderson |
| 6,007,522 A | 12/1999 | Agro |
| 6,035,224 A | 3/2000 | West |
| 6,048,332 A | 4/2000 | Duffy |
| 6,068,610 A | 5/2000 | Ellis |
| 6,068,623 A | 5/2000 | Zadno-Azizi |
| 6,086,557 A | 7/2000 | Morejohn et al. |
| 6,090,072 A | 7/2000 | Kratoska et al. |
| 6,099,498 A | 8/2000 | Addis |
| 6,110,145 A | 8/2000 | Macoviak |
| 6,120,477 A | 9/2000 | Campbell et al. |
| 6,122,552 A | 9/2000 | Tockman |
| 6,178,346 B1 | 1/2001 | Amundson et al. |
| 6,179,827 B1 | 1/2001 | Davis |
| 6,183,443 B1 | 2/2001 | Kratoska et al. |
| 6,197,016 B1 | 3/2001 | Fourkas et al. |
| 6,210,407 B1 | 4/2001 | Webster |
| 6,283,951 B1 | 9/2001 | Flaherty et al. |
| 6,296,616 B1 | 10/2001 | McMahan |
| 6,312,406 B1 | 11/2001 | Jayaraman |
| 6,338,730 B1 | 1/2002 | Bonutti et al. |
| 6,361,528 B1 | 3/2002 | Wilson et al. |
| 6,458,107 B1 | 10/2002 | Ockuly |
| 6,494,860 B2 | 12/2002 | Rocamora |
| 6,562,049 B1 | 5/2003 | Norlander et al. |
| 6,579,278 B1 | 6/2003 | Bencini |
| 6,585,718 B2 | 7/2003 | Hayzelden et al. |
| 6,592,581 B2 | 7/2003 | Bowe |
| 6,596,020 B2 | 7/2003 | Vardi |
| 6,602,241 B2 | 8/2003 | Makower |
| 6,610,007 B2 | 8/2003 | Belson et al. |
| 6,616,628 B2 | 9/2003 | Hayzelden |
| 6,638,268 B2 | 10/2003 | Niazi |
| 6,652,492 B1 | 11/2003 | Bell et al. |
| 6,730,058 B2 | 5/2004 | Hayzelden |
| 6,743,196 B2 | 6/2004 | Barbut |
| 6,743,227 B2 | 6/2004 | Seraj et al. |
| 6,755,812 B2 | 6/2004 | Peterson et al. |
| 6,783,510 B1 | 8/2004 | Gibson et al. |
| 6,800,056 B2 | 10/2004 | Tartaglia et al. |
| 6,814,715 B2 | 11/2004 | Bonutti et al. |
| 6,979,290 B2 | 12/2005 | Mourlas et al. |
| 6,984,232 B2 | 1/2006 | Vanney et al. |
| 6,997,939 B2 | 2/2006 | Linder |
| 7,004,173 B2 | 2/2006 | Sparks |
| 7,399,307 B2 | 7/2008 | Evans |
| 2001/0007927 A1 | 7/2001 | Koblish et al. |
| 2001/0039418 A1 | 11/2001 | Schaer |
| 2001/0041909 A1 | 11/2001 | Tsugita |
| 2001/0053919 A1 | 12/2001 | Kieturakis et al. |
| 2002/0095117 A1 | 7/2002 | Wilson et al. |

| | | | |
|---|---|---|---|
| 2002/0099431 | A1 | 7/2002 | Armstrong et al. |
| 2002/0123765 | A1 | 9/2002 | Sepetka |
| 2002/0165598 | A1 | 11/2002 | Wahr et al. |
| 2003/0004540 | A1 | 1/2003 | Linder |
| 2003/0065353 | A1 | 4/2003 | Horzewski et al. |
| 2003/0092995 | A1 | 5/2003 | Thompson |
| 2003/0233115 | A1 | 12/2003 | Eversull et al. |
| 2004/0005295 | A1 | 1/2004 | Lee |
| 2004/0006344 | A1 | 1/2004 | Nguyen et al. |
| 2004/0054724 | A1 | 3/2004 | Sudo |
| 2004/0059257 | A1 | 3/2004 | Gaber |
| 2004/0073286 | A1 | 4/2004 | Armstrong et al. |
| 2004/0087968 | A1 | 5/2004 | Core |
| 2004/0097788 | A1 | 5/2004 | Mourlas et al. |
| 2004/0167439 | A1 | 8/2004 | Sharrow |
| 2005/0008584 | A1 | 1/2005 | Montgomery |
| 2005/0027243 | A1 | 2/2005 | Gibson et al. |
| 2005/0085842 | A1 | 4/2005 | Eversull et al. |
| 2005/0149104 | A1 | 7/2005 | Leeflang |
| 2005/0149105 | A1 | 7/2005 | Leeflang et al. |
| 2005/0197623 | A1 | 9/2005 | Leeflang |
| 2005/0228452 | A1 | 10/2005 | Mourlas et al. |
| 2006/0217755 | A1 | 9/2006 | Eversull |

FOREIGN PATENT DOCUMENTS

| | | |
|---|---|---|
| EP | 0842673 A1 | 5/1998 |
| EP | 818214 | 4/2007 |
| WO | 84/01512 | 4/1984 |
| WO | 97/29680 | 8/1997 |
| WO | 9740880 A1 | 11/1997 |
| WO | 98/29026 | 7/1998 |
| WO | 0024310 A1 | 5/2000 |
| WO | 0032264 | 6/2000 |
| WO | 0103766 | 1/2001 |
| WO | 0149356 A1 | 7/2001 |
| WO | 0172368 A2 | 10/2001 |
| WO | 0230310 | 4/2002 |
| WO | 03037416 | 5/2003 |
| WO | 03039350 A2 | 5/2003 |
| WO | 03053491 A2 | 7/2003 |
| WO | 03090834 | 11/2003 |

OTHER PUBLICATIONS

PCT Written Opinion of the International Search Authority for PCT/US2004/032374, Applicant: Acumen medical, Inc., Form PCT/ISA/237, dated May 13, 2005 (8 pages).
European Search Report for European Patent Application No. 09156041.7-2319, Applicant: The Board of Trustees of The Leland Stanford Junior University, EPO Forms 1507N, 1503, P0459, 1143 and EPA Form 2906, dated May 8, 2009 (9 pages).
USPTO Office Action for co-pending U.S. Appl. No. 10/423,321 dated Oct. 24, 2006.
USPTO Office Action for co-pending U.S. Appl. No. 10/934,082 dated Feb. 8, 2007.
USPTO Office Action for co-pending U.S. Appl. No. 10/958,034 dated Oct. 19, 2006.
USPTO Office Action for co-pending U.S. Appl. No. 10/958,034 dated Dec. 13, 2006.
USPTO Office Action for co-pending U.S. Appl. No. 11/062,074 dated Nov. 1, 2006.
USPTO Office Action for co-pending U.S. Appl. No. 11/062,074 dated Feb. 26, 2007.
USPTO Office Action for co-pending U.S. Appl. No. 11/347,361 dated Dec. 13, 2006.
USPTO Notice of Allowability for U.S. Appl. No. 10/423,321, dated Mar. 12, 2010.
Amendment and Response to Office Action in U.S. Appl. No. 10/423,321, dated Dec. 14, 2009.
USPTO Office Action for U.S. Appl. No. 10/423,321, dated Aug. 12, 2009.
USPTO Decision on Granting Petition Under 37 CFR 1.313(c)(12) for U.S. Appl. No. 10/423,321, dated Jun. 17, 2009.
Petition to Withdrawn from Issue and Consideration of RCE Under 37 CFR 1.313(c)(2) for U.S. Appl. No. 10/423,321, dated Jun. 16, 2009.
USPTO Office Action for U.S. Appl. No. 10/423,321, dated Jun. 2, 2009.
Appeal Brief Under 37 CFR 41.37 for U.S. Appl. No. 10/423,321, dated Apr. 21, 2008.
Halliday et al., Fundamentals of Physics, vol. 1, Fourth Ed. pp. 132-133, dated Dec. 1991.
USPTO Office Action for U.S. Appl. No. 10/423,321, dated Nov. 21, 2007.
Arguments in Support of Pre-Appeal Request for Review for U.S. Appl. No. 10/423,321, dated Sep. 24, 2007.
USPTO Office Action for U.S. Appl. No. 10/423,321, dated Aug. 16, 2007.
USPTO Office Action for U.S. Appl. No. 10/423,321, dated Aug. 6, 2007.
Amendment After Final for U.S. Appl. No. 10/423,321, dated Jul. 24, 2007.
USPTO Office Action for U.S. Appl. No. 10/432,231, dated May 24, 2007.
Amendment and Response to Office Action for U.S. Appl. No. 10/423,321, dated Mar. 26, 2007.
USPTO Office Action for U.S. Appl. No. 10/423,321, dated Oct. 24, 2006.
Amendment and Response to Office Action/Restriction for U.S. Appl. No. 10/423,321, dated Aug. 28, 2006.
USPTO Office Action for U.S. Appl. No. 10/423,321, dated Jun. 28, 2006.
USPTO Notice of Allowability for U.S. Appl. No. 10/934,082, dated Jul. 6, 2009.
Amendment for U.S. Appl. No. 10/934,082, dated Apr. 28, 2009.
USPTO Office Action for U.S. Appl. No. 10/934,082, dated Apr. 2, 2009.
Amendment for U.S. Appl. No. 10/934,082, dated Mar. 23, 2009.
USPTO Office Action for U.S. Appl. No. 10/934,082, dated Mar. 10, 2009.
Amendment for U.S. Appl. No. 10/934,082, dated Dec. 29, 2008.
USPTO Office Action for U.S. Appl. No. 10/934,082, dated Nov. 12, 2008.
USPTO Office Action for U.S. Appl. No. 10/934,082, dated Jul. 2, 2008.
Amendment for U.S. Appl. No. 10/934,082, dated Jun. 16, 2008.
USPTO Office Action for U.S. Appl. No. 10/934,082, dated Mar. 14, 2008.
Amendment and Response to Office Action for U.S. Appl. No. 10/934,082, dated Nov. 5, 2007.
USPTO Office Action for U.S. Appl. No. 10/934,082, dated Jun. 4, 2007.
Response to Office Action/Restriction for U.S. Appl. No. 10/934,082, dated Mar. 7, 2007.
USPTO Office Action for U.S. Appl. No. 10/934,082, dated Feb. 8, 2007.
Vadimovich, G. et al.: A Method of Endoscopic Investigation of Vascular Structures Directly Through Flowing Blood; The Heart Surgery Forum #1999-93916 2(2):136-38, May 8, 1999, Forum Multimedia Publishing, LLC.
Response to Office Action in U.S. Appl. No. 10/958,034, dated Nov. 9, 2009.
Advisory Action in U.S. Appl. No. 10/958,034, dated Sep. 25, 2009.
USPTO Office Action for U.S. Appl. No. 10/958,034, dated Apr. 14, 2009.
Response to Office Action in U.S. Appl. No. 10/958,034, dated May 8, 2009.
USPTO Office Action for U.S. Appl. No. 10/958,034, dated Aug. 10, 2009.
Response to Office Action in U.S. Appl. No. 10/958,034, dated Sep. 16, 2009.
Amendment and Response to Office Action in U.S. Appl. No. 10/958,034, dated Feb. 3, 2009.
USPTO Office Action for U.S. Appl. No. 10/958,034, dated Dec. 11, 2008.
Amendment and Response to Office Action in U.S. Appl. No. 10/958,034, dated Jul. 25, 2008.
USPTO Office Action for U.S. Appl. No. 10/958,034, dated Apr. 4, 2008.

USPTO Office Action for U.S. Appl. No. 10/958,034, dated Oct. 10, 2007.
Amendment in U.S. Appl. No. 10/958,034, dated Sep. 27, 2007.
USPTO Office Action for U.S. Appl. No. 10/958,034, dated Aug. 14, 2007.
USPTO Office Action for U.S. Appl. No. 10/958,034, dated Jul. 27, 2007.
Amendment and Response to Office Action in U.S. Appl. No. 10/958,034, dated May 7, 2007.
Amendment and Response to Office Action in U.S. Appl. No. 10/958,034, dated Nov. 20, 2006.
USPTO Notice of Allowability and Examiner's Amendment for U.S. Appl. No. 10/958,034, dated Jan. 14, 2010.
Response to Non-Final Office Action in U.S. Appl. No. 11/062,074, dated Jun. 22, 2010.
USPTO Office Action for U.S. Appl. No. 11/062,074, dated Jan. 22, 2010.
Arguments in Support of Pre-appeal Request for Review in U.S. Appl. No. 11/062,074, dated Sep. 28, 2009.
USTPO Office Action for U.S. Appl. No. 11/062,074, dated Apr. 28, 2009.
USPTO Office Action for U.S. Appl. No. 11/062,074, dated Feb. 10, 2009.
Arguments in Support of Pre-Appeal Request for Review for U.S. Appl. No. 11/062,074, dated Nov. 20, 2008.
USPTO Office Action for U.S. Appl. No. 11/062,074, dated Aug. 20, 2008.
Response to Office Action for U.S. Appl. No. 11/062,074, dated May 23, 2008.
USPTO Office Action for U.S. Appl. No. 11/062,074, dated Jan. 23, 2008.
Amendment and Response to Office Action/Restriction for U.S. Appl. No. 11/062,074, dated Oct. 8, 2007.
USPTO Office Action for U.S. Appl. No. 11/062,074, dated Sep. 6, 2007.
Amendment and Response to Office Action/Restriction in U.S. Appl. No. 11/062,074, dated Nov. 30, 2006.
USPTO Office Action for U.S. Appl. No. 11/062,074, dated Nov. 4, 2010.
USPTO Office Action for U.S. Appl. No. 11/347,361, dated Oct. 27, 2009.
USPTO Office Action for U.S. Appl. No. 11/347,361, dated Apr. 29, 2009.
USPTO Office Action for U.S. Appl. No. 11/347,361, dated Nov. 26, 2008.
USPTO Office Action for U.S. Appl. No. 11/347,361, dated Apr. 3, 2008.
USPTO Office Action for U.S. Appl. No. 11/347,361, dated Oct. 17, 2007.
USPTO Office Action for U.S. Appl. No. 11/347,361, dated Aug. 14, 2007.
USPTO Office Action for U.S. Appl. No. 11/347,361, dated Jul. 27, 2007.
Amendment and Response for U.S. Appl. No. 11/347,361, dated Jan. 16, 2010.
Amendment and Response for U.S. Appl. No. 11/347,361, dated Dec. 14, 2009.
Amendment and Response for U.S. Appl. No. 11/347,361, dated Jun. 22, 2009.
Amendment and Response for U.S. Appl. No. 11/347,361, dated Jan. 12, 2009.
Amendment and Response for U.S. Appl. No. 11/347,361, dated Jul. 3, 2008.
Amendment After Final for U.S. Appl. No. 11/347,361, dated Oct. 29, 2007.
Amendment After Final for U.S. Appl. No. 11/347,361, dated Sep. 27, 2007.
Amendment and Response to Office Action for U.S. Appl. No. 11/347,361, dated May 7, 2007.
USPTO Office Action for U.S. Appl. No. 11/347,361, dated Jan. 11, 2010.
Moser, Shure, Harrell & Tulumello: Angioscopic visualization of Polumonary Emboli; Chest, 772:2, Feb. 1980.
Kuo & Koch; In vivo angioscopic visualization of right heart structure in dogs by means of a balloon-tipped fiberoptic endoscope: Potential role in percutaneous ablative procedures; American Heart Journal, Jan. 1994; 127:187-97; Mosby-Year Boock, Inc.
Fujimura, O. et al: Direct in vivo visualization of right cardiac anatomy by fibreoptic endoscopy; observation of radiofrequency-induced acute lesions around the ostium of the coronary sinus; European Heart Journal (1994) 15; 534-40; European Society of Cardio.
Fujimura O. et al.: Direct In Vivo Visualization of Right Cardiac Anatomy by Fibreoptic Endoscopy Hemodynamic Effects and Image Validation; Angiology: The Journal of Vascular Diseases; Mar. 1995; vol. 46, No. 3, pp. 201-209; Westminster Publications, Inc.

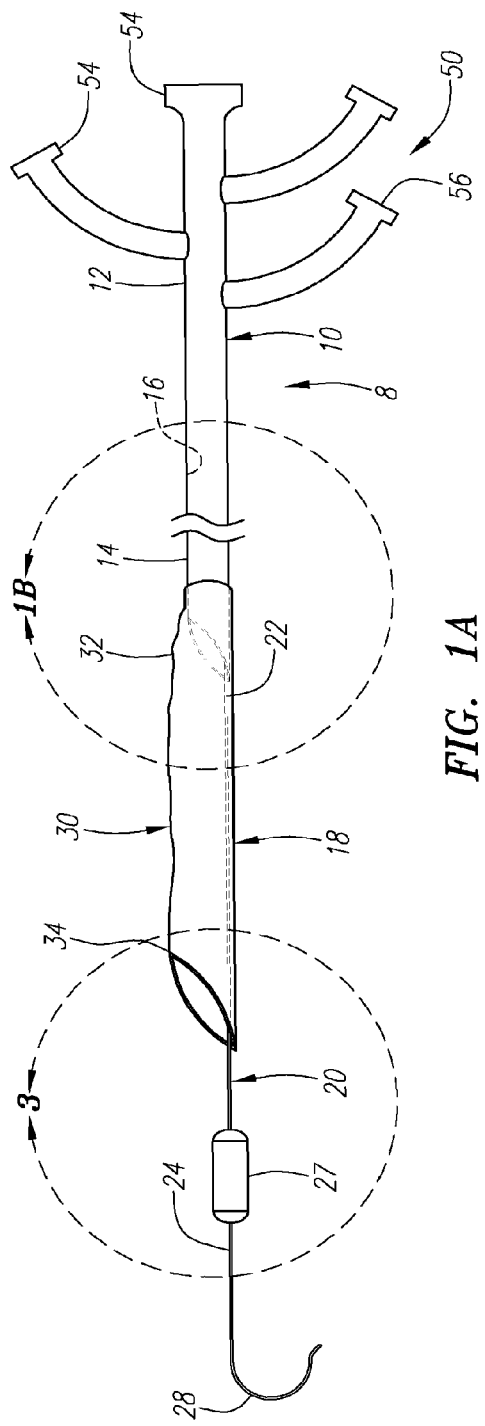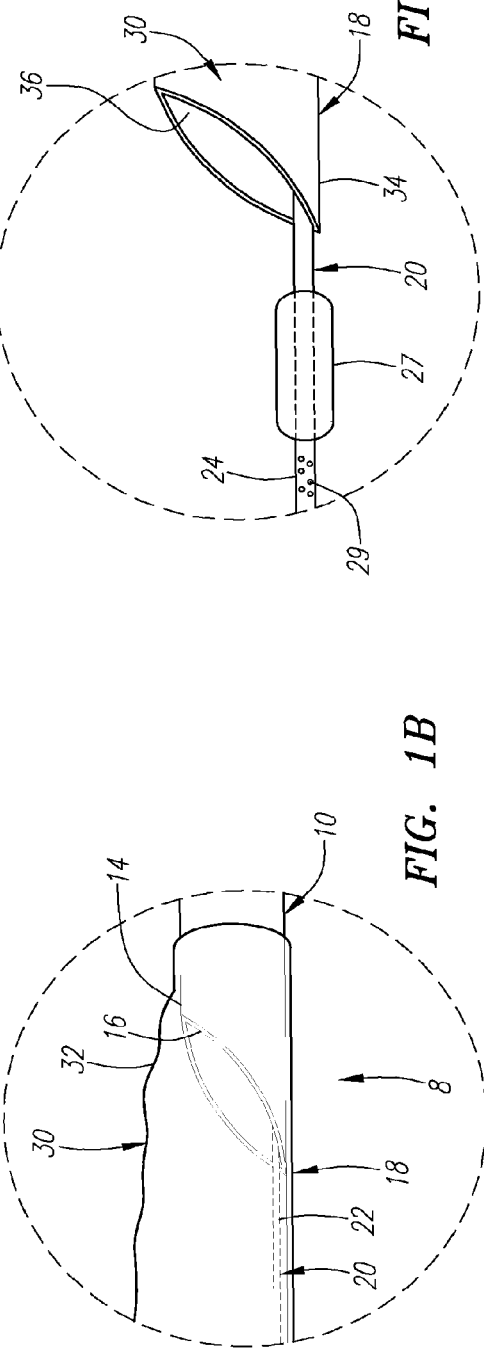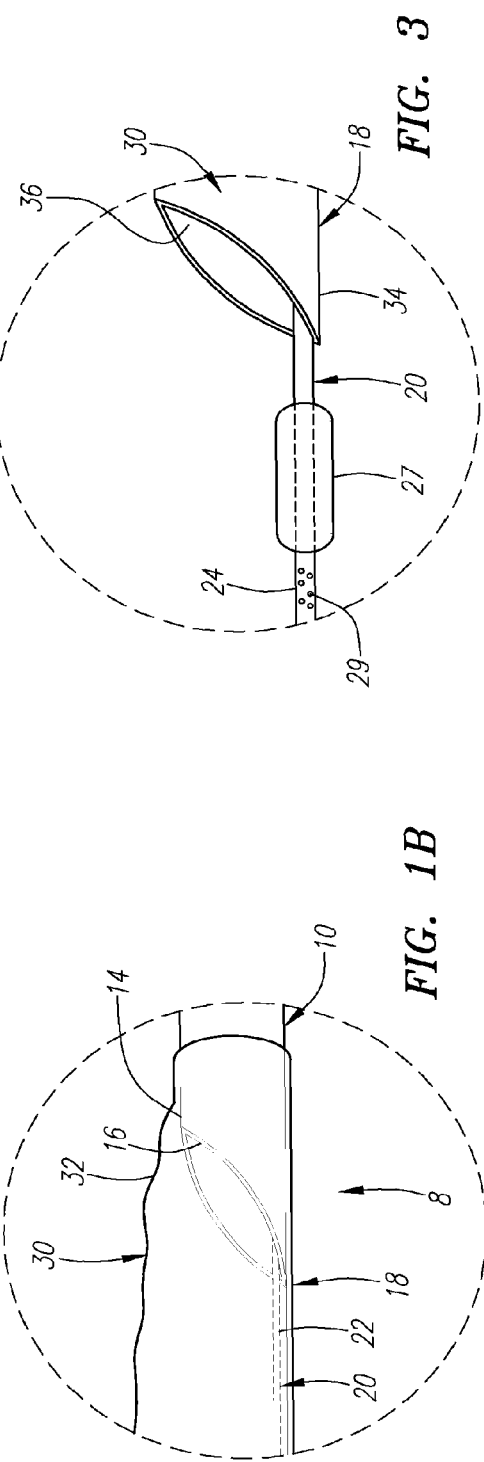

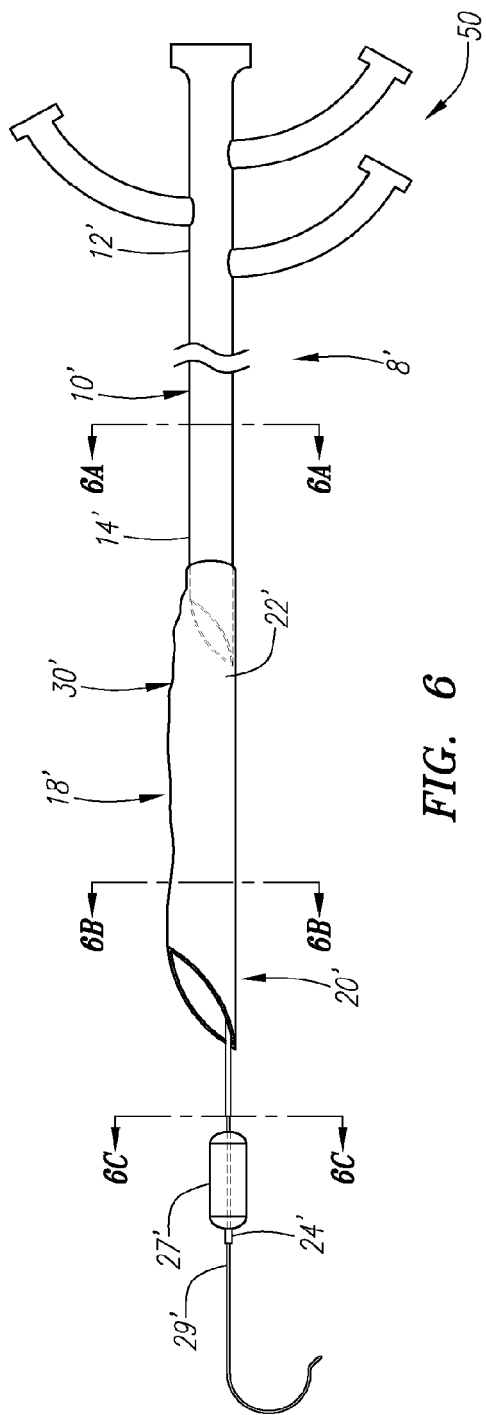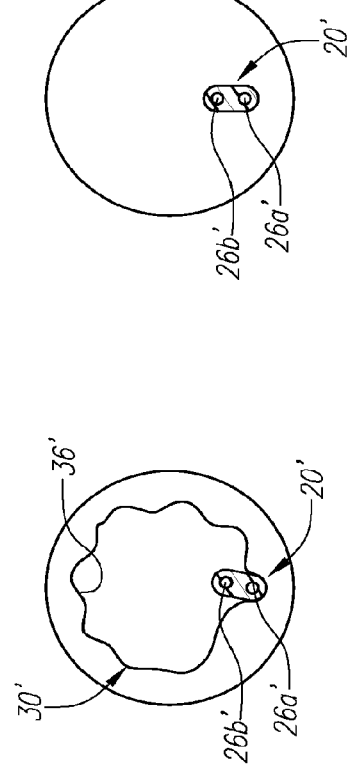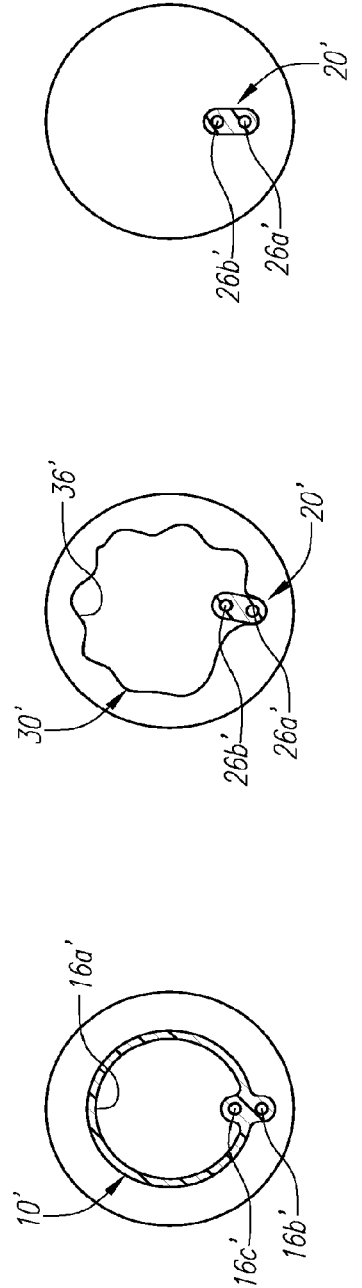
FIG. 6
FIG. 6A
FIG. 6B
FIG. 6C

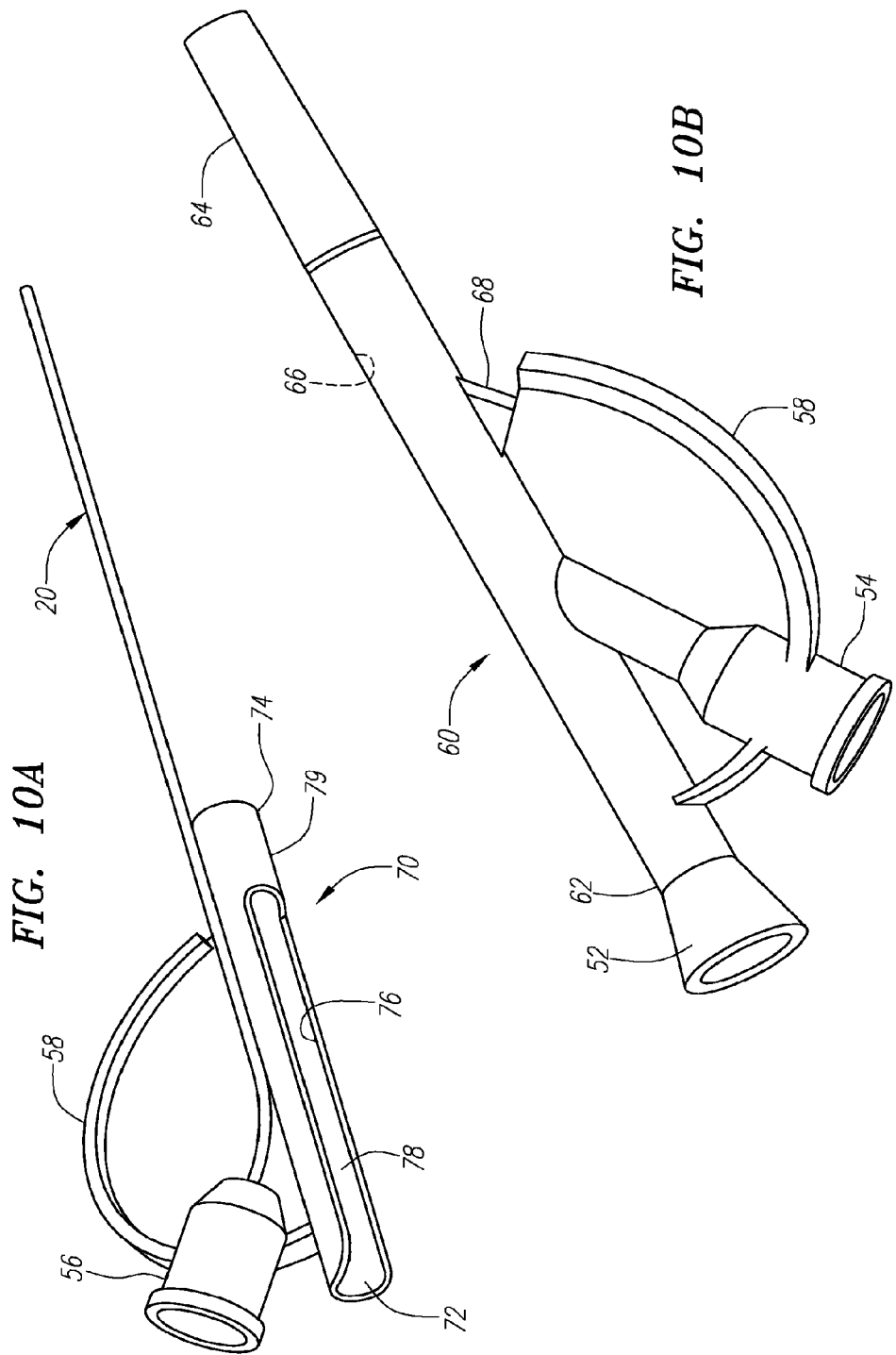

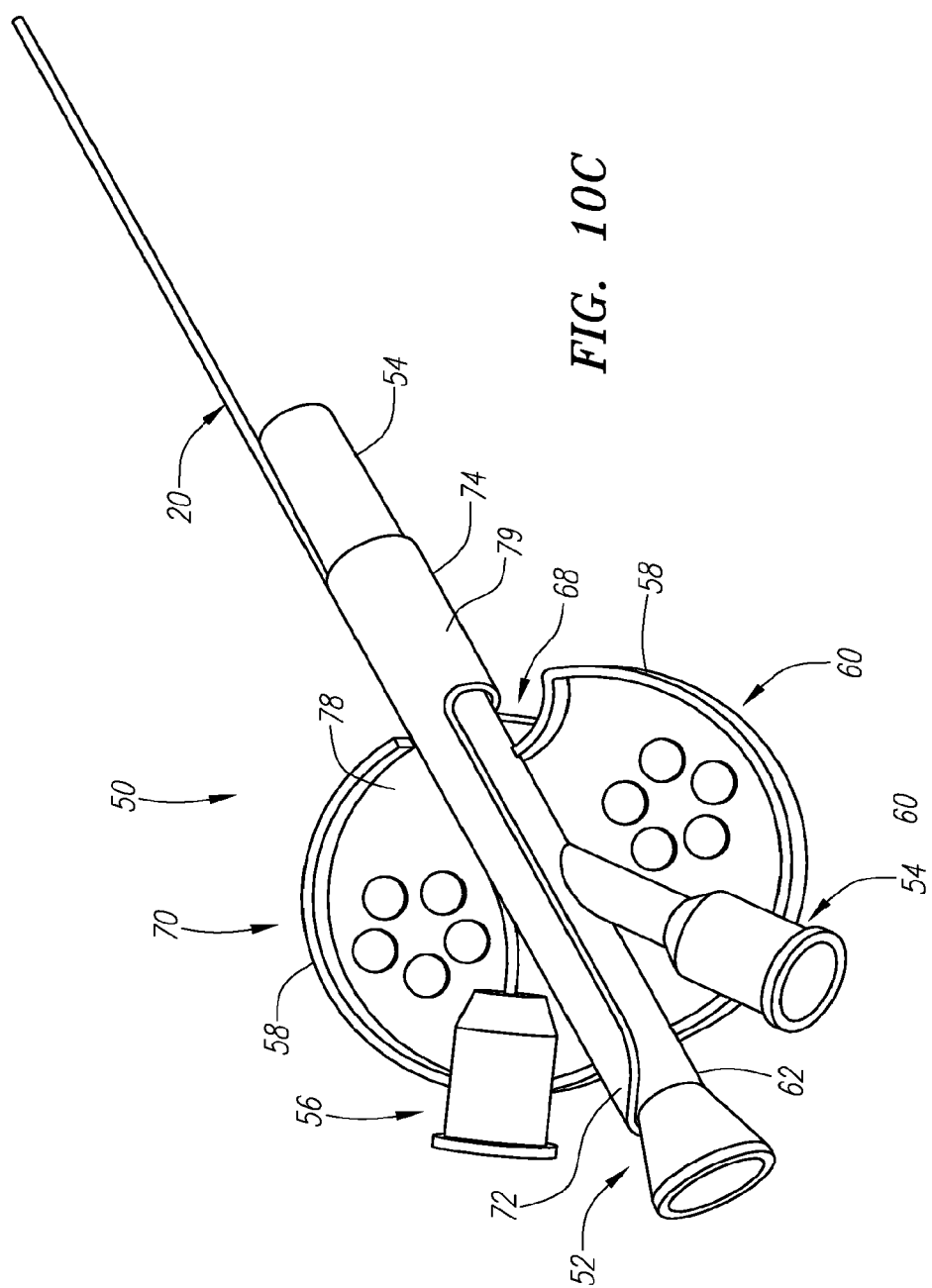

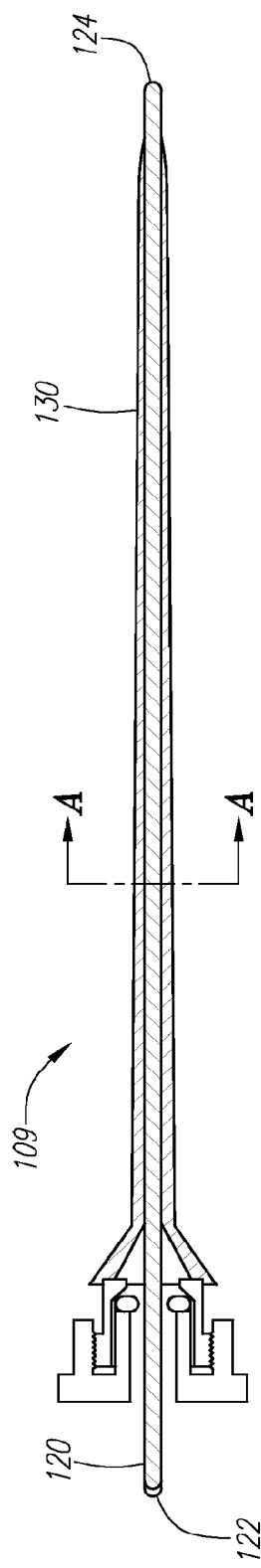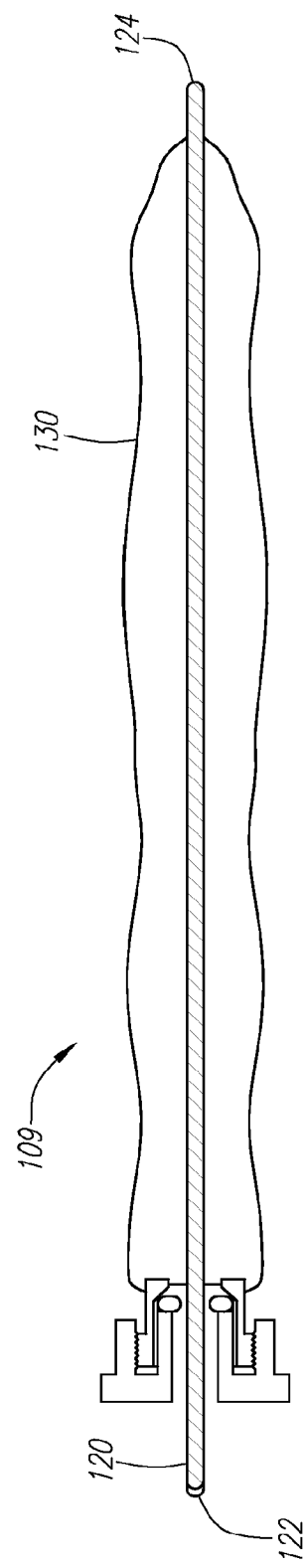
FIG. 24A
FIG. 24B

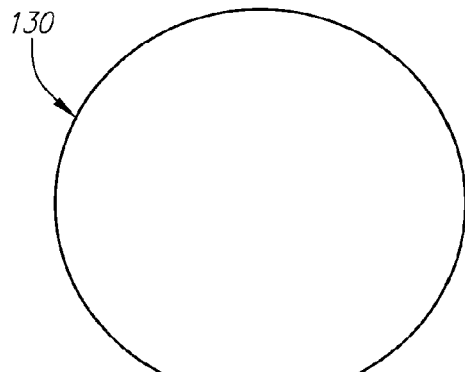
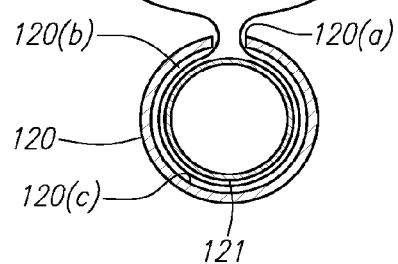
FIG. 25
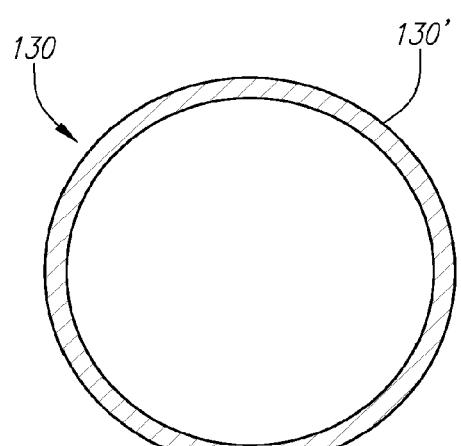
FIG. 26
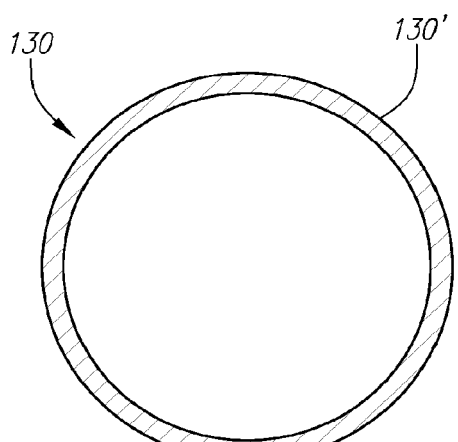
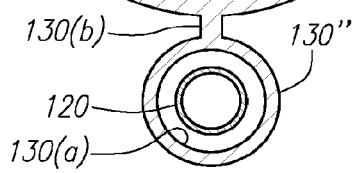
FIG. 27

FIG. 31A
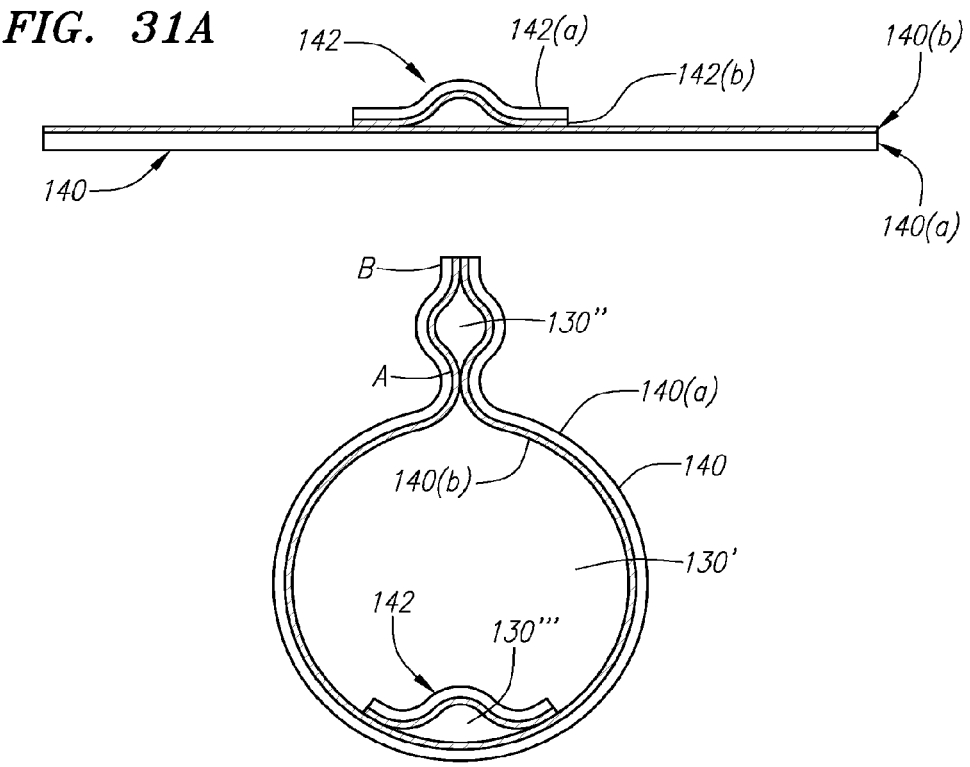
FIG. 31B
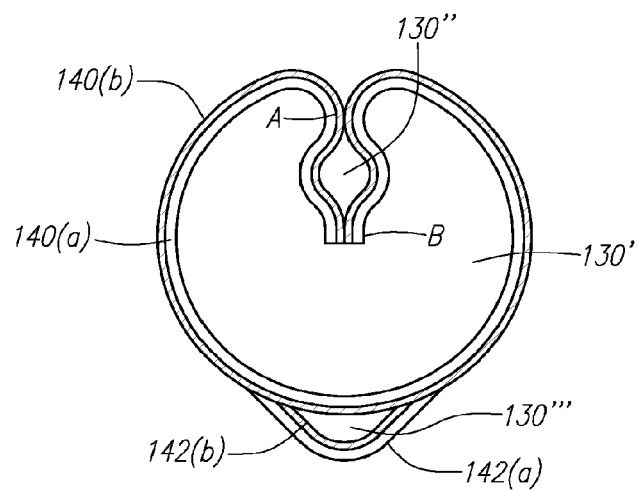
FIG. 31C

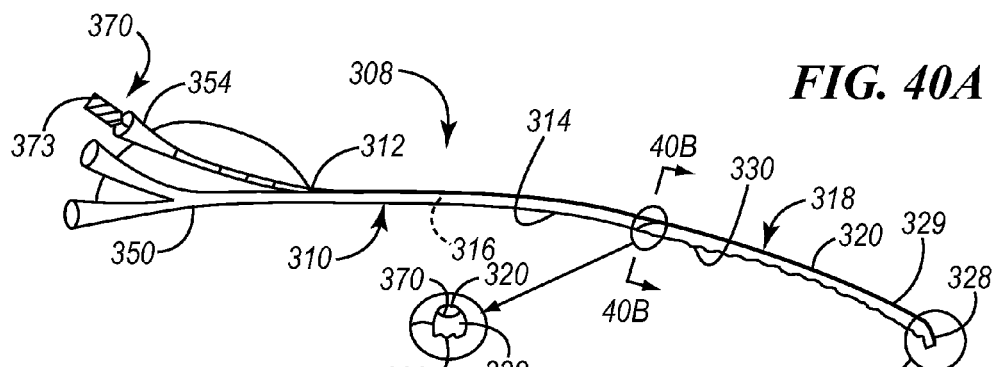
FIG. 40A
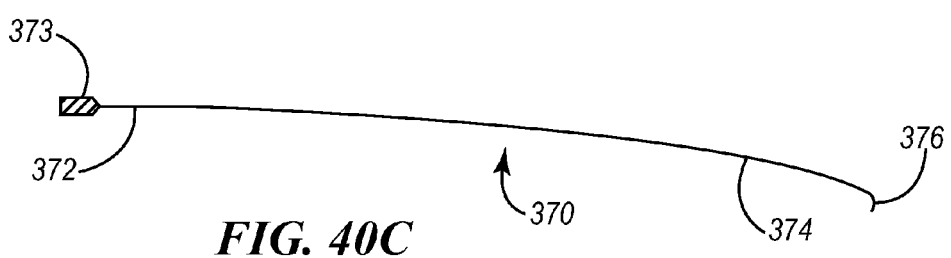
FIG. 40B
FIG. 40C
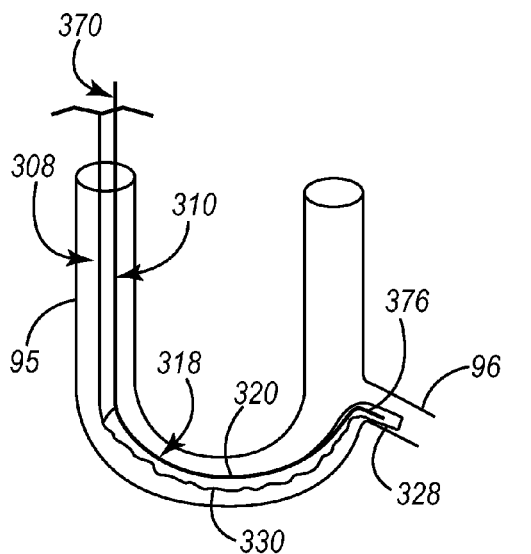
FIG. 40D
FIG. 41

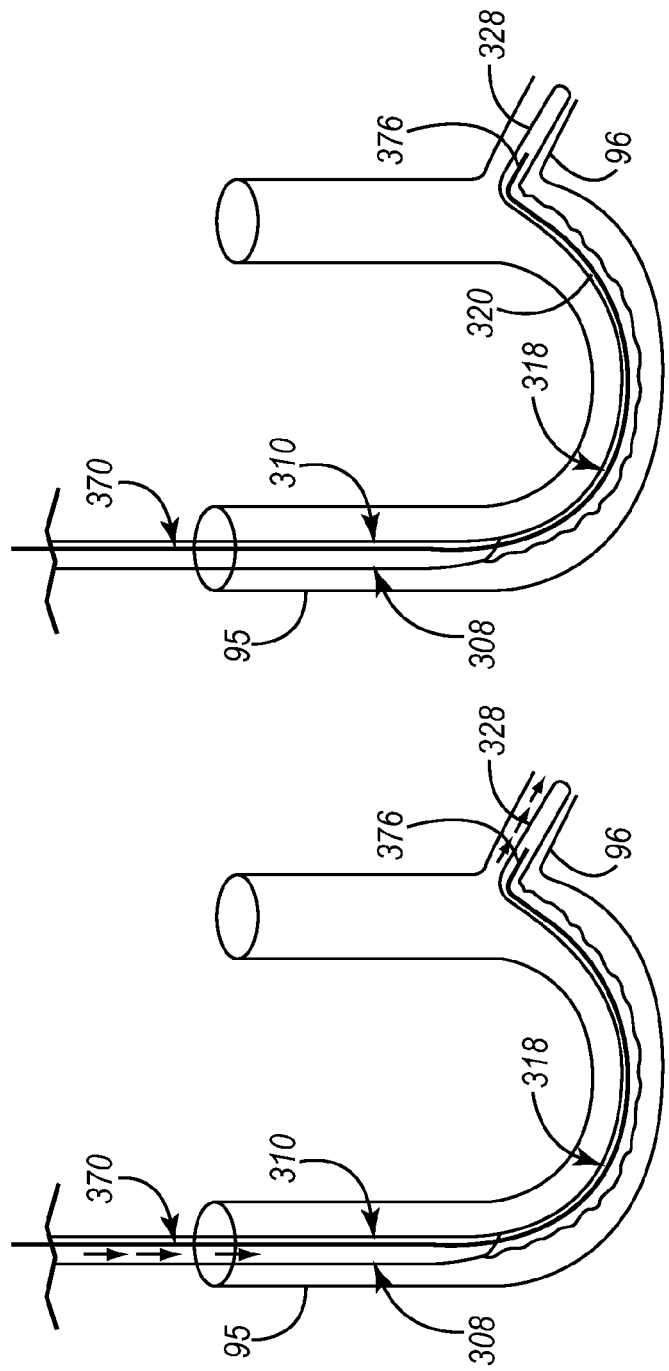

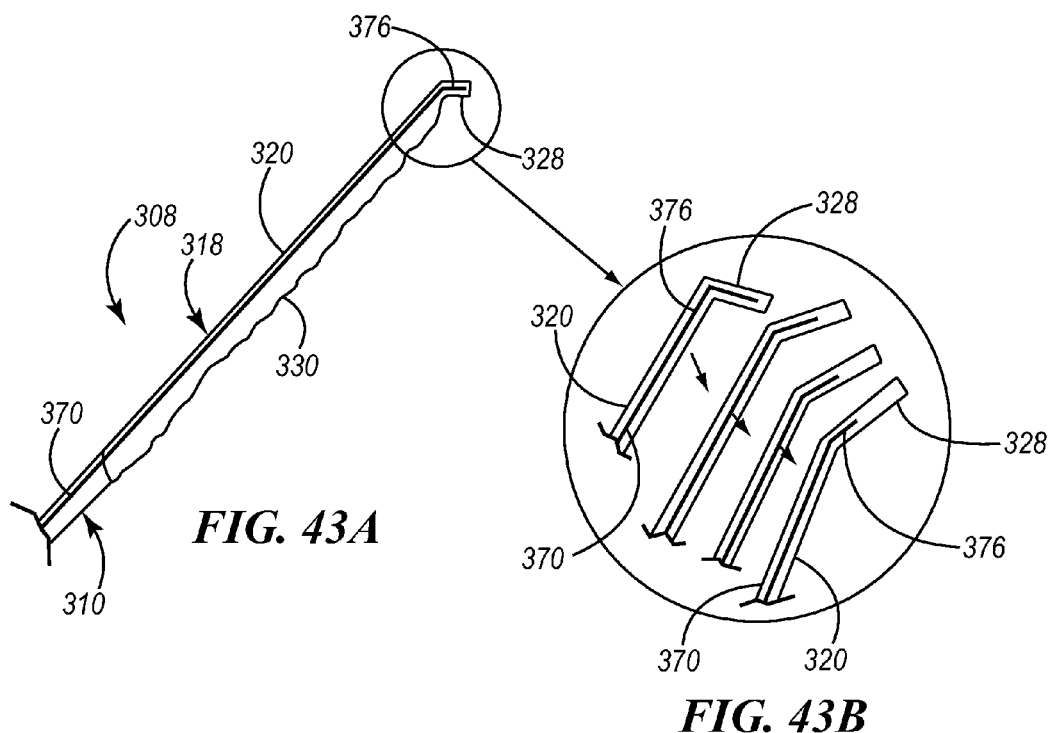
FIG. 43A
FIG. 43B
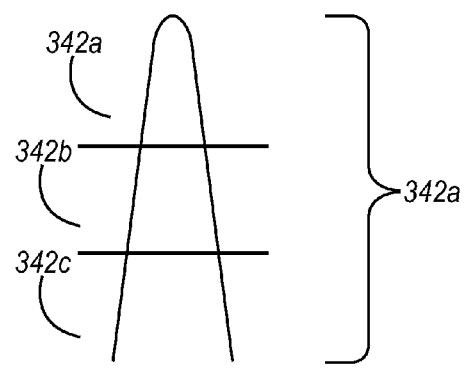
FIG. 44A

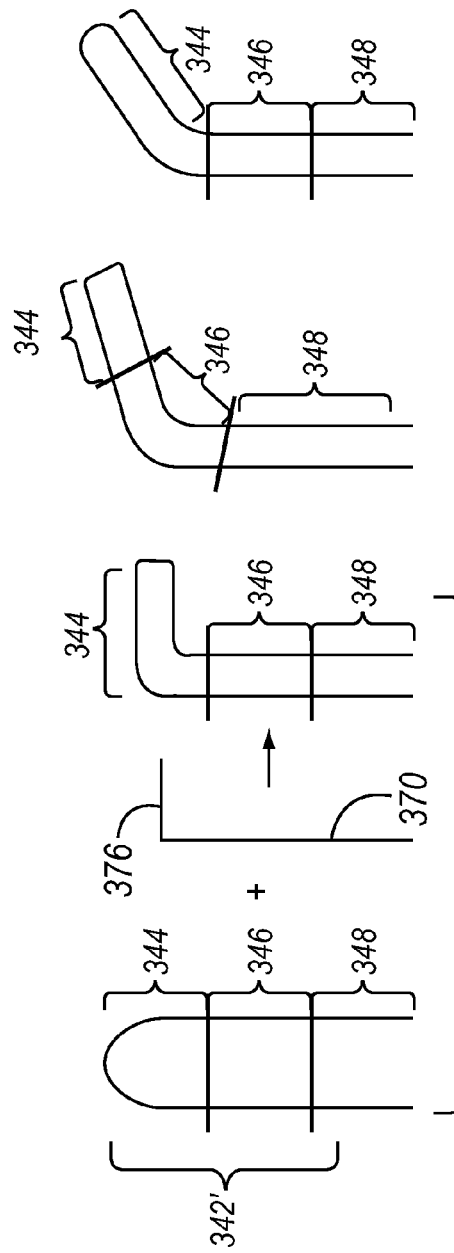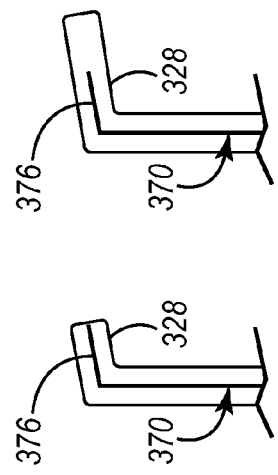

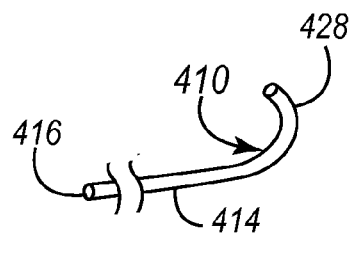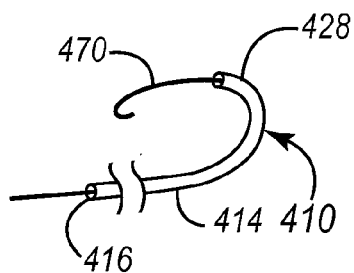
*FIG. 46A*  *FIG. 46B*
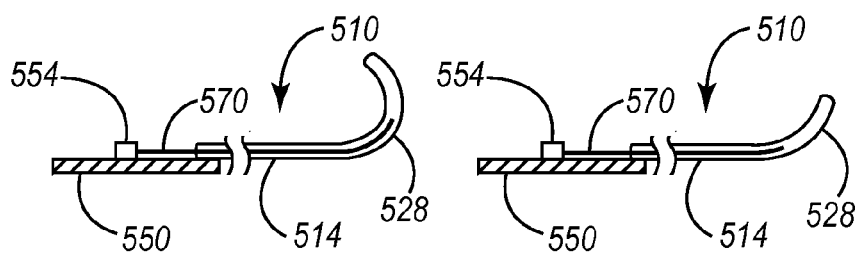
*FIG. 47A*  *FIG. 47B*
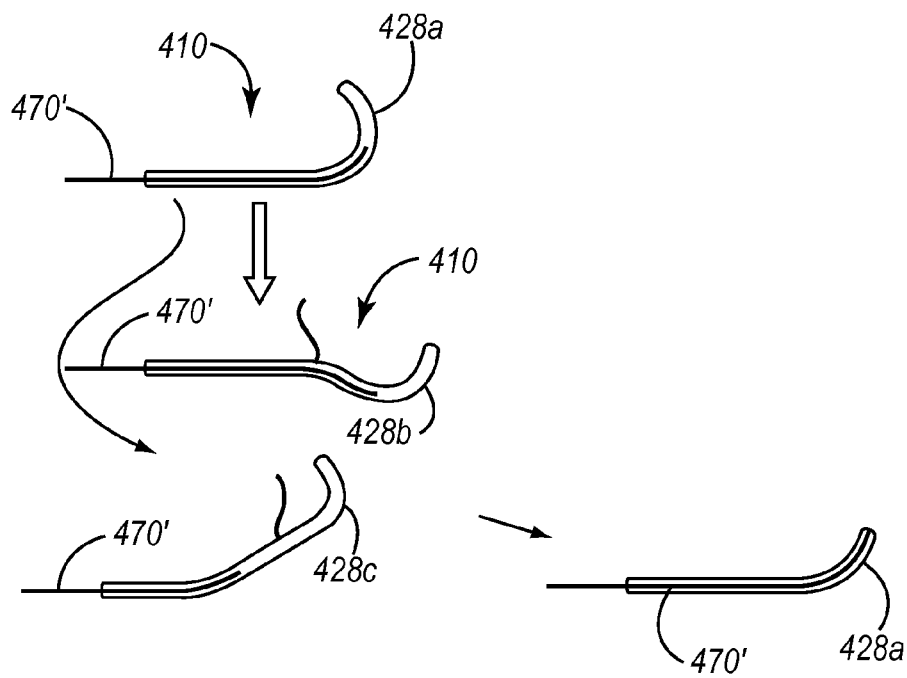
*FIG. 48*

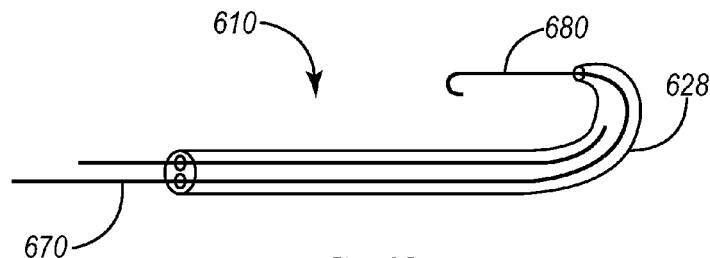
FIG. 49
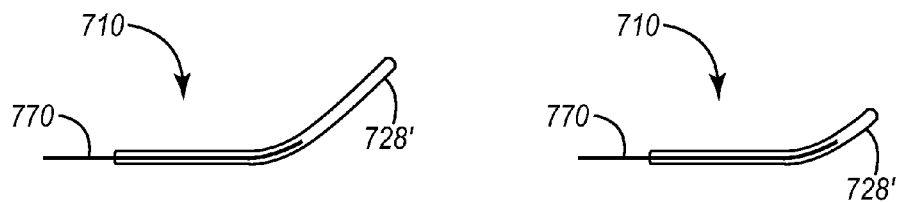
FIG. 50A  FIG. 50B
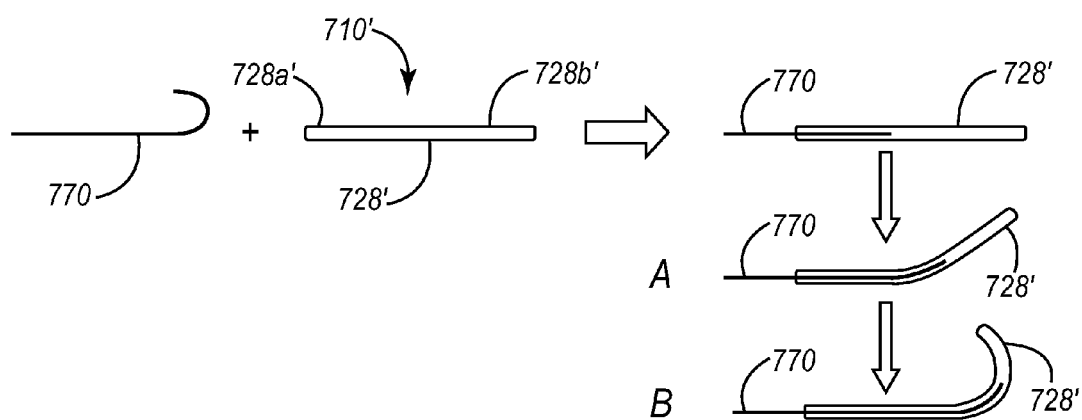
FIG. 51

SHAPEABLE OR STEERABLE GUIDE SHEATHS AND METHODS FOR MAKING AND USING THEM

This application claims benefit of provisional application Ser. No. 60/798,915, filed May 9, 2006. This application is also a continuation-in-part of co-pending application Ser. No. 11/347,361, filed Feb. 3, 2006, which claims benefit of provisional applications Ser. No. 60/649,497, filed Feb. 3, 2005, and 60/752,763 filed Dec. 20, 2005, and is a continuation-in-part of co-pending application Ser. No. 10/958,034, filed Oct. 4, 2004 and Ser. No. 11/062,074 filed Feb. 17, 2005. The entire disclosures of these applications are expressly incorporated herein by reference.

FIELD OF THE INVENTION

The present invention relates generally to apparatus and methods for delivering instruments and/or agents during a medical procedure, and, more particularly, to apparatus and methods for delivering pacing leads or other devices, and/or for navigating and/or cannulating the coronary sinus, coronary vein branches, and/or other branches within a patient's vasculature.

BACKGROUND

Minimally invasive procedures have been implemented in a variety of medical settings, e.g., for vascular interventions, such as angioplasty, stenting, embolic protection, electrical heart stimulation, heart mapping and visualization, and the like. These procedures generally rely on accurately navigating and placing instruments within a patient's vasculature.

There are many risks involved with advancing instruments through a patient's vasculature. For example, a catheter or other instrument may dissect or otherwise damage a wall of a vessel or other body lumen, for example, as the instrument passes through narrow passages and/or tortuous anatomy, e.g., involving sharp bends. Such instruments also risk dislodging embolic material or even perforating body lumens.

In addition, it is often desirable to access body structures with precision such that an instrument or agent may be delivered precisely to a target location, e.g., where the instrument or agent may have diagnostic or therapeutic efficacy.

It is also often desirable to access very small vessels or other body lumens deep within a body, e.g., within a patient's heart, for example, to place a ventricular pacing lead within a coronary vein. However, instrument(s) used to access the vessels, e.g., a guide sheath, lead, and the like, may have a relatively large cross-section and/or may have relatively blunt and/or stiff distal tips, making it difficult to advance such instruments as deeply as desired into such small vessels. In some cases, it is desirable to access smaller side branches, e.g., off of the coronary veins, which may require bending and/or tracking an instrument through tortuous vasculature without causing kinks or torsion load problems.

Accordingly, apparatus, systems, and methods for delivering instruments and/or agents into blood vessels or other body lumens and/or for otherwise accessing vessels or other body lumens would be useful.

SUMMARY OF THE INVENTION

The present invention is directed generally to apparatus and methods for accessing body lumens and/or for delivering instruments and/or agents into body lumens during a medical procedure. More particularly, the present invention is directed to apparatus and methods for delivering pacing leads or other devices, and/or for navigating and/or cannulating the coronary sinus, coronary vein branches, and/or other branches within a patient's vasculature.

In accordance with one embodiment, an apparatus is provided for accessing a body lumen that includes a catheter or other tubular member and a stylet. In one embodiment, the catheter may include a proximal tubular member, a distal end sized for insertion into a body lumen, and at least one lumen extending between the proximal and distal ends. An elongate member, e.g., a relatively rigid backbone, may extend distally from the proximal tubular member. Optionally, the elongate member may vary in stiffness over its length, e.g., a distal tip of the elongate member may be relatively flexible, while a proximal portion of the elongate member may be less flexible. An expandable sheath may extend along at least a portion of the elongate member, the sheath being expandable from a contracted condition to minimize a profile of the sheath, e.g., to allow insertion along with the elongate member into a body lumen, and an enlarged condition wherein the sheath at least partially defines a lumen communicating with the tubular member lumen.

The stylet may be slidable distally and/or proximally along the elongate member and/or may be rotatable relative to the elongate member. For example, the elongate member may include one or more lumens, e.g., extending from the proximal portion to the distal tip, and the stylet may be slidable within one of the lumens. For example, the stylet may be insertable into and/or removable from the elongate member, e.g., insertable into and/or removable entirely from the proximal tubular member. Alternatively, the stylet may be substantially permanently coupled and/or integrated with the apparatus, e.g., to a handle on the proximal end of the proximal tubular member, and an actuator may be provided for advancing and/or withdrawing the stylet, e.g., into and/or from the distal tip of the elongate member.

In one embodiment, the rigidity of the stylet may be substantially greater than a distal tip of the elongate member such that the distal tip complies at least partially with a shape of the stylet when the stylet is advanced and/or positioned within the distal tip. For example, the stylet may have a predetermined shape set into the stylet before use, or the stylet may be malleable such that the stylet may be shaped by a user, e.g., to a desired curvature and/or angle that may facilitate navigation and/or cannulation of a target body lumen. Optionally, the distal tip of the elongate member may be pre-shaped to a predetermined curvature and/or angle, non-shaped, or "floppy," e.g., to facilitate accessing a target body lumen.

Alternatively or in addition, the distal tip may be tapered and/or may include one or more different materials with varying stiffness profiles. For example, advancement and/or retraction of a shaped stylet may form varying curvatures and/or deflections for navigation through a patient's vasculature, other body lumens, and/or body cavities, e.g., based upon varying stiffness profiles along a length of the distal tip.

In a first embodiment, the stylet may have a distal shape-set tip and a substantially flexible distal tip may be provided on the elongate member that conforms substantially to the angle of deflection of the stylet tip. In another embodiment, the elongate member may include a shape-set distal tip and the stylet may include a shape-set tip such advancement of the stylet changes the shape of the distal tip and withdrawal of the stylet may bias the distal tip back towards its initial shape-set. Optionally, the stylet may be integrated with a handle of the tubular member to facilitate advancing and/or advancing the stylet while performing a medical procedure. In a further embodiment, the stylet may be removable and/or rotatable relative to the elongate member. For example, the shape-set distal tip of the elongate member may be advanced within a body lumen with the shape-set stylet in one orientation, and the stylet may be rotated, advanced, retracted, and/or otherwise moved relative to the distal tip such that each of the shape-set combinations may produce different profiles that may be shaped and/or steerable to facilitate tracking and/or navigation within a body cavity or lumen.

For example, such shapes may be optimized for cannulating tributaries within a patient's coronary venous system, such as mid-cardiac, posterior, lateral, antero-lateral, or other suitable targets for placing pacing leads. Additionally, shapes may be selected that facilitate direct delivery of leads to the right atrial, right ventricular, or other chambers of the heart.

In yet another embodiment, a catheter with a shape-set stylet may achieve various deflections and/or geometries from advancing and/or retracting the stylet for further accessing a coronary side-branch or tributary. For example, as the stylet's position is adjusted, the catheter may exhibit varying curvatures to facilitate navigation through vessels and side-branches. In one embodiment, the stylet may be held substantially stationary while the catheter is advanced, e.g., over the stylet, to facilitate positioning within a targeted side branch or other body lumen. If the distal tip is shaped, a side branch having an acute take-off angle may be easily cannulated using a combination of a shape-set distal tip and a shape-set stylet.

In accordance with another embodiment of the invention, an apparatus is provided for accessing a body lumen that includes a tubular proximal portion, and an expandable distal portion. In one embodiment, the proximal portion may include a proximal end, a distal end sized for insertion into a body lumen, and a lumen extending between the proximal and distal ends. The distal portion may include an elongate pushable and/or stiffening member or "backbone" extending from the distal end of the tubular member, and an expandable sheath that is expandable from a contracted condition to minimize a profile of the sheath to allow insertion along with the elongate member into a body lumen, and an enlarged condition wherein the sheath at least partially defines a lumen communicating with the tubular member lumen. through the sheath. A stylet or other member may be a movable relative to the stiffening member for modifying a stiffness and/or changing a shape of the stiffening member.

In accordance with another embodiment, a method is provided for accessing a body lumen using an apparatus including a tubular proximal portion and an expandable distal portion having a size smaller than the proximal portion. The distal portion is advanced into a patient's body, e.g., vasculature, with an expandable sheath thereon in a contracted condition. The proximal portion has sufficient length such that a distal end of the proximal portion may reach a first location within the patient's body, e.g., including relatively large body lumens, passages, or chambers, such as the vena cava, right atrium, and/or coronary sinus. With the proximal portion reaching the first location, the distal portion may extend into relatively smaller body lumens, such as the coronary veins, to a target location that is to be accessed. A stylet or other member may be advanced relative to the distal portion for changing a shape of the distal portion to access a side branch extending from the first location. For example, the distal portion may have a first shape for accessing the first location, and the stylet may change the first shape to a second shape for accessing the side branch. Optionally, after accessing the side branch, the distal portion may be advanced over the stylet into the side branch.

The expandable sheath may be expanded, thereby providing a substantially continuous lumen through the proximal and distal portions to the target location. In one embodiment, a cardiac pacing lead may be advanced through the proximal portion and the expandable sheath to deliver the lead to the target location. Because such a lead may be floppy, the proximal portion may guide the lead through the relatively large body lumens, passages, or chambers, while the expandable sheath may guide the lead through relatively small and/or tortuous body lumens to the target location. Once the lead is delivered to the target location, the apparatus may be removed.

In accordance with another embodiment, a thin walled flexible sleeve is provided that includes a main lumen and an elongate steering element attached to the sleeve, the steering element including a secondary lumen for receiving a pull wire or similar element. The main lumen may be sized for delivery of a lead, guidewire, or similar device. The steering element may be pushed, pulled, and/or otherwise manipulated for deflecting a portion of the sleeve, e.g., a tip of the sleeve at a distal-most point of attachment of the steering element. The steering element may be attached to the sleeve at one or more locations, e.g., using a friction fit, bonding, mechanical fasteners, or similar mechanisms for attachment at the tip of the sleeve.

Optionally, the steering element may be removable from and/or adjustable relative to the sleeve. For example, a constricting mechanism may be provided that holds the steering element in place when the mechanism is activated and/or before the mechanism is removed. Alternatively, the sleeve may include an extra lumen that may be pressurized or otherwise inflated to grip or hold onto the steering element by friction during delivering. To remove or disable the steering element, the extra lumen may be evacuated, thereby removing the pressure-activated friction holding the steering element.

In yet another embodiment, an apparatus is provided that includes a thin walled flexible sleeve, including a first or major lumen, e.g., sized to accept a lead, guidewire, or similar device, a steering element, and a stiffening element. The stiffening element may be disposed within a second or minor lumen, e.g., within the sleeve or steering element. The stiffening element may be fixed or slidable, e.g., to allow for variable steering. In one embodiment, the steering element and stiffening element may be adjacent to each other on the sleeve. Alternatively, the steering and stiffening elements may be placed separately such that they are apart. Furthermore, there may be one or more stiffening elements and/or steering elements.

Other aspects and features of the present invention will become apparent from consideration of the following description taken in conjunction with the accompanying drawings.

BRIEF DESCRIPTION OF THE DRAWINGS

The drawings illustrate exemplary embodiments of the invention, in which:

FIG. 1A is a perspective view of a first embodiment of a sheath apparatus, including a tubular proximal portion and an expandable distal portion.

FIG. 1B is a perspective detail of an intermediate portion of the apparatus of FIG. 1.

FIG. 3 is a side view of a distal end of the apparatus of FIG. 1.

FIG. 6 is a side view of another embodiment of a sheath apparatus, including a tubular proximal portion and an expandable distal portion.

FIGS. 6A-6C are cross-sections of the apparatus of FIG. 6, taken along lines 6A-6A, 6B-6B, and 6C-6C, respectively.

FIGS. 10A and 10B are perspective views of inner and outer members of the handle apparatus of FIG. 9, respectively.

FIG. 10C is a perspective view of the inner and outer members of FIGS. 10A and 10B assembled together.

FIGS. 24A and 24B are side views of another embodiment of a sheath apparatus including a stiffening member and an expandable sheath carried by the stiffening member in collapsed and expanded conditions, respectively.

FIGS. 25-29 are cross-sectional views of alternative embodiments of the sheath apparatus of FIGS. 24A and 24B.

FIGS. 31A-31C are cross-sectional views showing a method for constructing a flexible sheath.

FIG. 40A is a side view of still another embodiment of a sheath apparatus, including a tubular proximal portion, an expandable distal portion, and a stylet received within the distal portion.

FIG. 40B is a cross-section of the apparatus of FIG. 40B, taken along line 40B-40B.

FIG. 40C is a side view of the stylet removed from the apparatus of FIG. 40A.

FIG. 40D is a detail of the distal tip of the apparatus of FIG. 40A, showing features on the distal tip and stylet for preventing the stylet from being advanced beyond the distal tip.

FIG. 41 is a cross-sectional view of a patient's body including a main body lumen and a branch body lumen, showing a method for accessing the branch using a sheath apparatus.

FIGS. 42A and 42B are cross-sectional views of a patient's body showing another method for accessing a branch using a sheath apparatus.

FIG. 43A is a side view of a distal portion of a sheath apparatus.

FIG. 43B is a detail of the distal portion of the apparatus of FIG. 43A, showing a stylet being manipulated to change a shape of a distal tip of the sheath apparatus.

FIGS. 44A-44D are details showing various tip configurations that may be provided on a sheath apparatus.

FIGS. 45A and 45B are details showing relative movement of a stylet within a distal tip of a sheath apparatus.

FIGS. 46A and 46B are side views of a shaped distal portion of a catheter with a shape of the distal portion being changed by insertion of a guidewire therein.

FIGS. 47A and 47B are side views of another embodiment of a shaped distal portion of a catheter including a stylet for changing a shape of the distal portion.

FIG. 48 is a detail of a shaped distal portion of a catheter, showing a shape of the distal portion being changed during insertion of a stylet into the distal portion.

FIG. 49 is a side view of yet another embodiment of a shaped distal portion of a catheter including an integrated stylet.

FIGS. 50A and 50B are side views of still another embodiment of a shaped distal portion of a catheter including a stylet being advanced therein.

FIG. 51 shows another embodiment of a distal portion of a catheter having a variable stiffness, showing a stylet being advanced therein.

DETAILED DESCRIPTION OF THE EXEMPLARY EMBODIMENTS

Figure 2:
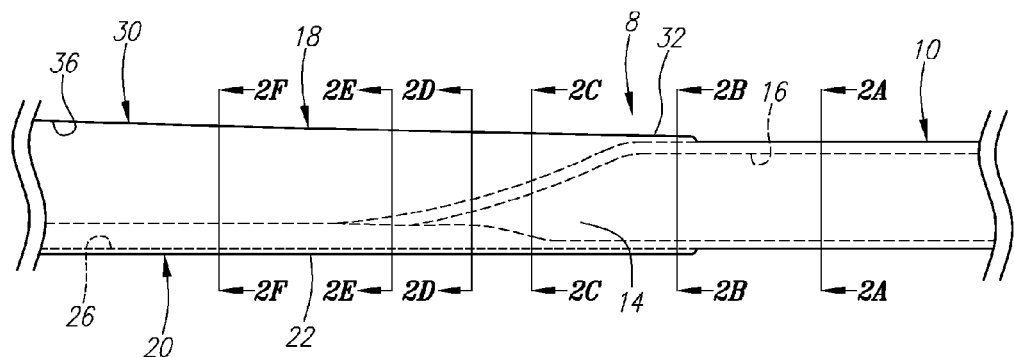
FIG. 2 is a side view of an intermediate portion of the apparatus of FIGS. 1A and 1B.

Turning to the drawings, FIGS. 1A and 1B show a first embodiment of an apparatus 8 for providing access within a body lumen (not shown) and/or for delivering one or more instruments (also not shown) within a body lumen, such as a vessel within a patient's vasculature, a passage within a patient's gastrointestinal tract, urogenital tract, respiratory tract, lymphatic system, and the like.

Generally, the apparatus 8 includes a tubular proximal portion 10 and an expandable distal portion 18. The tubular proximal portion 10 is an elongate tubular member, e.g., a catheter, sheath, and the like, including a proximal end 12, a distal end 14 sized for insertion into a body lumen, and a lumen 16 extending between the proximal and distal ends 12, 14. Optionally, the tubular proximal portion 10 may include one or more additional lumens (not shown), e.g., for receiving a guide wire, inflation media, and/or for perfusion, as described further below. Such additional lumens may be disposed concentrically around one another or in a side-by-side arrangement.

The wall of the tubular portion 10 may be sufficiently thick such that the diameter (or other peripheral dimension) of the tubular portion 10 remains substantially fixed during use of the apparatus 8. The wall of the tubular portion 10 may be rigid or flexible, although self-supporting such that the tubular portion 10 does not collapse on itself. The tubular portion 10 may be sufficiently flexible to allow the tubular portion 10 to bend or otherwise be advanced through a patient's vasculature, while minimizing the risk of kinking or buckling.

The tubular portion 10 may be formed from uniform or variable flexibility material along its length between the proximal and distal ends 12, 14, as desired. For example, it may be desirable for the proximal end 12 to be substantially rigid or semi-rigid, e.g., to facilitate pushing the apparatus 8, while the distal end 14 may be semi-rigid or substantially flexible to accommodate advancement through bends within a patient's vasculature.

The tubular portion 10 may be formed from a variety of materials, such as PTFE, FEP, PFA, PE, Polyamides (Nylon), Polyimide, Pebax, Urethane, and the like. Optionally, the tubular portion 10 may include one or more braids or coils, e.g., embedded within the wall, to provide reinforcement for the tubular portion. In exemplary embodiments, the tubular portion 10 may have a diameter between about half and five millimeters (0.5-5 mm), a wall thickness between about 0.02 and one millimeters (0.02-1.0 mm) (cross-sectional configurations, i.e. multi-lumen cross-sections, and the like may cause wall thicknesses to vary), and a length between about ten and one hundred ten centimeters (10-110 cm), or between about forty and seventy centimeters (40-70 cm). For example, if a subclavian approach is to be used, the proximal portion 10 may have a length of about thirty centimeters (30 cm) or less, while if a femoral approach is to be used, the proximal portion 10 may have a length of about one hundred ten centimeters (110 cm) or more. In one embodiment, the tubular portion 10 may have a length sufficient to reach the vena cava, the right atrium, or the coronary sinus of a patient's heart from a percutaneous entry location, such as a subclavian vein, as described further below.

With continued reference to FIGS. 1A and 1B, the expandable distal portion 18 generally includes an elongate stiffening member 20 providing a "backbone" for the distal portion 18 and an expandable sheath 30. The stiffening member 18 and/or expandable sheath 30 may be attached to or otherwise extend distally from the distal end 14 of the tubular portion 10, as described further below. The stiffening member 20 facilitates advancing the expandable sheath 30 through one or more body lumens, e.g., through a patient's vasculature. The distal portion 18 may be similar in construction and use as the apparatus disclosed in application Ser. No. 10/423,321, filed Apr. 24, 2003, the entire disclosure of which is expressly incorporated by reference herein. In addition or alternatively, the distal portion 18 may be constructed using materials and/or methods similar to any of the embodiments described elsewhere herein.

The stiffening member 20 may be a solid or hollow guidewire, catheter, thread or other filament (e.g., a monofilament), and/or other solid or hollow elongate member. The stiffening member 20 may be sufficiently flexible to facilitate advancement through tortuous anatomy without causing dissection or perforation, yet may have sufficient column strength and/or torque-ability to be "pushable," i.e., such that the stiffening member 20 may be advanced through a body lumen by pushing the proximal end 12 of the tubular portion 10 without substantial risk of kinking and/or buckling. In addition, the stiffening member 20 may also provide sufficient support to facilitate introducing secondary devices, such as a cardiac lead, through the distal portion 18. Cardiac leads or other floppy devices may be difficult to deliver, because of their ability to "prolapse" or double over on themselves in large lumens, like atria, rather than advance to a desired proper location.

In addition, the stiffening member 20 may have sufficient length to be advanced from a first location where the proximal portion 12 terminates, e.g., within the right atrium or coronary sinus of a heart, and a site to be accessed and/or treated, e.g., a coronary vein, as described further below. In exemplary embodiments where the stiffening member 20 is attached to the distal end 14 of the proximal portion 10, the stiffening member 20 may be between about ten and fifty centimeters (10-50 cm), or may be not more than about thirty centimeters (30 cm), not more than about ten centimeters (10 cm), or not more than about seven centimeters (7 cm). Alternatively, the stiffening member 20 may extend proximally the entire length of the proximal portion 10, e.g., within or along the proximal portion 10, and therefore may have additional length corresponding to the length of the proximal portion 10.

As shown in FIGS. 1A-3, the stiffening member 20 may be an elongate member including a proximal end 22, and a distal end 24 having a size and/or shape for insertion into a body lumen. Optionally, the stiffening member 20 may terminate in a rounded or other substantially atraumatic distal tip 28, e.g., a "J" tip, a balloon or other expandable member, and the like, as explained further below. If desired, the distal tip 28 may be shaped to provide steerability and/or directionality, or may include one or more internal elements to provide a steerable distal tip.

Figure 21A:
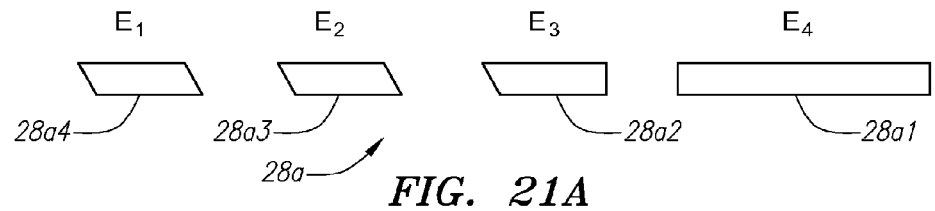
FIGS. 21A, 22A, and 23A are exploded side views of distal tips of a stiffening member having multiple sections providing a variable stiffness for the distal tip.
Figure 21B:
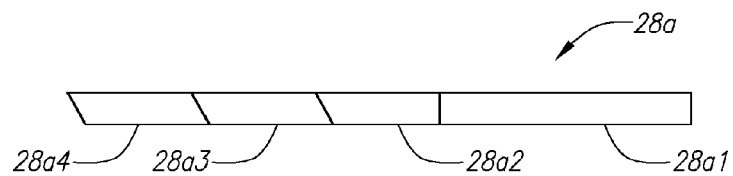
FIGS. 21B, 22B, and 23B are side views of the distal tips of FIGS. 21A, 22A, and 23A, respectively, with the sections assembled together.

Optionally, as shown in FIGS. 21-23, the distal tip 28 may be formed from multiple sections of tubing or other material having different stiffness or modulus of elasticity. For example, as shown in FIGS. 21A and 21B, the distal tip 28a may include a first tubular section 28a1 having a stiffness similar to the adjacent portion of the stiffening member (not shown). Distally adjacent tubular sections 28a2-28a4 may have progressively less stiffness, e.g., such that the distal-most section 28a4 is "floppy" or soft, which may facilitate advancing the distal tip 28a through tortuous anatomy.

Figure 22A:
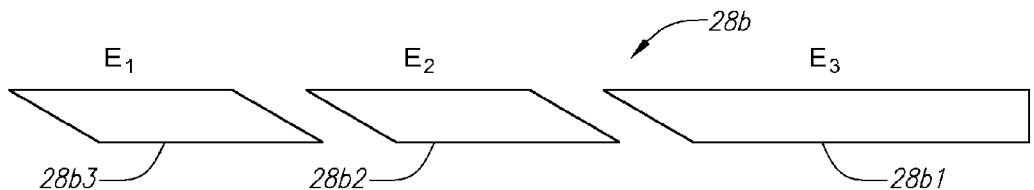
Figure 22B:
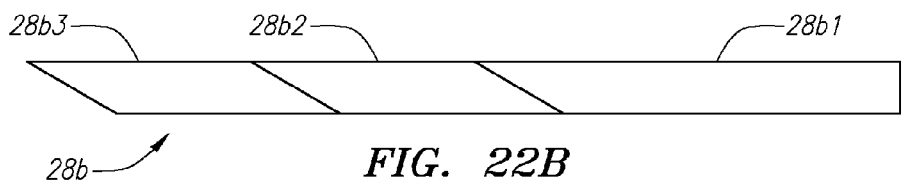
Figure 23A:
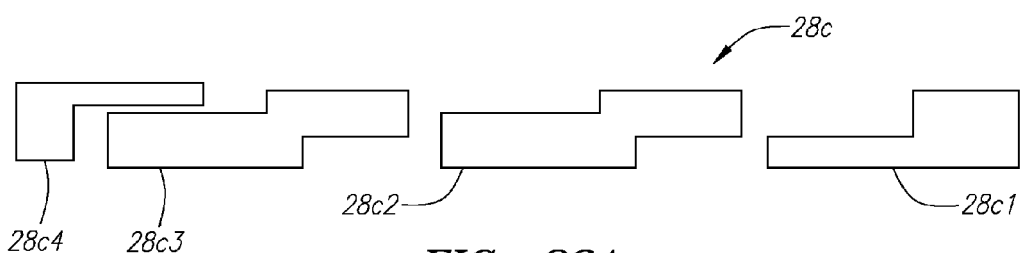
Figure 23B:
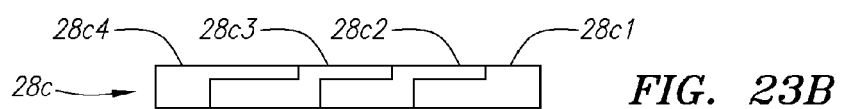

Alternatively, as shown in FIGS. 22A and 22B, sections 28b1-28b3 of the distal tip 28b may be angled on the ends to be attached to one another. This may create a distal tip 28*b* whose stiffness changes less abruptly. In a further alternative, shown in FIGS. 23A and 23B, the sections 28*c*1-28*c*4 may be beveled or otherwise staggered to provide a more gradual and/or continuous change in stiffness along the distal tip 28*c*.

Optionally, the stiffening member 20 may include one or more lumens 26 extending between the proximal and distal ends 22, 24. For example, in the embodiment of FIGS. 1A and 2, the stiffening member 20 includes a single lumen 26, best seen in FIG. 2F. Alternatively, in the embodiment of FIG. 6, the stiffening member 20' includes two side-by-side lumens 26*a*,' 26*b*,' best seen in FIGS. 6B and 6C. The lumen(s) may be sized to allow fluids to be delivered therethrough and/or to receive a stylet, guide wire, catheter, or other instrument (not shown) therethrough, e.g., as described elsewhere herein.

Figures 2A, 2B, 2C:
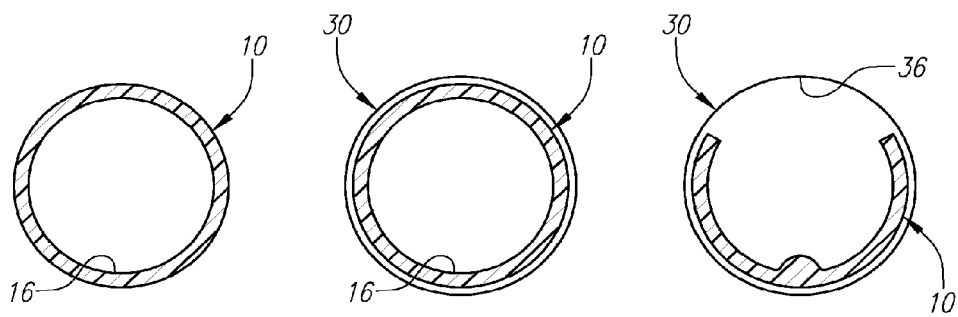
FIGS. 2A-2F are cross-sections of the apparatus of FIG. 2, taken along lines 2A-2A to 2F-2F, respectively.
Figures 2D, 2E, 2F:
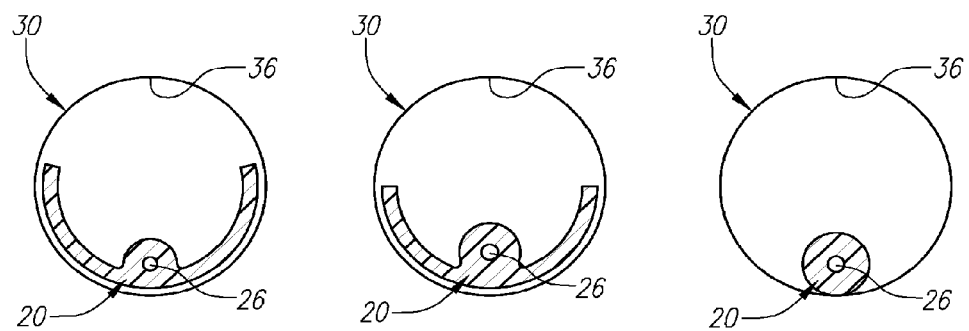

As shown in FIG. 2F, the stiffening member 20 may have a cylindrical or other substantially symmetrical cross-section, e.g., including a single lumen 26. Alternatively, as shown in FIGS. 6B and 6C, the stiffening member 20' may have an asymmetrical cross-section, e.g., including a plurality of lumens 26*a*,' 26*b*.' In other embodiments, the stiffening member may have an arcuate cross-section (not shown), such as those disclosed in application Ser. No. 10/432,321, incorporated by reference above. The diameter or other cross-section of the stiffening member 20 is substantially smaller than that of the tubular proximal portion 10, e.g., between about 0.05-5 millimeters, or between about 0.2-2 millimeters.

Optionally, as best seen in FIG. 3, the stiffening member 20 may include a balloon or other expandable occlusion member 27 on the distal end 24. If a balloon 27 is provided, the stiffening member 20 may include an inflation lumen (not shown) that extends through the stiffening member 20 from the proximal end 12 (see FIG. 1A) to communicate with an interior of the balloon 27. A source of inflation media, e.g., a syringe of saline (not shown) may be coupled to port 56 (see FIG. 1A) that may communicate with the inflation lumen. Exemplary occlusion members that may be provided and methods for using them are disclosed in U.S. Pat. No. 7,591,832, issued Sep. 22, 2009, the entire disclosure of which is expressly incorporated by reference herein.

In addition or alternatively, the stiffening member 20 may include one or more outlet ports 29 on the distal end 24, e.g., distal to the balloon 27, as shown in FIG. 3, or proximal to the balloon 27 (not shown). As shown in FIGS. 6-6C, if the stiffening member 20' includes a balloon 27' and one or more outlet ports 29,' the stiffening member 20' may include two lumens 26*a*,' 26*b*' communicating with the interior of the balloon 27' and the outlet ports, respectively.

The stiffening member 20 may be formed from a variety of materials and using various methods. For example, the stiffening member 20 may be formed from plastic, glass, metal, or composites of such materials using known methods, such as extrusion and the like, thereby providing a desired combination of flexibility and column strength. In exemplary embodiments, the stiffening member 20 may be formed from one or more of polyimide, polyamide (nylon)), Ultem, PEEK, Nitinol, and optionally, may include braid and/or coil reinforcing polymers, similar to other components described herein.

Turning to FIGS. 1B and 2, a transition may be provided between the distal end 14 of the tubular portion 10 and the proximal end 22 of the stiffening member 20. As shown, the distal end 14 of the tubular portion 10 may be beveled or otherwise tapered, e.g., by molding-in the tapered shape or by cutting or otherwise removing a section of the distal end 14. Such a shape may facilitate advancing the tubular portion 10 into a body lumen within which the smaller stiffening member 20 has been previously introduced, as described further below.

Figure 20:
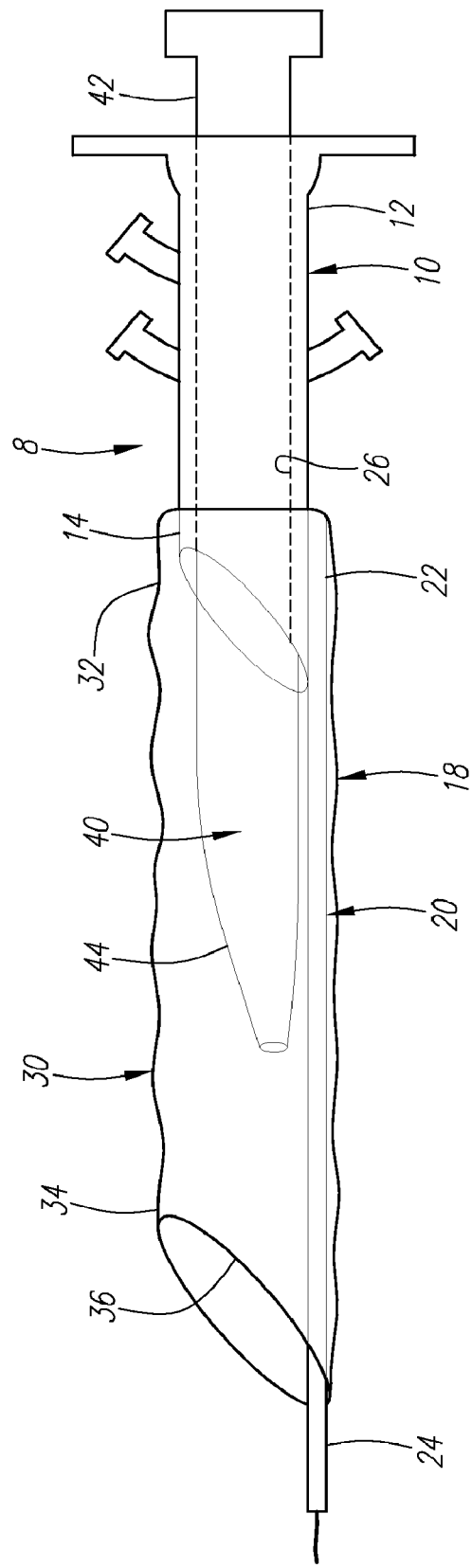
FIG. 20 is a side view of the apparatus of FIGS. 1A and 1B, having an obturator inserted therein for providing a transition between the proximal and distal portions of the apparatus.

In addition or alternatively, as shown in FIG. 20, an obturator 40 may be provided that includes a proximal end 42, and a tapered and/or rounded distal end 44 sized to be slidably inserted into the lumen 26 of the tubular portion 10. The obturator 40 may have a length corresponding to a length of the tubular portion 10 such that the distal end 44 of the obturator 40 extends partially into the expandable distal portion 18 when the obturator 40 is fully advanced into the tubular portion 10. The distal end 44 of the obturator 40 may be relatively flexible and/or soft to provide an atraumatic transition between the tubular proximal portion 10 and the expandable distal portion 18.

Returning to FIGS. 1B and 2, the proximal end 22 of the stiffening member 20 may be attached to the distal end 14 of the tubular portion 10, e.g., such that the stiffening member extends axially and/or tangentially from the wall of the tubular portion 10. The stiffening member 20 may be attached to the tubular portion 10, e.g., by one or more of chemical bonding, thermal bonding, sonic welding, interference fit, and/or one or more cooperating connectors. Alternatively, the tubular portion 10 and stiffening member 20 may be formed as a single piece, e.g., by extrusion, injection molding, and the like.

With additional reference to FIGS. 1A-3, the expandable sheath 30 generally includes a proximal end 32, a distal end 34, and one or more side walls extending between the proximal and distal ends 32, 34, thereby at least partially defining a lumen 36. As used herein, the term "sheath" may include any structure that at least partially defines a lumen, whether the structure is substantially tubular or only partially defines the lumen 36.

The sheath 30 may be expandable from a contracted condition (not shown) to an enlarged condition, as shown in FIG. 1A. When the sheath 30 is in the contracted condition, the distal portion 18 may assume a low profile to facilitate insertion into a body lumen (not shown). To place the sheath 30 in the contracted condition, the sheath 30 may be folded, twisted, wrapped, or otherwise compressed around or adjacent to the stiffening member 20 (e.g., using an internal vacuum with the lumen 36 of the sheath 30 and/or an external force). In another embodiment, the sheath 30 may be left unconstrained. The "limpness" of the sheath 30 may allow the sheath material to readily deflect when the sheath 30 contacts any bodily structures, such that the sheath 30 may perform as if it were maintained in a collapsed configuration, when it is not actually constrained.

Optionally, the sheath 30 may be secured in the contracted condition, e.g., using a constraint (not shown), such as a sheath, tether, or releasable adhesive or bonding material at one or more locations or continuously along the sheath 30. Alternatively, the sheath 30 may simply maintain the contracted condition until an external force, e.g., fluid or an instrument, are delivered therein to expand the sheath 30 towards the enlarged condition. Exemplary apparatus and methods for placing and/or maintaining the sheath 30 in the contracted condition are disclosed in application Ser. No. 10/423,321, incorporated by reference above. In the enlarged condition, the sheath 30 may unfold, untwist, unwrap, or otherwise expand to at least partially define the lumen 36, e.g., for receiving a fluid (e.g., a medicament, anti-thrombotic agent, and the like) and/or one or more instruments therethrough (not shown).

Because the sheath 30 is relatively thin-walled, the distal portion 18 may attain a relatively low profile when the sheath 30 is in the contracted condition compared to the proximal portion 10. For example, with the sheath 30 in the contracted condition, the distal portion 18 may have a maximum diameter between about 0.1 and about ten millimeters (0.1-10 mm), or between about 0.2 and about three millimeters (0.2-3 mm). Conversely, a relatively large lumen 36 may be provided when the sheath 30 is expanded to the enlarged condition, e.g., having a diameter or other maximum cross-section between about 0.3 and about one hundred millimeters (0.3-100 mm), or preferably between about 0.3 and about twenty millimeters (0.3-20 mm).

The sheath 30 may be formed from relatively thin, flexible material, as compared to the stiffening member 20 and/or tubular proximal portion 10. Thus, the sheath 30 may be "flimsy," i.e., may have little or no rigidity such that the sheath 30 provides little resistance to expansion and/or contraction, and/or may conform substantially to anatomy within which it is deployed. As used herein, "flimsy" means that the material of the sheath 30 is not biased to assume any particular configuration or shape, and therefore, the sheath 30 may adopt whatever shape and/or configuration that is imposed upon it, e.g., by being folded or otherwise compressed, by being subjected to external or internal pressure or force, and the like. To achieve this, the sheath 30 may have a relatively thin wall thickness, e.g., between about 0.001-1.25 millimeters, or between about 0.005-0.06 millimeter.

The sheath 30 may be constructed of one or more materials that may be fabricated to a relatively thin, flexible configuration, e.g., polytetrafluoroethylene (PTFE), expanded polytetrafluoroethylene (ePTFE), fluorinated ethylenepropylene (FEP), polyethylene teraphathalate (PET), urethane, olefins, polyethylene (PE), silicone, latex, isoprene, chronoprene; and the like. The sheath 30 may be formed from lubricious material and/or may be coated, e.g., with silicone or other coating, e.g., for facilitating inserting one or more instruments (not shown) through the lumen 36.

In some embodiments, it may be desirable that the internal surface of the sheath 30 be lubricious to allow for smooth passage of an instrument, such as an electrical pacing lead (not shown), therethrough. This may be accomplished by forming the sheath 30 out of a lubricious material such as, a hydrophobic fluoropolymer. Alternatively, the sheath 30 may be formed from material that has been surface-treated and/or coated with a hydrophilic coating material. If it is particularly difficult to treat or coat the interior surface of the sheath 30, the treatment or coating material may be applied to the exterior surface of the sheath 30. The sheath 30 may then be inverted or "everted," for example, by pulling one end of the sheath 30 through the sheath lumen to place the exterior treated/coated surface on the interior of the sheath 30 (i.e., turn the sheath 30 inside-out).

The sheath 30 may be formed from thin-walled polymeric tubing or a thin polymeric film. With respect to tube-based structures, the tubing may be extruded (or co-extruded if multiple lumens are used as is described in more detail below) to a thin wall. Alternatively, one or more post-processing steps, such as blow molding, stretching, or drawing tube through a heated die may be used to form the thin walled sheath 30. In still another embodiment, a thin film may be produced and rolled into a tubular configuration. In this embodiment, the thin film may be surface-treated and/or coated before being rolled into the tubular configuration.

With respect to thin film-based structures, a seam may be formed along all or a portion of the length of the sheath 30. The seam may be formed from any number of methods, for example, chemical bonding with adhesives, heat sealing, ultrasonic welding, laser welding, or mechanical bonding using stitching or the like.

As described above, in one embodiment, the sheath 30 may be formed from a lubricious fluoropolymer. For example, a thin-walled sheath 30 may be formed by rolling a cast thin film formed from PTFE having a layer of FEP formed thereon into a tubular structure. The FEP may then be sealed (for example, by heat sealing) to form the final tubular structure. The PTFE layer is preferably disposed on the interior surface of the sheath 30 since PTFE is more lubricious than FEP.

In still another alternative embodiment, the sheath 30 may be formed from ePTFE manufactured into a thin-walled tube (or multiple tubes) or thin film. Additional lumens may also be formed within the sheath 30. For example, these additional lumens may be used to house the backbone (i.e., elongate stiffening member 20) or used to inject contrast for imaging and/or perfusing blood or other fluids. As one example, additional lumens may be formed by joining un-sintered PTFE or ePTFE tube structures, which may then be heat-sealed along their lengths, followed by a sintering process.

In one embodiment, the sheath 30 is formed from substantially inelastic material, i.e., such that a primary contribution to the sheath 30 expanding and contracting is unfolding or folding the material of the sheath 30. Alternatively, the sheath 30 may be formed from an elastic material such that a secondary contribution to the sheath 30 expanding and contracting is an elasticity of the material of the sheath 30, i.e., such that a circumference or other peripheral dimension of the sheath 30 may increase as the sheath 30 expands towards the enlarged condition.

The sheath 30 may be substantially nonporous. Alternatively, the sheath 30 may be porous, for example, substantially continuously along its length or at one or more locations, e.g., to allow fluid delivered into the lumen 36 to pass through the wall of the sheath 30 in a desired manner, e.g., to deliver fluid to a wall of a vessel (not shown) through which the sheath 30 extends. In a further alternative, the sheath 30 may include one or more discrete openings (not shown) at one or more locations along its length.

In addition or alternatively, the sheath 30 may include a thin mesh, e.g. a perforated urethane film and the like. In a further alternative, the lubricity of the sheath 30 may be enhanced by providing a lubricious coating, lining, ribbing, and the like (not shown), and/or applying a lubricant, e.g., to the interior surface and/or outer surface of the sheath 30. The sheath 30 may include a single layer or multiple layers of such materials, such that a desired flexibility and lubricity is achieved. Thus, the sheath 30 may easily expand and/or line a body lumen to reduce friction and/or accommodate instruments being advanced through the body lumen, as explained further below.

Optionally, the sheath 30 may include one or more reinforcing elements (not shown). For example, a wire, thread, filament, and the like, formed from plastic, glass, metal, or composites of such materials, may be attached to an outer surface, an inner surface, and/or embedded in a wall of the sheath 30. In addition or alternatively, the sheath 30 may include relatively thickened regions that may be formed directly from the wall material. The reinforcing element(s) may extend circumferentially and/or helically around the sheath 30, and/or may extend axially along the sheath 30, depending upon the reinforcement desired. The reinforcement element(s) may also bias the sheath 30 to assume a desired shape or configuration when expanded towards the enlarged condition.

With particular reference to FIGS. 1B and 2, the proximal end 32 of the sheath 30 may be attached to the distal end 14 of the tubular portion 10, e.g., by chemical bonding, thermal bonding, sonic welding, interference fit, and the like. Thus, as shown in FIG. 2B, the sheath 30 may surround and overly the distal end 14 of the tubular portion 10 such that the lumen 16 of the tubular portion 10 communicates with the lumen 36 of the sheath 30. When the sheath 30 is compressed to the contracted condition, the proximal end 32 of the sheath 30 may be compressed against the tapered distal end 14 of the tubular portion 10.

Figure 4:
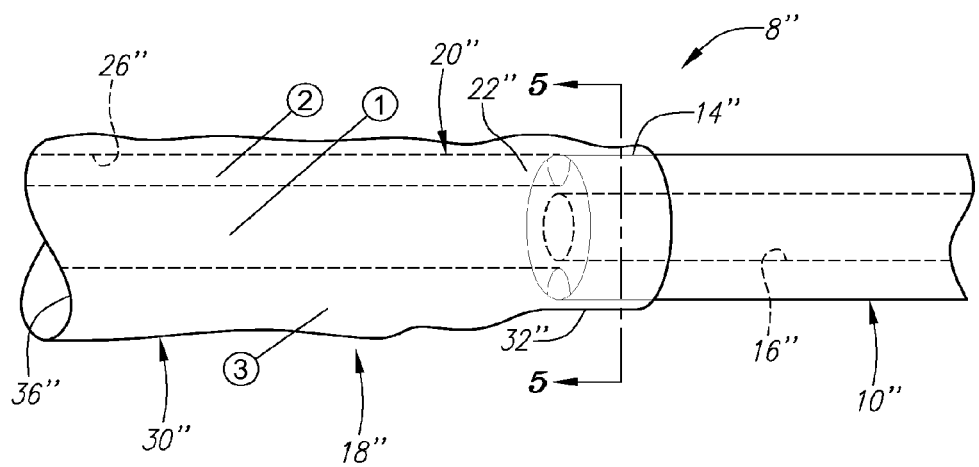
FIG. 4 is a side view of an intermediate portion of an alternative embodiment of a sheath apparatus.
Figure 5:
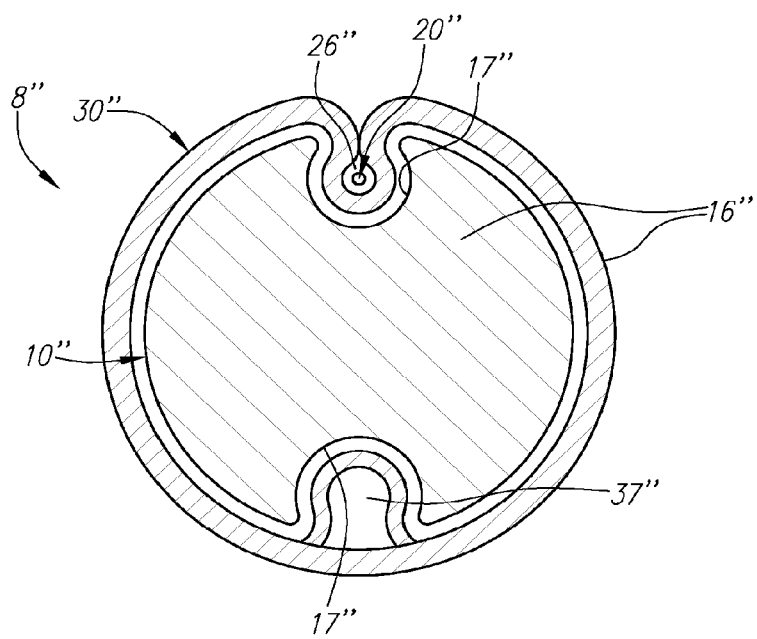
FIG. 5 is a cross-section of the apparatus of FIG. 4, taken along line 5-5.

Turning to FIGS. 4 and 5, an alternative embodiment is shown of an apparatus 8" that includes an expandable distal portion 18" extending distally from a tubular proximal portion 10." As shown, the tubular portion 10" may include a proximal end (not shown), a distal end 14," and one or more lumens extending therebetween. As shown, the tubular portion 10" includes a single lumen 16" and a pair of grooves 17" extending along the outer wall of the tubular portion 10." Alternatively, the grooves 17" may be replaced with one or more additional lumens (not shown), extending along the wall of the tubular portion 10." Unlike the previous embodiment, the distal end 14" may be substantially blunt, although alternatively, the distal end 14" may also be beveled or otherwise tapered, similar to the previous embodiments.

The expandable distal portion 18" may include a stiffening member 20" and an expandable sheath 30," similar to the previous embodiments. The stiffening member 20" may include a proximal end 22" attached to the distal end 14" of the tubular portion 18," e.g., aligned with one of the grooves 17" such that a lumen 26" within the stiffening member 20" communicates with the groove 17." A catheter, other tubular body, or cover (not shown) may be snapped into the groove 17" or otherwise attached to the tubular portion 10" to provide a lumen communicating with the stiffening member 20."

The tubular body or cover may extend at least partially towards the proximal end of the tubular portion 10," e.g., to provide a lumen for receiving a guidewire or other element therethrough. For example, the tubular body may extend entirely to the proximal end of the tubular portion 10" or to an intermediate location, e.g., to provide a rapid exchange lumen.

In addition, as best seen in FIG. 5, the sheath 30" may include a supplemental lumen 37" attached to or otherwise extending along a wall of the sheath 30," e.g., to provide a fluid-tight lumen for delivering contrast media or other fluids beyond the distal end of the sheath 30." The lumen 37" may be aligned with groove 17," which may include a tubular body or cover, similar to the other groove 17."

Returning to FIG. 1A, optionally, a proximal end 12 of the tubular proximal portion 10 may include a handle or other structure 50, e.g., that may facilitate manipulating the apparatus 80 and/or inserting one or more instruments into the lumen 16 of the tubular portion 10. In addition or alternatively, the handle 50 may include one or more valves, e.g., a hemostatic valve 52, that may substantially seal the lumen 16 from proximal flow of fluid, yet accommodate instruments being introduced into the lumen 16. In addition, the handle 50 may include one or more additional ports 54, 56 for communicating with the lumen(s) within stiffening member 20 and/or sheath 30.

Turning to FIGS. 9A-10C, an exemplary embodiment of a handle 50 is shown that includes two portions 60, 70 including wings 58 that may facilitate manipulation and/or stabilization of the handle 50. As shown, the handle 50 includes an inner member 60 and an outer member 70 that are connectable to and/or releasable from one another.

With particular reference to FIG. 10B, the inner member 60 may include a relatively short tubular section, e.g., between two and ten centimeters (2-10 cm) in length, and including a proximal end 62, a tapered distal end 64, and a lumen 66 extending therebetween. The proximal end 62 may include one or more valves, e.g., hemostatic valve 52, that may substantially seal the lumen 66, yet accommodate insertion of one or more instruments (not shown) therein. The inner member 60 may include a side port 54, e.g., including a hemostatic valve, a luer lock or other connector, and the like (not shown), that communicates with the lumen 66. A source of fluid, e.g., a syringe of saline (not shown) may be connected to the side port 54 for flushing or otherwise delivering fluid into the lumen 66 (and consequently into the lumen of the sheath 30 or other apparatus coupled to the handle 50).

Optionally, the inner member 60 may include a blade 68 adjacent the tubular section, e.g., partially embedded or otherwise attached to the outer surface of the tubular section. The blade 68 may provide a slitter for splitting or otherwise cutting the outer member 70, and/or one or more portions of the sheath 30 (or other apparatus coupled to the handle 50), as described further below.

Turning to FIG. 10A, the outer member 70 may include a tubular section including a proximal end 72, a distal end 74, and a lumen 76 extending therebetween. The outer member 70 may have a size such that the inner member 60 may be at least partially received within the lumen 76. Optionally, the outer member 70 may include a slot 78 extending distally from the proximal end 72 that may receive the wing 58 of the inner member 60 to interlock the inner and outer members 60, 70. In addition, the slot 78 may align the blade 68 with a weakened or otherwise easily cut region 79 of the outer member 70. Alternatively, similar to the embodiment shown in FIG. 15A, the outer member 70e may have a "C" shaped cross-section, including a continuous slot 78e extending between the proximal and distal ends 72e, 74e.

Returning to FIG. 10A, a stiffening member 20 may be attached to or otherwise extend distally from the outer member 70. The stiffening member 20 may be substantially permanently attached to the outer member 70, e.g., extending along an exterior surface of the outer member 70, as shown. Alternatively, the stiffening member 20 may be detachable from the outer member 70. The outer member 70 may include a side port 56 that communicates with a lumen (not shown) of the stiffening member 20. The side port 56 may include a seal and/or connector, similar to the side port 54. Alternatively, the stiffening member 20 may be connected to the distal end 74 of the outer member 70, similar to the attachments between the stiffening member 20 and proximal tubular portion 10 described above (e.g., as shown in FIGS. 2 and 4).

An expandable sheath 30 (not shown in FIG. 10A, see FIG. 9A) may be attached to or extend along the stiffening member 20. A proximal end 32 of the expandable sheath 30 may surround or otherwise be attached to the distal end 74 of the outer member 70 (e.g., similar to FIG. 1B or 4). The stiffening member 20 and expandable sheath 30 may be constructed similar to any of the other embodiments described herein. Alternatively, a proximal tubular portion (not shown) may be attached to or otherwise extend from the outer member 70, e.g., similar to the tubular portions described above, and an expandable distal portion (also not shown) may extend from the tubular portion.

As shown in FIG. 10C, the distal end 64 of the inner member 60 may be inserted into the lumen 76 from the proximal end 72 of the outer member such that the wing 58 and blade 68 are received within the slot 78 in the outer member 70, thereby assembling the handle 50. As assembled, the distal end 64 of the inner member 60 may extend a short distance beyond the distal end 74 of the outer member 70, e.g., adjacent the stiffening member 20 and/or partially into the expandable sheath 30. Receiving the wing 58 of the inner member 60 in slot 78 may limit relative movement of the inner and outer members 60, 70, e.g., while the handle 50 is being manipulated, separated, and/or while instruments (not shown) are inserted or removed from the inner member 60.

As described further below, when it is desired to remove the stiffening member 20 and expandable sheath 30, the outer member 70 may be withdrawn proximally relative to the inner member 60. This causes the blade 68 to contact the weakened or easily cut region 79 of the outer member 70, e.g., to cut through the outer member 70. As the outer member 70 is withdrawn further, the blade 68 may cut through the expandable sheath 30 (and/or the tubular proximal portion, if present), causing the expandable sheath 30 to split. Thus, the handle 50 may allow the expandable sheath 30 to be removed, while leaving the inner member 60 in place, e.g. with an instrument (not shown) maintained within the lumen 66 of the inner member 60 substantially stationary.

In alternative embodiments, other handles may be provided on the sheath apparatus 8 or any other sheath apparatus described elsewhere herein. In addition, the handle apparatus described herein may be useful for other applications, including introducer sheaths (not shown) for catheter-based procedures, and the like.

Figure 11:
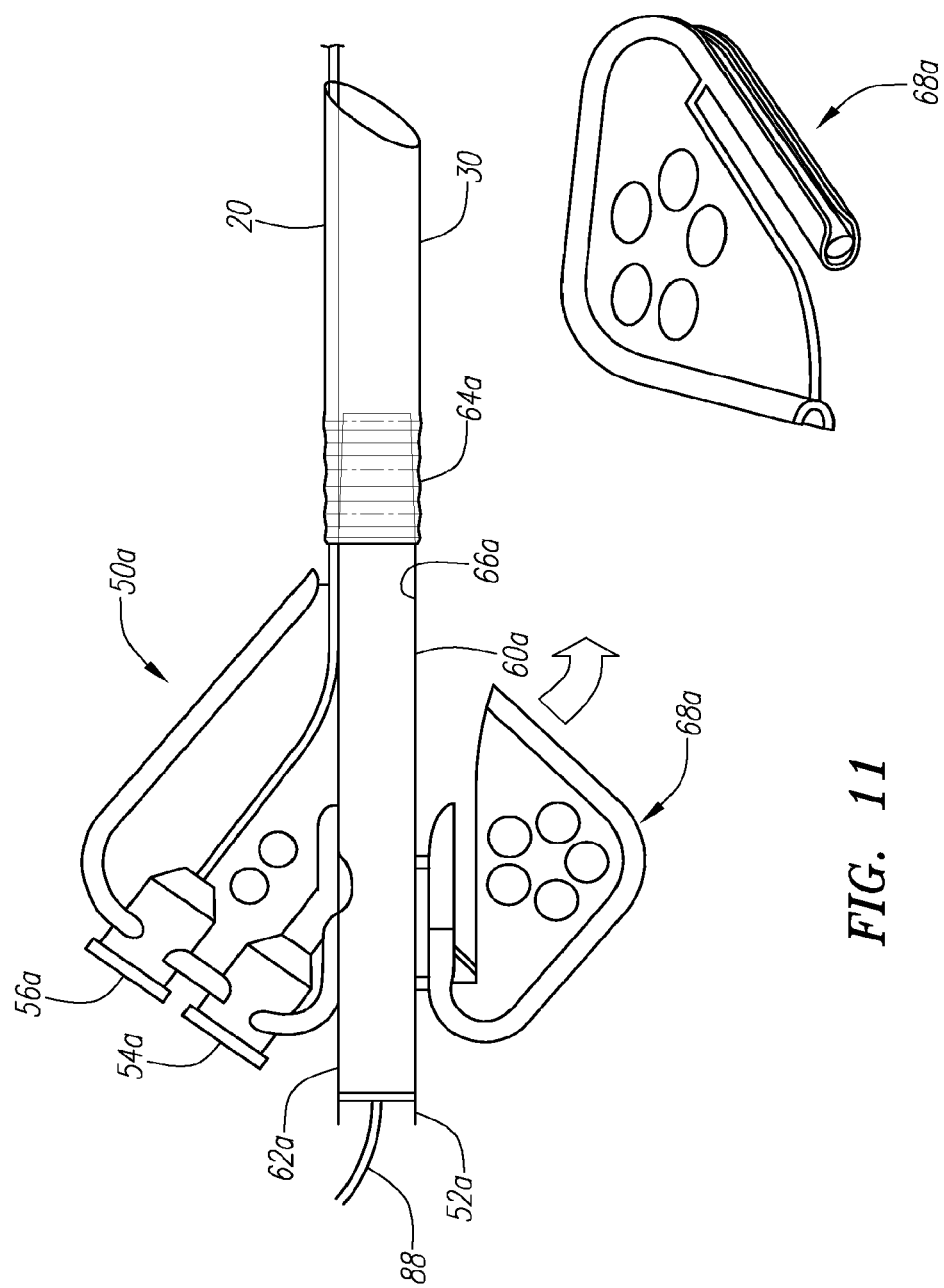
FIG. 11 is a side view of another embodiment of a handle apparatus, including a detachable slitter.

Turning to FIG. 11, a handle 50a is shown that includes a relatively short tubular section 60a, including a proximal end 62a, a distal end 64a, and a lumen 66a extending therebetween. The handle 50a may be a single piece tubular section, or may include multiple sections similar to the previous embodiment. A hemostatic valve 52a may be provided in the proximal end 62a, similar to the previous embodiment, to seal the lumen 66a while accommodating insertion of one or more instruments therein, e.g., guidewire 88. A stiffening member 20 and expandable sheath 30 may extend from the distal end 64a of the tubular section 60a, similar to the previous embodiment. In addition, the handle 50a may include a first side port 54a communicating with the lumen of the tubular section 60a (and consequently, the lumen of the expandable sheath 30), and a second side port 56a communicating with a lumen of the stiffening member 20.

Unlike the previous embodiment, the handle 50a includes a detachable slitter tool 68a that may be attached to the handle 50a, e.g., along the tubular section 60a. The slitter tool 68a may be attached by one or more tabs or other elements that may be broken, e.g., by bending the slitter 68a relative to the tubular section 60a. Once separated, the slitter 68a may be used to split or otherwise cut the tubular section 60a and/or the expandable sheath 30 similar to other embodiments described herein.

Figure 12:
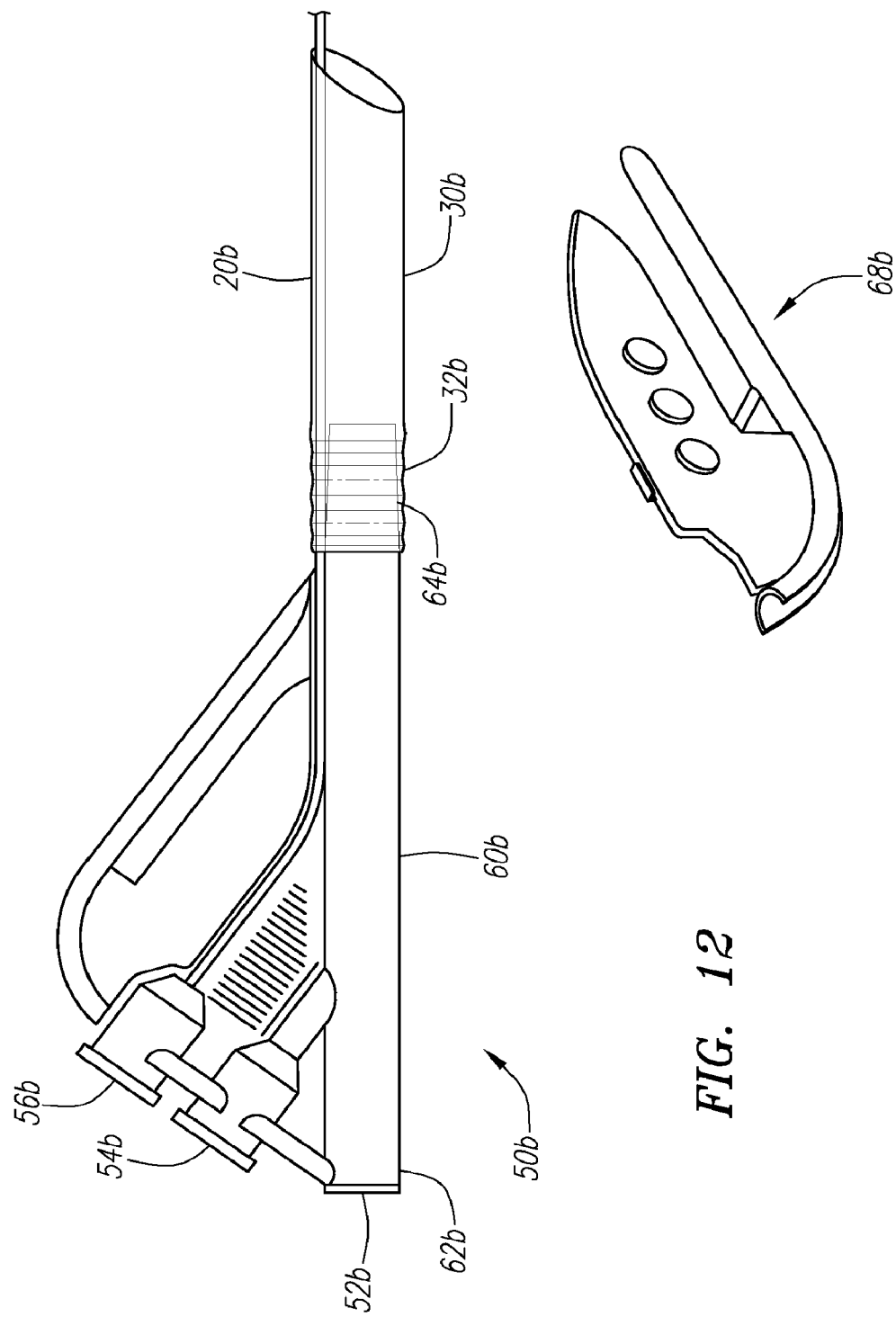
FIG. 12 is a side view of yet another embodiment of a handle apparatus, including a separate slitter.

Turning to FIG. 12, another embodiment of a handle 50b is shown that includes a separate slitter tool 68b, i.e., that is not attached to the handle 50b. Otherwise, the handle 50b may include a tubular section 60b, stiffening member 20, expandable sheath 30, and side ports 54b, 56b, similar to the previous embodiments.

Figure 13:
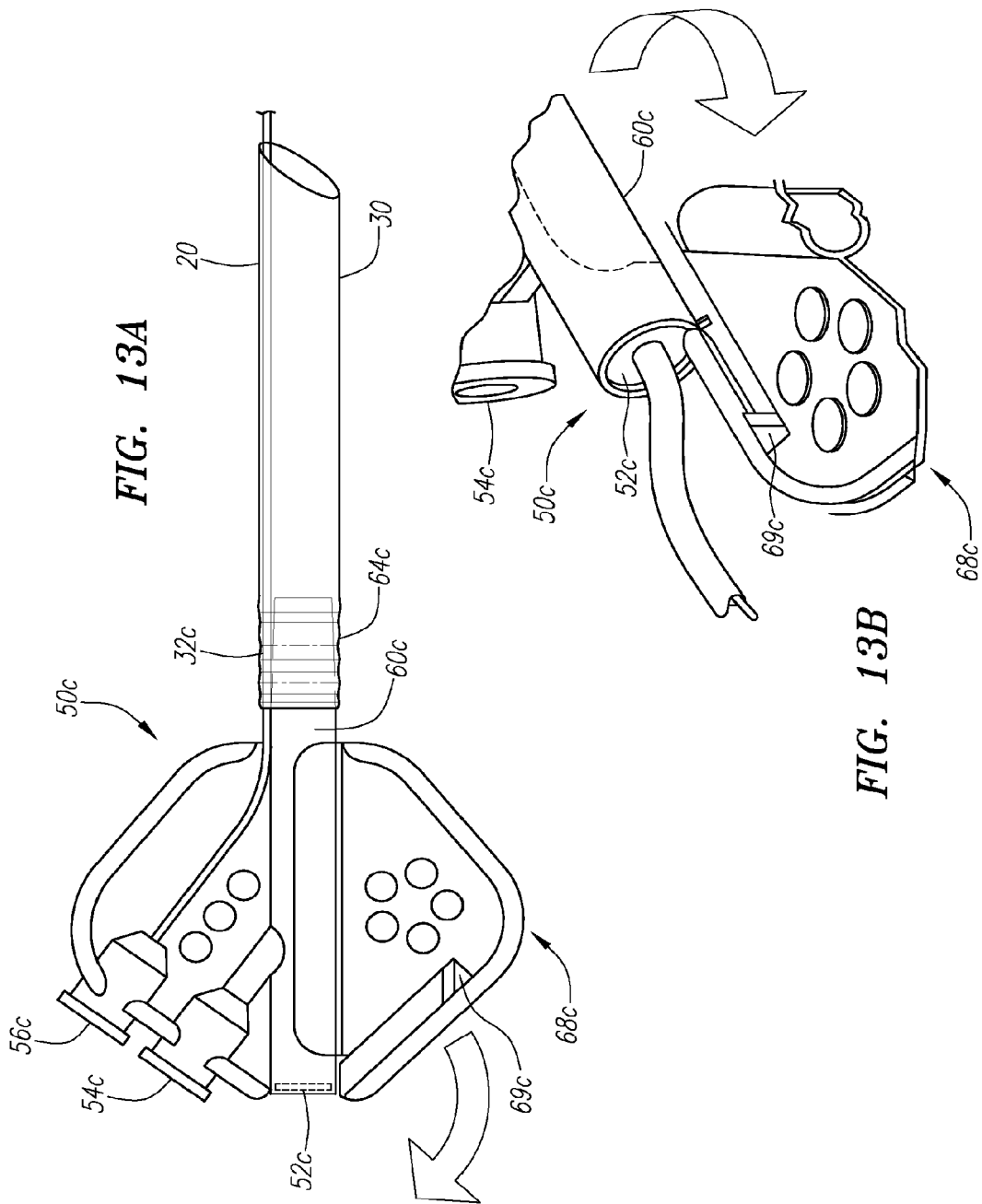
FIGS. 13A and 13B are side and perspective views, respectively, of still another embodiment of a handle apparatus including a pivotable slitter attached thereto.

Turning to FIGS. 13A and 13B, yet another embodiment of a handle 50c is shown that includes a tubular section 60c, stiffening member 20, expandable sheath 30, and side ports 54c, 56c, similar to the previous embodiments. A slitter tool 68c is attached to the tubular section 60c adjacent the seal 52c. The slitter tool 68c may be pivotally coupled to the tubular member 60c such that the slitter tool 68c may be pivoted to align a blade 69c of the slitter tool 68c with the tubular section 60c. Optionally, the tubular section 60c may include inner and outer portions (not shown), similar to the other embodiments described herein, such that the expandable sheath 30 may be split when the outer portion is withdrawn relative to the inner portion.

Figure 14:
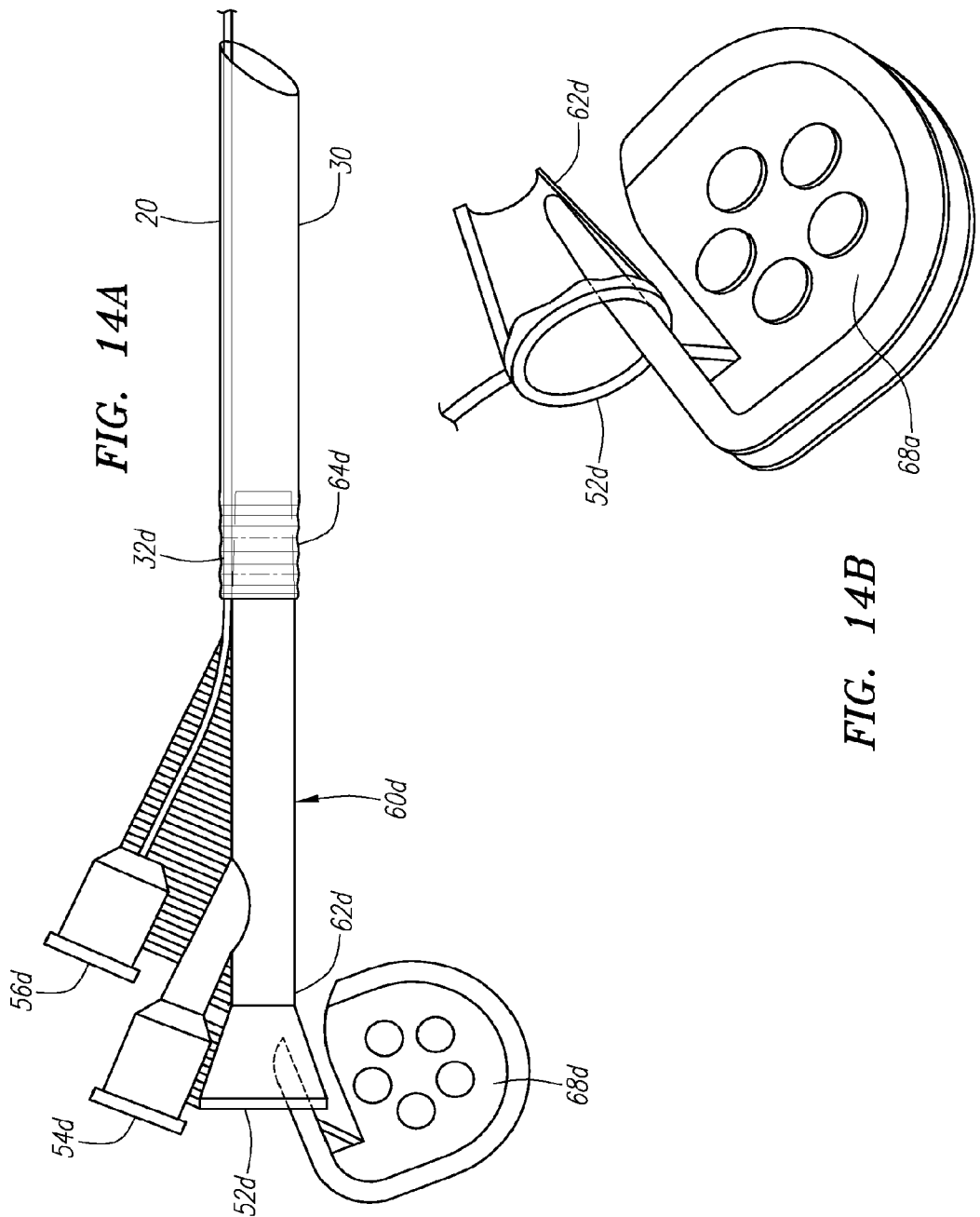
FIGS. 14A and 14B are side and perspective views, respectively, of another embodiment of a handle apparatus with an integral slitter.

Turning to FIGS. 14A and 14B, still another embodiment of a handle 50d is shown that includes a separate slitter tool 68d that may be manually inserted into a proximal end 60d of the tubular section 60d to split the tubular section 60d and the expandable sheath 30 attached thereto. The slitter tool 68d may be insertable into the seal 52d or may have a sharpened tip that may penetrate through the seal 52d to allow the tubular section 60d and sheath 30 to be split.

Figure 15:
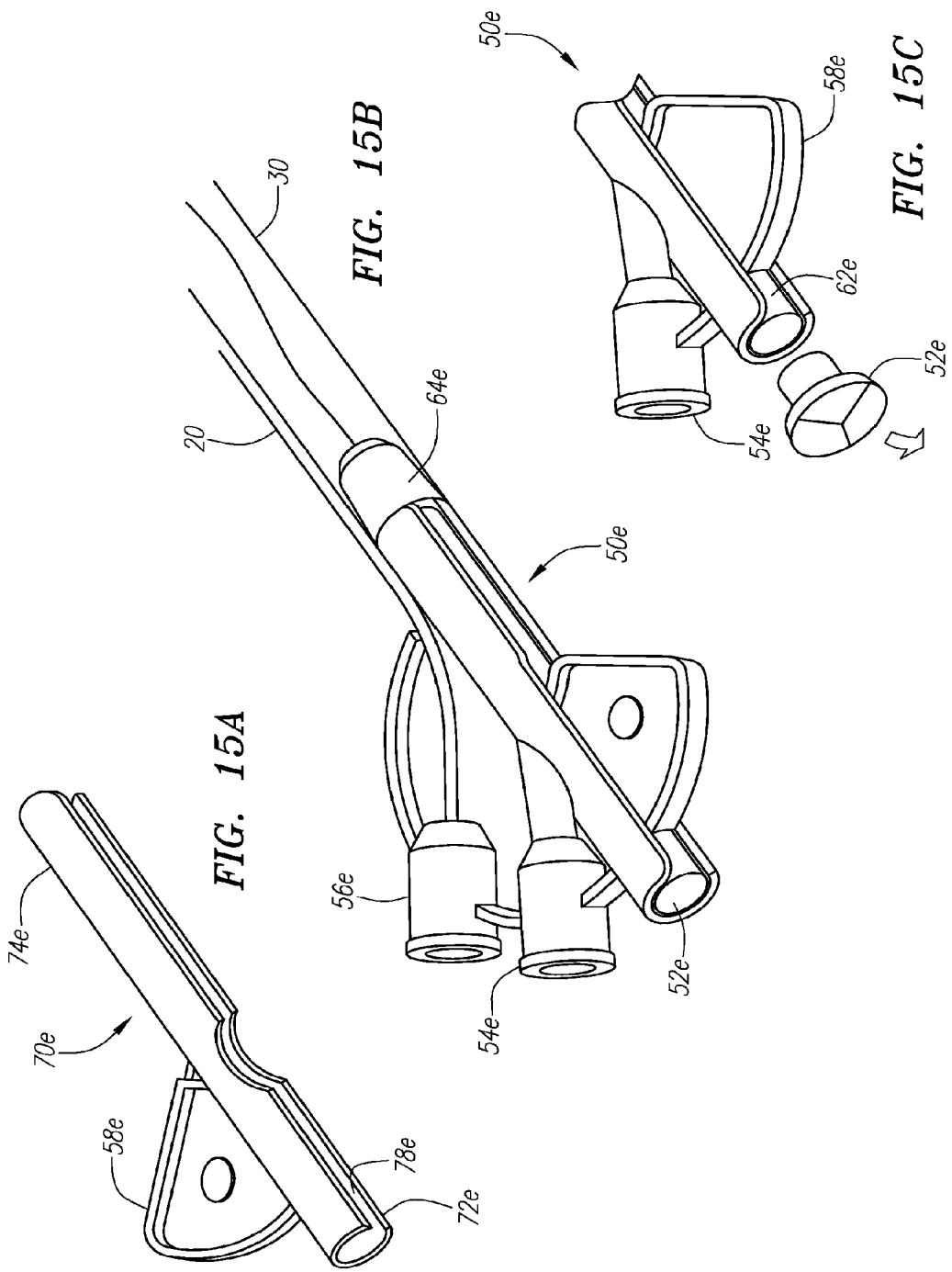
FIGS. 15A-15C are perspective views of yet another embodiment of a handle apparatus, including an outer member and an inner member slidable relative to one another.

FIGS. 15A-15C show another embodiment of a handle 50e that includes an inner member 60e and an outer member 70e. Similar to the previous embodiments, the inner member 60e may be slidably inserted into the outer member 70e such that a wing 58e of the inner member 60e is received in slot 78e in the outer member 70e. A stiffening member 20 and expandable sheath 30 may extend from the outer member 70e, similar to the previous embodiments. Unlike the previous embodiments, the hemostatic seal 52e may be removed from the inner member 60e.

Figure 16:
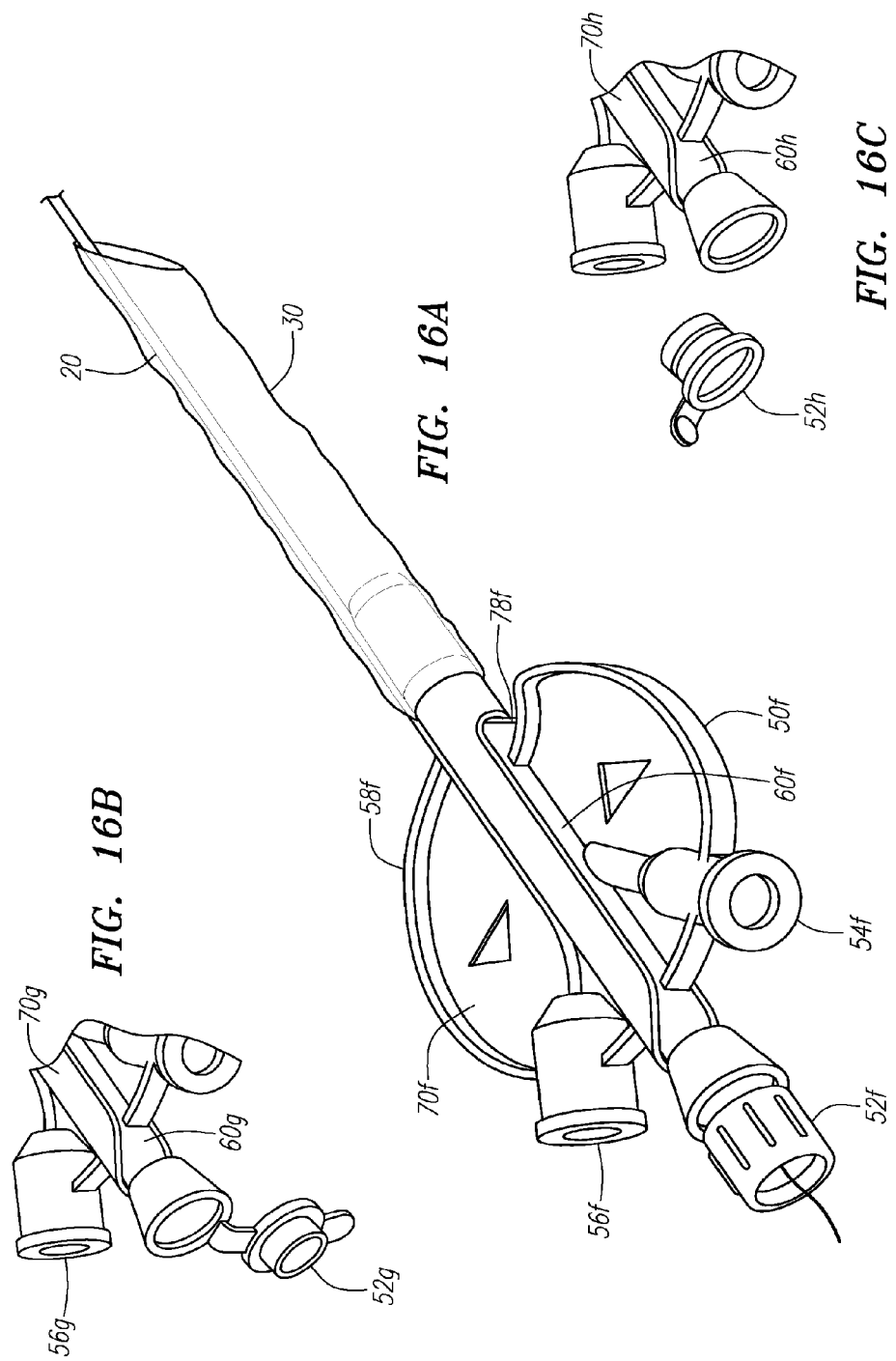
FIGS. 16A-16C are perspective views of alternative embodiments of a proximal end of a handle apparatus for a sheath apparatus.

FIGS. 16A-16C show alternative embodiments of a handle including a toughy borst valve 52f (FIG. 16A), a flip hemostatic valve 52g (FIG. 16B), and a completely removable hemostatic valve 52h (FIG. 16C). Such handles may allow the valve to be removed to facilitate using a slitter tool (not shown) to split the handle and/or sheath 30 extending therefrom.

During use, a sheath apparatus, such as apparatus 8 shown in FIG. 1A and described above (or other apparatus described herein), may be used to provide access to a vessel within a patient's body, e.g., a coronary vein. It will be appreciated that the sheath apparatus described herein may also be used to provide access to a variety of body lumens, e.g., to perform a diagnostic and/or therapeutic procedure, such as the those disclosed in application Ser. No. 10/423,321, incorporated by reference above.

Generally (with reference to FIG. 1A for illustration only), the apparatus 8, with the expandable sheath 30 in a contracted condition, may be introduced into an entry site, e.g., a natural or created opening in a patient's body, and advanced into one or more body passages, including natural or created passages within the patient's body. The apparatus 8 may be advanced from the entry site until a distal end 14 of the tubular proximal portion 10 is disposed at a first location, while the expandable distal portion 18 extends further to a second location. Because of its low profile, the expandable distal portion 18 may be easily advanced through tortuous anatomy until the distal tip 28 is disposed within relatively small, difficult to access body lumens. The tubular proximal portion 10 may provide enhanced support, e.g., to accommodate pushing one or more instruments (not shown) through the apparatus 8.

The sheath 30 may then be expanded to an enlarged condition, thereby defining a lumen 36 within the sheath 30. Thus, the apparatus 8 may provide a substantially continuous lumen, i.e., through the lumen 16 of the tubular proximal portion 10 and the lumen 36 of the sheath 30. The resulting lumen may extend continuously from the entry site through any intervening body passages to the target body lumen or site to provide a path from the entry site to the target body lumen or site.

A diagnostic and/or therapeutic procedure, such as the exemplary procedures described elsewhere herein, may be performed within the body lumen via the lumen defined by the apparatus 8. For example, one or more guidewires, catheters, leads, and the like may be advanced through the lumen provided by the apparatus 8. Upon completing the procedure(s), the apparatus 8 may be withdrawn from the body lumen, and entirely from the patient's body.

Figure 7:
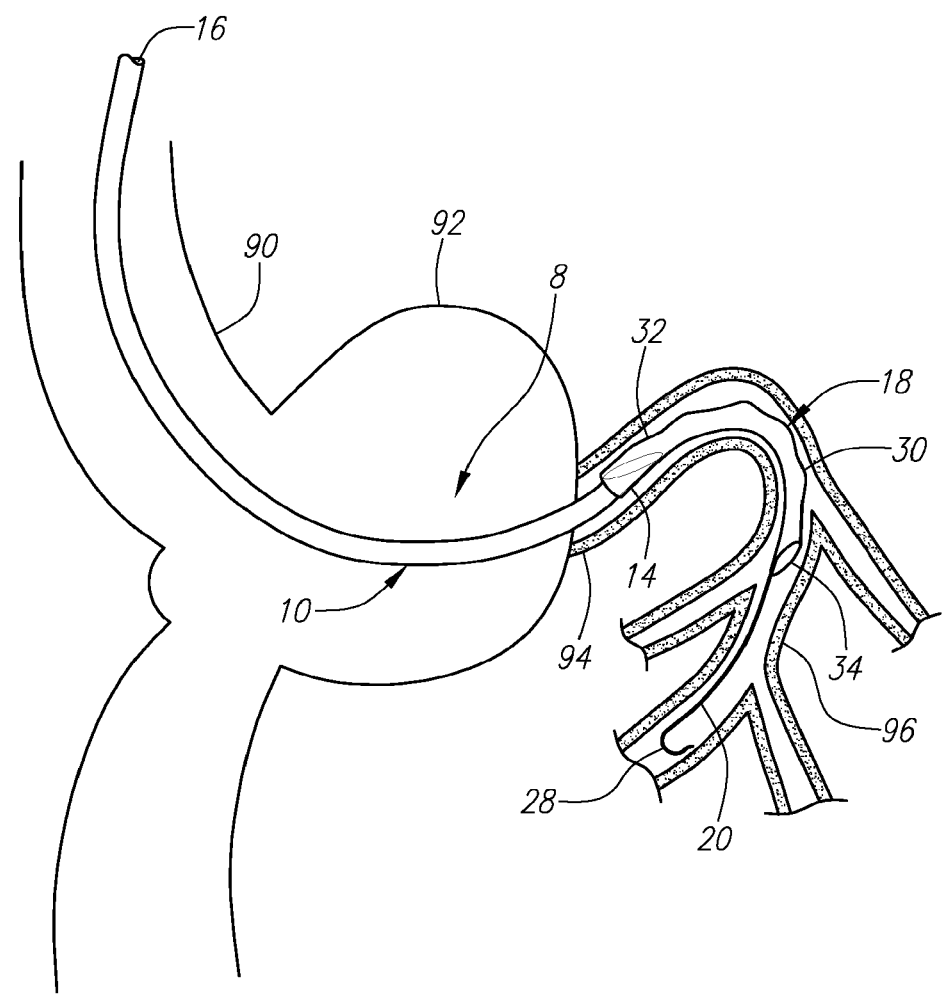
FIG. 7 is a cross-section of a patient's body, showing a method for accessing a vessel within the patient's heart using the apparatus of FIG. 1.

Turning to FIG. 7, an exemplary method is shown that uses a sheath apparatus 8 (or any of the sheath apparatus described herein) for providing access to a target vessel within a patient's vasculature. Specifically, the apparatus 8 may be used to deliver an electrical cardiac lead (not shown), e.g., for a pacemaker, into a coronary vein 96, e.g., adjacent to the left ventricle of the heart. Initially, the apparatus 8 may be advanced into the coronary vein 96 with an expandable sheath 30 carried by a stiffening member 20 in its contracted condition (not shown).

For example, with the sheath 30 collapsed, the apparatus 8 may be introduced from a percutaneous entry site, e.g., a femoral vein or subclavian vein (not shown), and advanced through the patient's venous system into the vena cava 90, the right atrium 92 of the heart, and finally into the coronary sinus 94 to reach the target coronary vein 96. The apparatus 8 may be advanced over a guidewire (not shown), e.g., by placing the guidewire along the desired path to the coronary vein 96 using conventional methods. Exemplary apparatus and methods for accessing the coronary sinus 94 to deliver the apparatus 8 are disclosed in U.S. Pat. No. 6,959,290, issued Dec. 27, 2005, the entire disclosure of which is expressly incorporated herein by reference.

Because of the relatively low profile of the expandable distal portion 18 with the sheath 30 collapsed (which is substantially the size of the stiffening member 20), the apparatus 8 may be able to access smaller coronary veins or be advanced further into a target coronary vein than the tubular proximal portion 10 or conventional access sheaths.

Thus, the distal portion 18 with the sheath 30 collapsed may be advanced first from the percutaneous site into the right atrium 92 and coronary sinus 94. As the apparatus 8 is advanced further, the distal tip 28 of the distal portion 18 may be introduced into the target vein 96. As this occurs, the proximal portion 10 may pass through the vena cava 90 and into the right atrium 92, or even the coronary sinus 94, as shown. Because the proximal portion 10 may only pass through larger, less tortuous vessels, the larger profile may not impair advancement of the apparatus 8 to place the distal tip within the target vein 96.

If the distal portion 10 has a tapered distal end 14, the distal end 14 may also provide a transition to facilitate the tubular portion 10 following the smaller distal portion 18. In addition or alternatively, as shown in FIG. 20, an obturator 40 may be provided within the apparatus 8 to facilitate advancing the proximal portion 10 after the distal portion 18. Once the proximal portion 10 is adequately positioned, e.g., within the right atrium 92 or coronary sinus 94, the obturator 40 may be removed.

Once the apparatus 8 is positioned with the expandable distal portion 18 in or near the target vein 96, fluoroscopy and/or other external imaging may be used to facilitate positioning the apparatus 8. Optionally, the apparatus 8 may include one or more radiopaque markers, e.g., on the distal end 24 of the stiffening member 20, the distal end 34 of the sheath 30, and/or the distal end 14 of the proximal tubular portion 10, to facilitate such imaging. In addition or alternatively, contrast may be introduced into the vein, e.g., via a fluid lumen in the stiffening member 20 of the apparatus 8 and/or through the lumen 34 of the sheath 30, to facilitate fluoroscopic imaging. Such imaging may be used to identify the location of the sheath 30 relative to nearby structures, e.g., to ensure that the apparatus 8 is advanced as close as possible to a target location. In the exemplary embodiment shown in FIG. 7, the apparatus 8 is advanced such that the distal end 34 of the sheath 30 is disposed within a coronary vein 96 adjacent the left ventricle of the patient's heart.

The expandable sheath 30 may then be expanded between the distal end 14 of the proximal tubular portion 10 and the target vein 96. A fluid, e.g., including saline and/or contrast, may be introduced into the sheath 30 to expand the sheath 30 towards its enlarged condition. Contrast delivered into the sheath 30 may also facilitate imaging the vein 96. In addition or alternatively, an instrument (not shown) may be advanced through the apparatus 8 to expand the sheath 30.

An electrical pacing lead (not shown) and/or other instrument may then be advanced through the proximal tubular portion 10 and the sheath 30 (which may expand or further expand the sheath 30) until the lead is disposed within the vein 96 beyond the distal tip 28. Because cardiac leads are extremely flexible or floppy, the relative strength and/or rigidity of the proximal portion 10 may facilitate advancing the lead through larger vessels, where the lead may otherwise wander or bind up. As the lead enters the sheath 30, the sheath 30 may provide a lubricious interface between the lead and the surrounding vessel wall, which may facilitate advancing the lead deeper into the patient's vasculature.

Once the lead is delivered, the apparatus 8 may be removed. For example, as described above, a handle, such as handle 50 described above (not shown in FIG. 7, see FIGS. 9-10C), may be provided that includes an inner member 60 and an outer member 70 to which the tubular proximal portion 10 is attached. In this embodiment, the cardiac lead may be advanced into the inner member 60 through the valve 52, and, consequently, into the proximal portion 10 and sheath 30.

To remove the apparatus 8, the outer member 70 may be retracted proximally, thereby withdrawing the tubular proximal portion 10, as well as the distal portion 18 (i.e., the stiffening member 20 and sheath 30), proximally from the patient's body. As the sheath 30 is removed from the percutaneous site, the sheath 30 may be split, e.g., by a blade 78 or other slitter tool (not shown) on the inner member 60.

While the outer member 70, tubular proximal portion 10 and expandable distal portion 18 are removed, the inner member 60 may be maintained substantially stationary, thereby maintaining the end of the lead within the target vein 96. Once the tubular proximal portion 10 and sheath 30 are removed from the patient, the inner member 60 may also be removed, while maintaining the lead substantially stationary. Because the inner member 60 has a relatively short length, the inner member 60 may be removed more easily with reduced risk of displacement of the lead, thereby ensuring that the lead remains within the target vein 96.

Figure 8A:
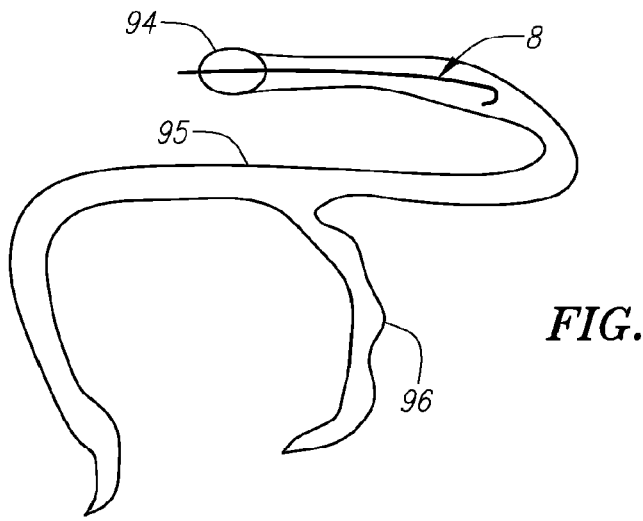
FIGS. 8A-8J are cross-sections of a patient's body, showing a method for delivering a cardiac lead into a coronary vein within a patient's heart.
Figure 8B:
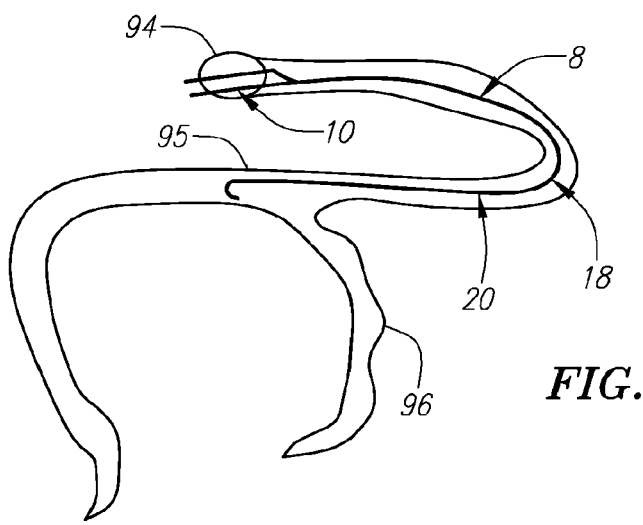
Figure 8C:
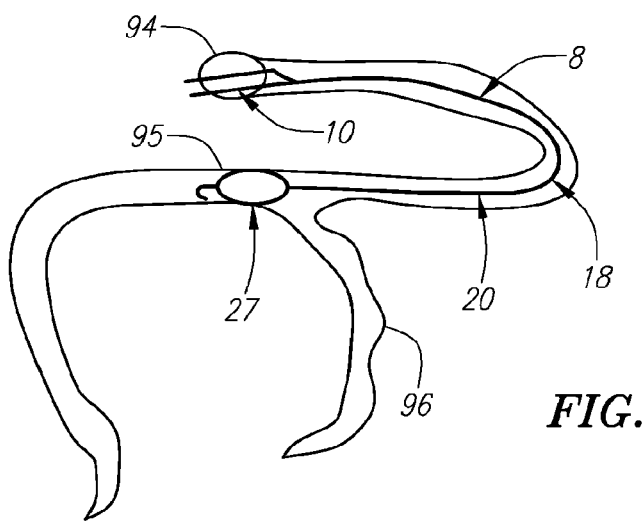

Turning to FIGS. 8A-8J, another method is shown for delivering an electrical pacing lead 100 into a coronary vein 96, e.g., through the right atrium (not shown) and coronary sinus 94 of the heart, similar to the previous embodiment. This method may be particularly useful for delivering a lead into a target vein 96 that is difficult to access, e.g., if it branches acutely from an adjacent vessel 95. Initially, as shown in FIGS. 8A-8C, an apparatus 8 may be introduced through the coronary sinus 94 into the vessel 95 adjacent the target vein 96. Generally, the apparatus 8 includes a tubular proximal portion 10, and an expandable distal portion 18, similar to the previous embodiments. The distal portion 18 includes a pushable stiffening member 20 carrying a balloon 27 or other expandable occlusion member and an expandable sheath 30.

As shown in FIGS. 8A and 8B, the apparatus 8 may be advanced into the vessel 95 with the sheath 30 and balloon 27 initially collapsed. The apparatus 8 may be advanced over a guidewire or other rail (not shown). Optionally, contrast and the like may delivered via a lumen in the stiffening member 20 to facilitate fluoroscopic imaging of the patient's vasculature, e.g., to facilitate advancing the apparatus 8, and/or positioning the balloon 27 distally to the target vein 96. Alternatively, the balloon 27 may be provided on a separate catheter or other balloon device (not shown), and the apparatus 8 may be advanced over the balloon device.

As shown in FIG. 8C, once the balloon 27 is positioned at a desired location, e.g., immediately distal to the target vein 96, the balloon 104 may be expanded to at least partially occlude the vessel 95 and/or to substantially seal the vessel 95 distal to the target vein 96 (e.g., if additional contrast delivery is desired for fluoroscopic imaging). In addition, the balloon 27 may substantially anchor the stiffening member 20 relative to the target vein. As shown in FIG. 8C, the tubular proximal portion 10 may be sufficiently long to enter the coronary sinus 94 when the balloon 27 is positioned adjacent the target vein 96.

Figure 8D:
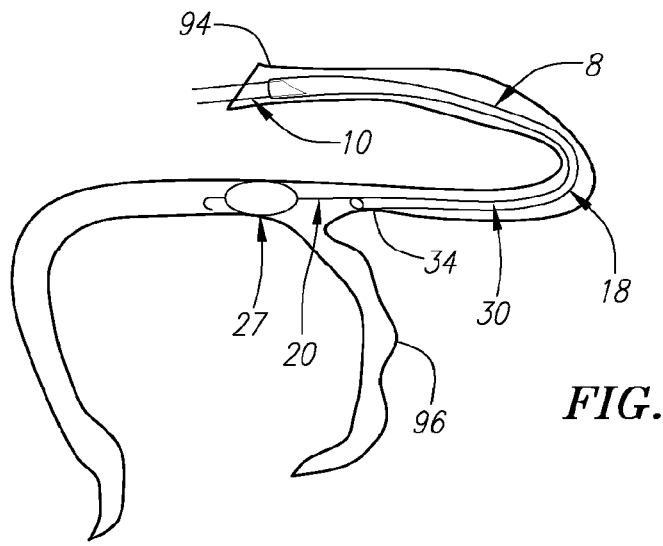

Turning to FIG. 8D, once the balloon 27 is positioned and expanded to occlude the vessel 95 and/or anchor the stiffening member 20, the sheath 30 may be expanded, if desired. Alternatively, the sheath 30 may remain collapsed (but may be released from any constraints) until the lead 100 is advanced into the sheath 30. In a further, alternative, the sheath 30 may be expanded before the balloon 27 is expanded.

Figure 8E:
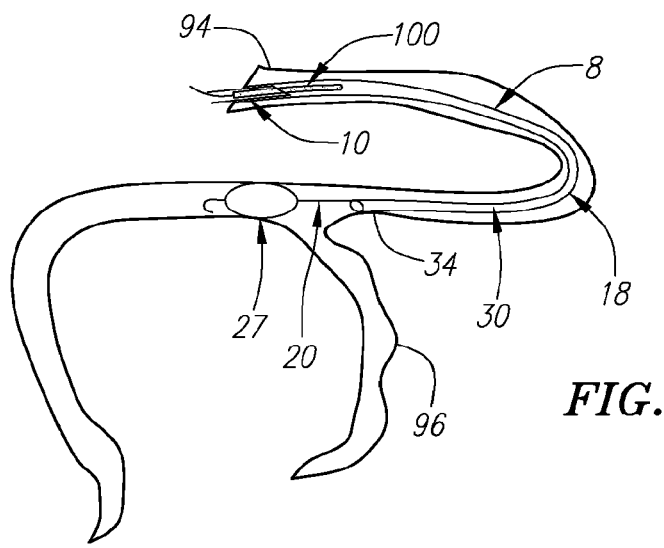
Figure 8F:
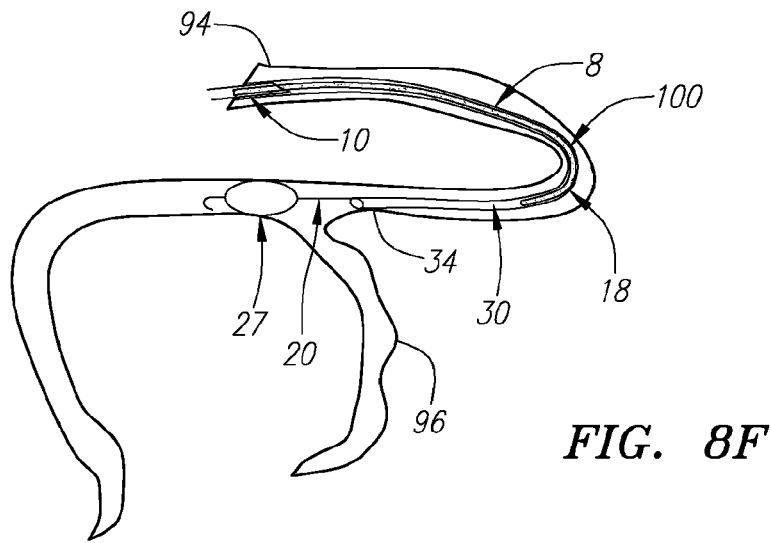

Turning to FIGS. 8E-8H, a lead 100 may then be advanced through the apparatus 8 into the target vein 96. For example, the lead 100 may be inserted through a valve 52 of a handle 50 on a proximal end 12 (all not shown, see, e.g., FIG. 1A) of the apparatus 8 into the tubular proximal portion 10 and advanced until the lead 100 enters the expandable distal portion 18, as shown in FIG. 8E. As the lead 100 is advanced further, the sheath 30 may expand or otherwise accommodate guiding the lead 100 through the coronary veins into vessel 95, as shown in FIGS. 8E and 8F.

Figure 8G:
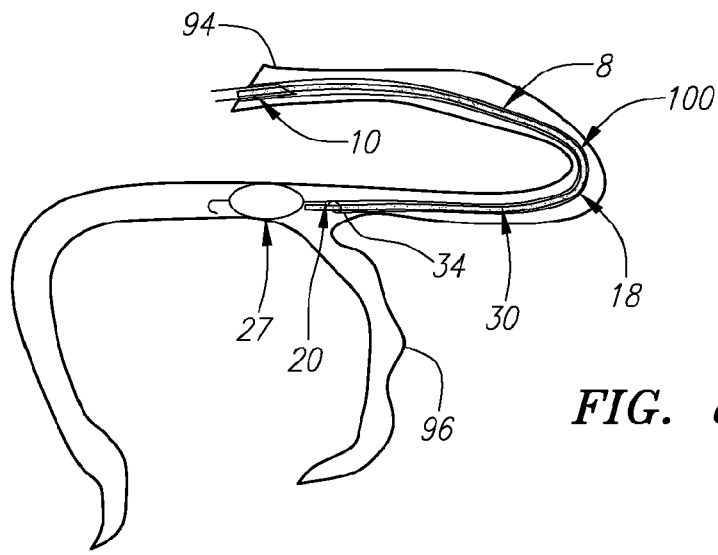
Figure 8H:
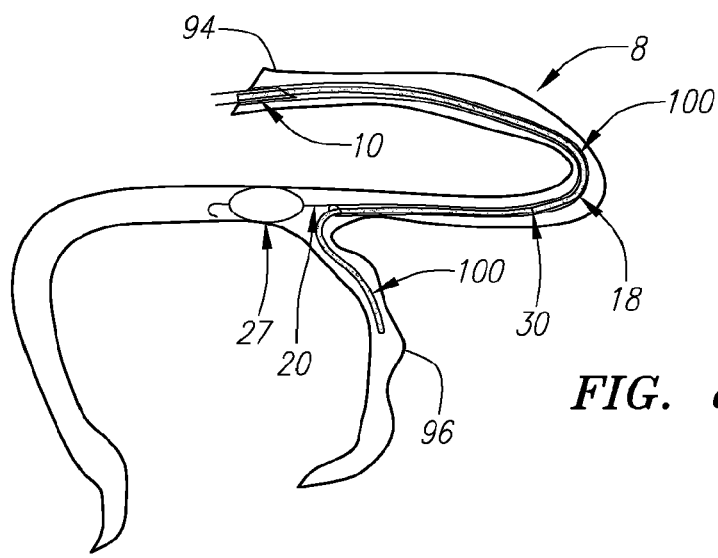

Turning to FIG. 8G, the lead 100 may eventually exit from the distal end 34 of the sheath 30 and become exposed within the vessel 95. As the lead 100 is advanced further, the lead 100 may contact the balloon 27. Because the balloon 27 substantially occludes the vessel 95 distal to the target vein 96, as the lead 100 is advanced further, the only available path is into the target vein 96. Thus, the balloon 27 may assist in redirecting the lead 100 into a target vein 96 that may otherwise be difficult to access, as shown in FIG. 8H.

Figure 8I:
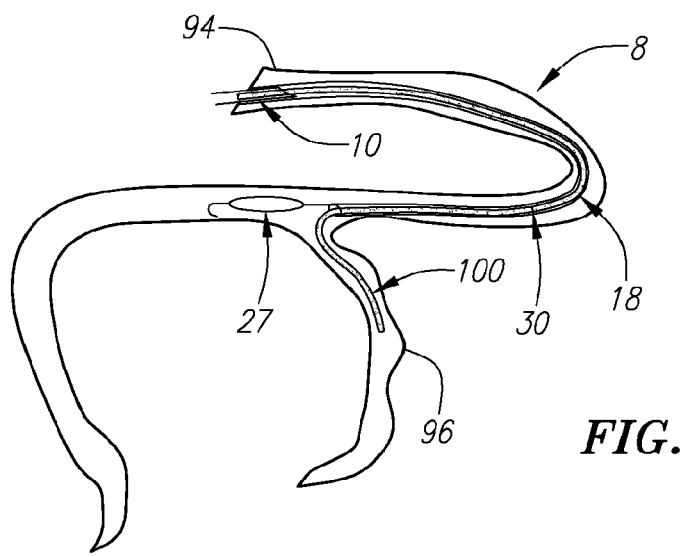
Figure 8J:
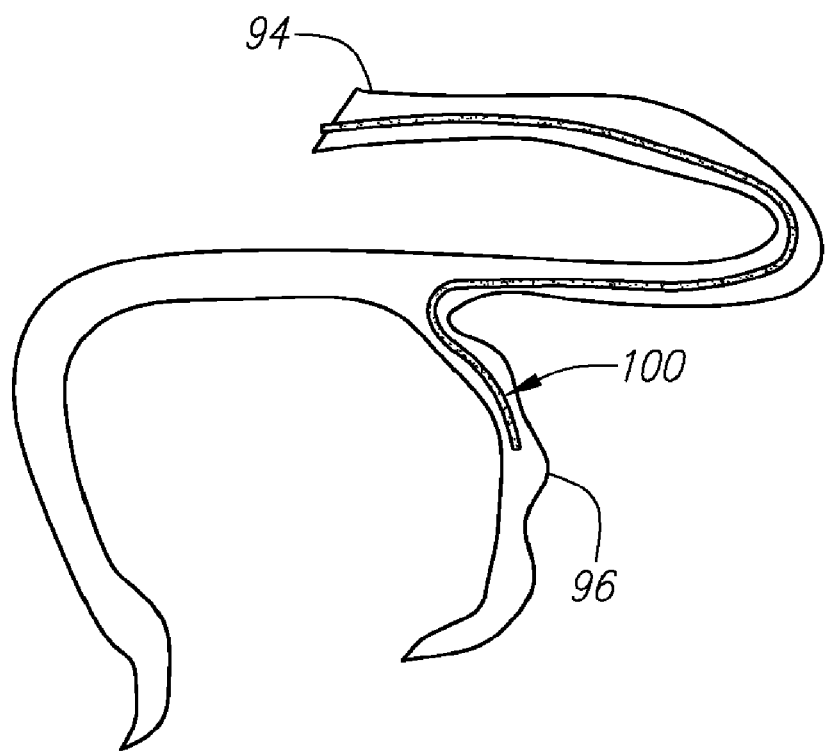
Figures 9A, 9B:
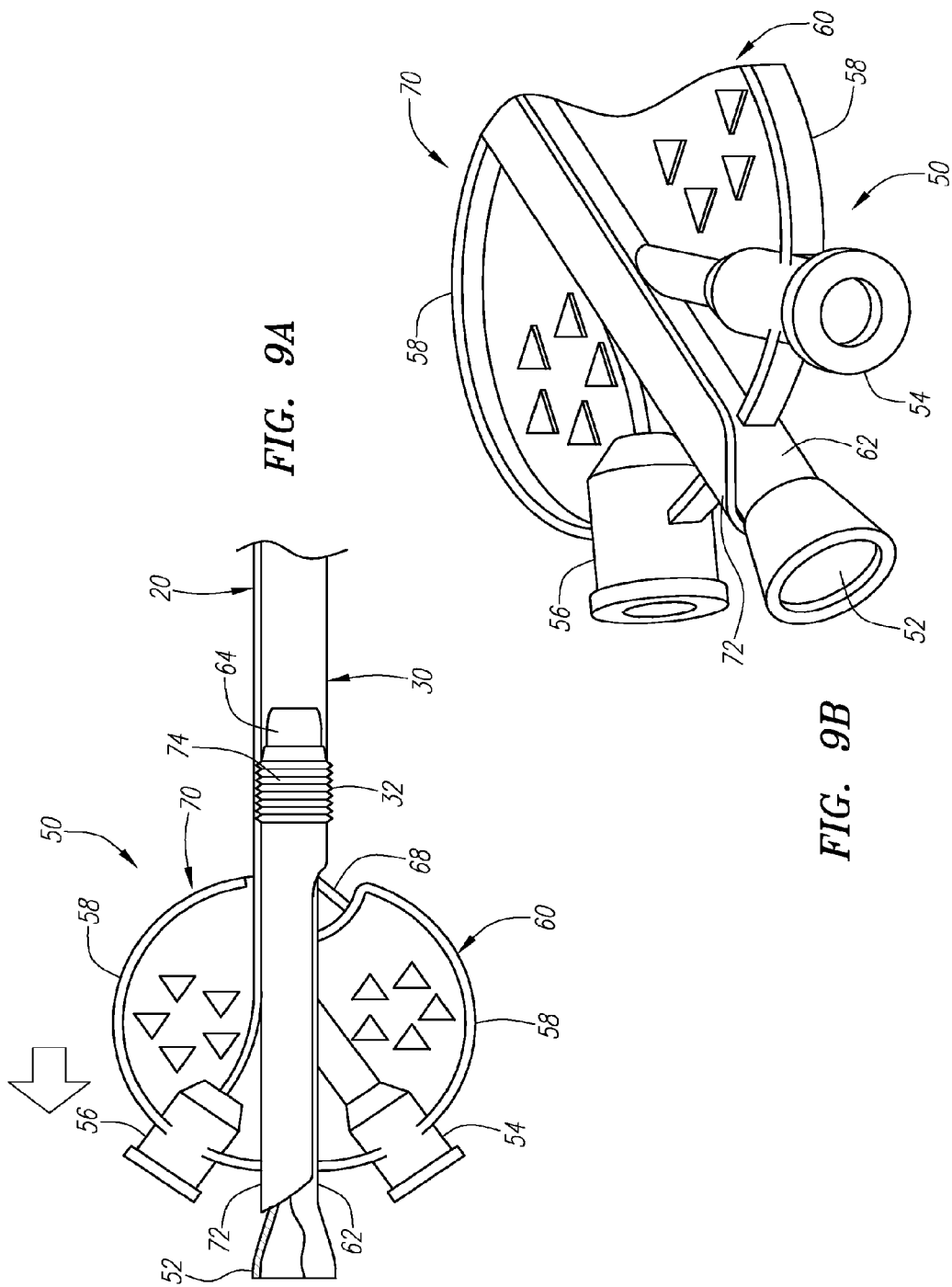
FIGS. 9A and 9B are side and perspective views, respectively, of a handle apparatus that may be provided on a proximal end of a sheath apparatus.

Turning to FIG. 8I, once the lead 100 is positioned in the target vein 96, the balloon 27 may be deflated or otherwise collapsed, and the apparatus 8 may be withdrawn from the vessel 95, the coronary sinus 94, and ultimately out of the patient's body. As shown in FIG. 8J, the lead 100 may remain implanted within the target vein 96 (or further down another branch, if desired). Implantation of the lead 70 may then be completed, e.g., including connecting the proximal end to a pacemaker and the like (not shown), using conventional methods.

Figure 19A:
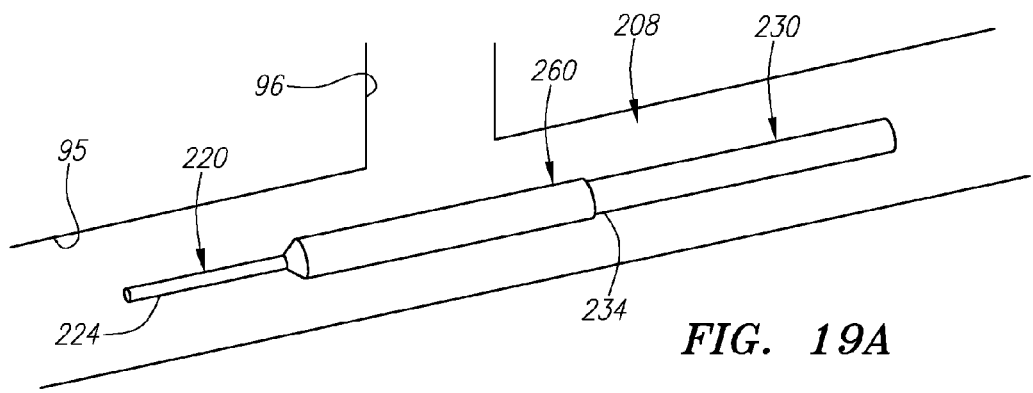
FIGS. 19A-19C are cross-sectional views of a patient's body, showing a method for delivering a lead into a branch vessel from a main vessel.
Figure 19B:
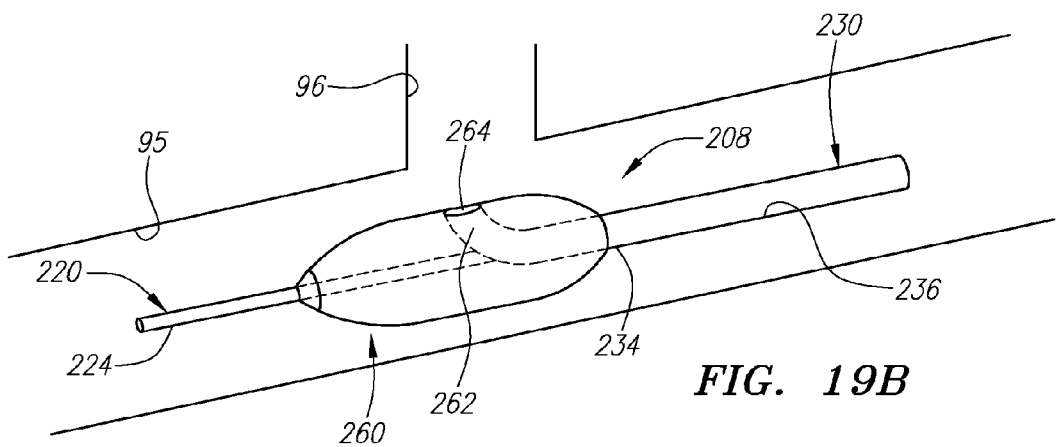
Figure 19C:
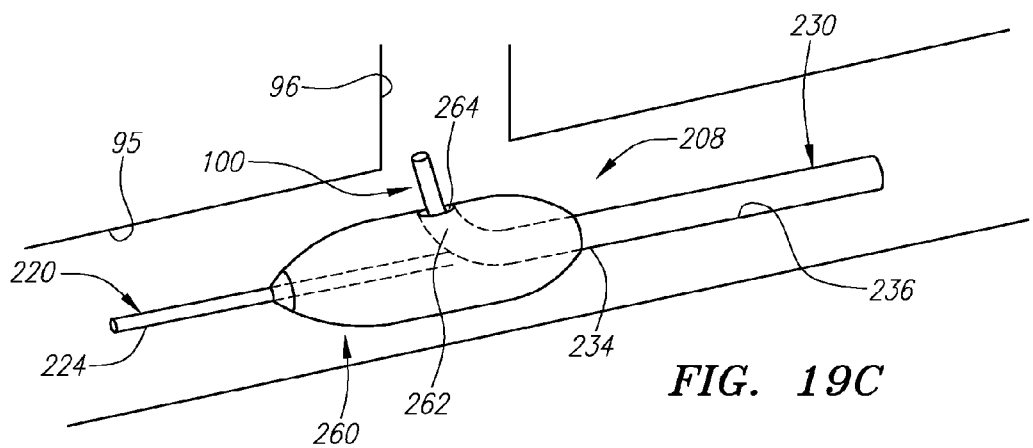

Turning to FIGS. 19A-19C, in an alternative embodiment, an expandable sheath apparatus 208 may be provided that includes a stiffening member 220 and an expandable sheath 230, similar to the other embodiments described herein. Optionally, the apparatus 208 may include one or more of a tubular proximal portion, a handle, and the like (all not shown), also similar to the embodiments described above.

Unlike the previous embodiments, the apparatus 208 includes a balloon or other expandable member 260 on a distal end 234 of the sheath 230. The stiffening member 220 or sheath 230 may include a lumen (not shown) that communicates with an interior of the balloon 260, for delivering inflation media into the balloon 260 from a proximal end (not shown) of the apparatus 208. Thus, the balloon 260 may be expanded or collapsed by delivering or evacuating fluid into and out of the balloon 260.

As best seen in FIG. 19B, the balloon 260 includes a passage 262 therethrough that communicates with a lumen 236 of the sheath 230. As shown, the passage 260 includes a bend that terminates in a transverse opening 264 in an outer wall of the balloon 260. As shown, the passage 260 extends substantially perpendicular to the stiffening member 220, although it will be appreciated that the passage 260 and opening 264 may provide any desired lateral or other transverse orientation.

The apparatus 208 may be used for delivering a lead 100, similar to the previous embodiments. For example, as shown in FIG. 19A, with the sheath 230 and balloon 260 collapsed, the apparatus 8 may be advanced into a vessel 95 until the balloon 260 is disposed adjacent to a target vessel 96. Once properly positioned, the balloon 260 may be expanded, e.g., to open the passage 262 and/or to anchor the apparatus 208 relative to the vessel 95. As best seen in FIG. 19B, the balloon 208 is preferably expanded with the opening 264 disposed in alignment with the target vessel 96.

Thereafter, as shown in FIG. 19C, a lead 100 may be advanced through the apparatus 208, i.e., through the lumen 236 of the sheath 230 until the lead 236 enters the passage 262. Because of the floppy structure of the lead 100 and/or the radius of the passage 262, the lead 100 may be advanced through the passage 262, out the opening 264, and into the target vessel 96. The lead 100 may then be implanted within the target vessel 96 or otherwise further manipulated, as desired. Once the lead 100 is positioned at a desired implantation site, the balloon 260 may be collapsed, and the apparatus 208 may be removed from the vessel 95 and out of the patient's body.

Figure 17:
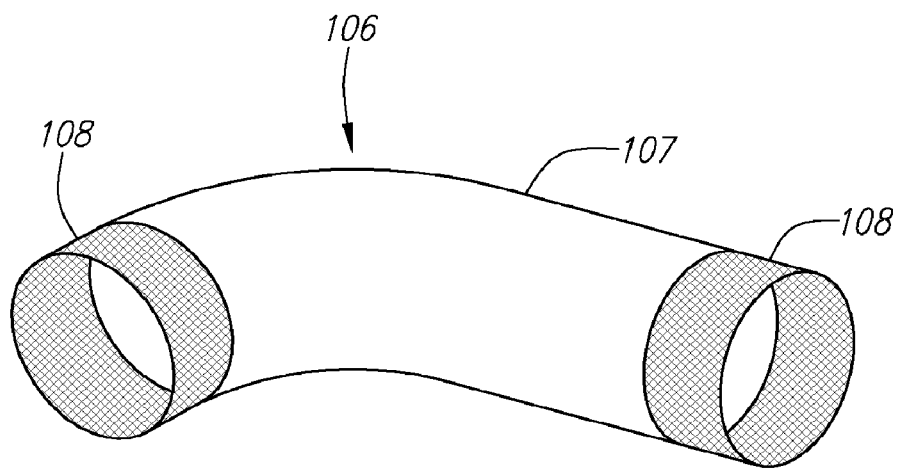
FIG. 17 is a perspective view of a protective sleeve that may be carried by a cardiac lead.

Turning to FIGS. 17 and 18A-18C, a thin sleeve 106 is shown that may be delivered in conjunction with a lead 100, e.g., a cardiac pacing lead. As best seen in FIG. 17, the sleeve 106 may include a tubular section 107 and a stent-like structure 108 on one or both ends of the tubular section 107. It will be appreciated that any self-expanding or balloon-expandable stent structures may be provided on the ends of the tubular section 107.

Figure 18A:
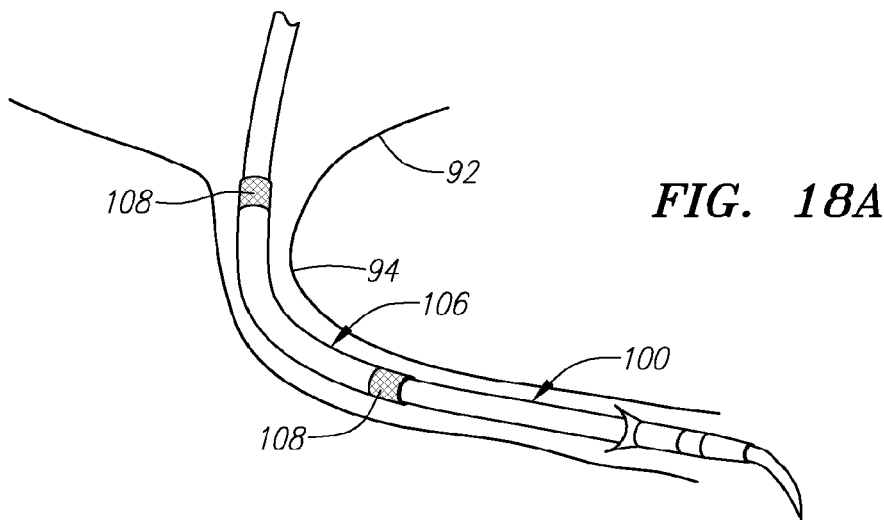
FIGS. 18A-18C are cross-sectional views of a patient's body, showing a method for delivering and removing a removable cardiac lead into the patient's heart that includes the protective sleeve of FIG. 17.

Turning to FIG. 18A, in one embodiment, the thin sleeve 106 may be provided on an exterior of a lead 100, e.g., at an intermediate location on the lead 100. Otherwise, the lead 100 may be of conventional, known construction. The lead 100, carrying the sleeve 106, may be delivered into a patient's body, e.g., through the right atrium 92, the coronary sinus 94, and into the coronary veins (not shown). Preferably, the sleeve 106 is provided at a predetermined intermediate location on the lead 110, such that, when a tip of the lead is delivered into a target vein, the sleeve 106 is disposed within the coronary sinus 96, as shown in FIG. 18A. The lead 100 may be delivered using the apparatus and methods described herein, or using conventional methods.

Generally, after a lead, such as lead 100, is implanted, the wall of the coronary sinus may fibrose or otherwise attach to the lead 100. Because the sleeve 106 is disposed around the lead 100, any tissue fibrosis may attach to the sleeve 106, rather than to the lead 100 itself. Thereafter, if it is desired to remove or move the lead 100 (e.g., as often becomes necessary over time as the heart remodels itself to CRT therapy), the lead 100 may be manipulated or even removed, while the sleeve 106 remains in place. Without the sleeve 106, if the lead 100 is removed or otherwise moved, there is a substantial risk that the wall of the coronary sinus may rupture or otherwise be damaged due to the tissue fibrosis, requiring acute treatment of the patient.

Figure 18B:
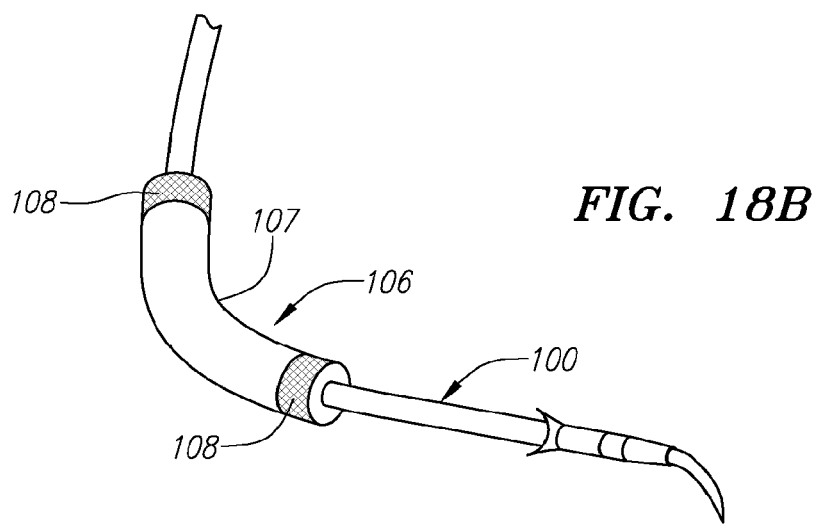
Figure 18C:
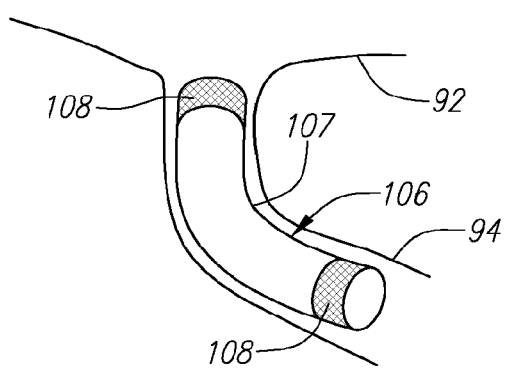

Optionally, as shown in FIG. 18B, a balloon device may be used to expand the thin sleeve 106, e.g., to plastically expand the stents 108 into engagement with the surrounding tissue of the coronary sinus 96. Alternatively, an overlying sleeve or other constraint may be used to hold the thin sleeve 106, such that, when the constraint is removed, the thin sleeve 106 may resiliently expand to engage the tissue of the coronary sinus 96.

Such a balloon or constraint may be provided on the lead 100 or on an apparatus (not shown) used to deliver the lead 100, e.g., on an exterior of a proximal portion of any of the apparatus described herein. Alternatively, the thin sleeve 106 may be delivered independently, e.g., before the lead 100 is delivered through the coronary sinus 96.

In other alternatives, the lead may include a drug or other material embedded within or otherwise carried by the lead that may prevent or minimize tissue fibrosis to the lead. In addition or alternatively, the outer surface of the lead may be treated, e.g., by micro-texturing that may prevent surrounding tissue from binding to the lead.

Turning to FIGS. 24A and 24B, another embodiment of an expandable sheath apparatus 109 is shown that includes an elongate stiffening member 120 having a proximal end 122 and a distal end 124. The apparatus 109 further includes a flexible sheath 130 affixed or otherwise secured to the elongate stiffening member 130 along its length. The flexible sheath 130 is shown in a collapsed state in FIG. 24A, and is shown in an expanded or partially expanded state in FIG. 24B.

The flexible sheath 130 may be affixed or otherwise secured to the elongate stiffening member 120 using any number of configurations. FIGS. 25-31 are cross-sectional views of alternative embodiments of the apparatus 109, taken along the line A-A shown in FIG. 24A.

FIG. 25 illustrates a cross-sectional view of the distal portion of the apparatus 109 illustrating one embodiment of securing the elongate stiffening member 120 to the sheath 130. In this embodiment, the elongate stiffening member 120 is external to the lumen of the sheath 130. The elongate stiffening member 120 is slit along its length to form a slot 120(a). A portion of the flexible sheath 30 is then inserted into the slot 120(a) and into the interior lumen 120(b) of the elongate stiffening member 120. The portion of the flexible sheath 130 inside the elongate stiffening member 120 may then be affixed or otherwise bonded to the internal surface 120(c) of the elongate stiffening member 120.

In an alternative embodiment, a secondary tube 121 may be inserted through the lumen 120(b) of the elongate stiffening member 120 such that the sheath 130 is sandwiched between the exterior of the secondary tube 121 and the internal surface 120(c) of the elongate stiffening member 120. A mechanical junction is formed between elongate stiffening member 120 and the flexible sheath 130. This structure is particularly advantageous for materials that are difficult to heat or chemically bond, such as fluoropolymers. For example, the elongate stiffening member 120 and secondary tube 121 may be constructed out of a polymer material that reflows with heat (e.g., ePTFE) or a material coated with flowable polymer material. A mechanical lock may be achieved between the elongate stiffening member 120 and secondary tube 121 upon the reflowing of polymer material through the pores of the ePTFE within the sheath 130.

FIG. 26 is a cross-sectional view of the distal portion of the apparatus 109, illustrating another construction for securing the elongate stiffening member 120 to the sheath 130. In this embodiment, the sheath 130 is formed into first and second separate lumens 130' and 130." The first lumen 130' is the primary lumen through which an instrument, such as an electrical pacing lead, passes. The elongate stiffening member 120 is received in the second lumen 130." The elongate stiffening member 120 may be bonded along its entire length or at intervals to an interior surface 130(a) of the second lumen 130." Alternatively, as is shown in FIG. 26, the elongate stiffening member 120 may be slidable within the second lumen 130." In the embodiment shown in FIG. 26, the sheath 130 having first and second lumens 130,' 130" is preferably formed by co-extruding a polymer material of the type described above.

FIG. 27 illustrates a cross-sectional view of the distal portion of the apparatus 109, illustrating still another construction for securing the elongate stiffening member 120 to the sheath 130. Similar to the embodiment discussed above and shown in FIG. 27, the sheath 130 is formed into first and second separate lumens 130' and 130." The first lumen 130' is the primary lumen through which an instrument, such as an electrical pacing lead, passes. The second lumen 130" contains the elongate stiffening member 120. The elongate stiffening member 120 may be bonded along its entire length or at intervals to an interior surface 130(a) of the second lumen 130." Alternatively, as is shown in FIG. 27, the elongate stiffening member 120 may be slidable within the second lumen 130." The first and second lumens 130', 130" of the sheath 130 are joined by a spine 130(b), which preferably runs along the entire length of the sheath 130. The first and second lumens 130', 130" are preferably formed by co-extruding a polymer material of the type described above. In an alternative configuration, the spine 130(b) may be formed from a bonding material that links or otherwise connects the first and second lumens 130', 130" of the flexible sheath 130.

Figure 28:
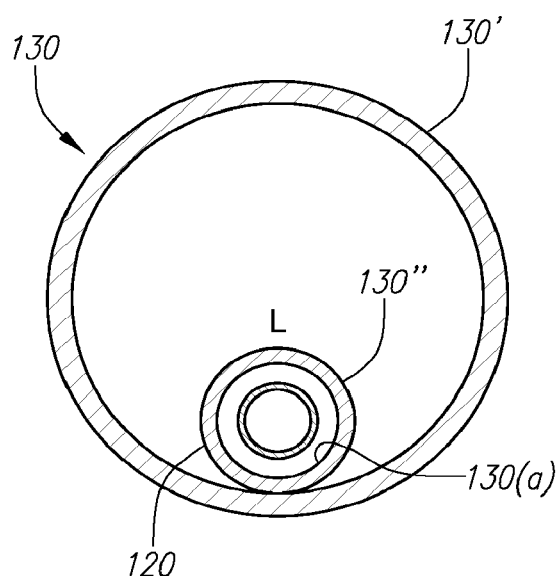

FIG. 28 shows a cross-sectional view of the distal portion of the apparatus 109, illustrating still another construction for securing the elongate stiffening member 120 to the sheath 130. In this embodiment, the second lumen 130" is located within the primary lumen 130' of the flexible sheath 130. The elongate stiffening member 120 is disposed within the second lumen 130" and may be bonded to an interior surface, or, alternatively, may be slidable therein. The advantage to the embodiment shown in FIG. 28 is that the profile of the apparatus 109 may be reduced, thereby making it easier to advance the apparatus 109 within particularly narrow passageways or vessels.

Figure 29:
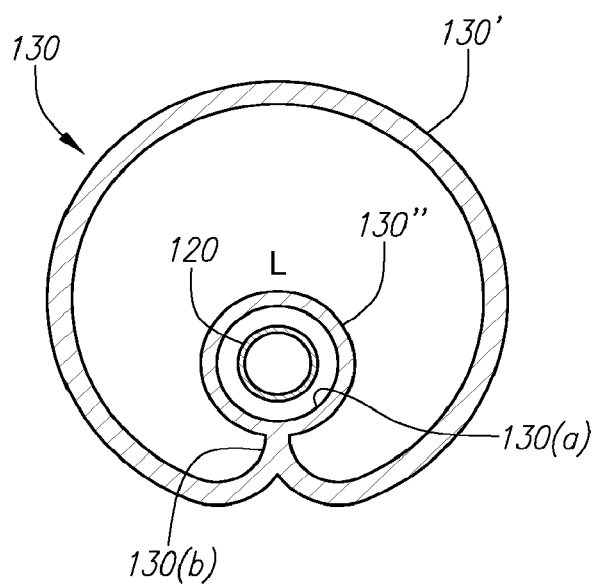

FIG. 29 illustrates yet another configuration of the distal end of the apparatus 109. In this embodiment, the structure shown in FIG. 27 may be inverted, thereby placing the second lumen 130" within the interior of the primary lumen 130' of the sheath 130. The inverting process may be accomplished by pulling an end of the sheath 130 shown in FIG. 27 through the primary lumen 130.' This embodiment is particularly advantageous for two reasons. First, the cross-sectional profile may be reduced by placing the second lumen 130" within the interior of the primary lumen 130.' Second, the spine 130(b) may serve as a barrier that prevents an instrument, such as an electrical pacing lead, from coiling or wrapping around the second lumen 130."

Figure 30A:
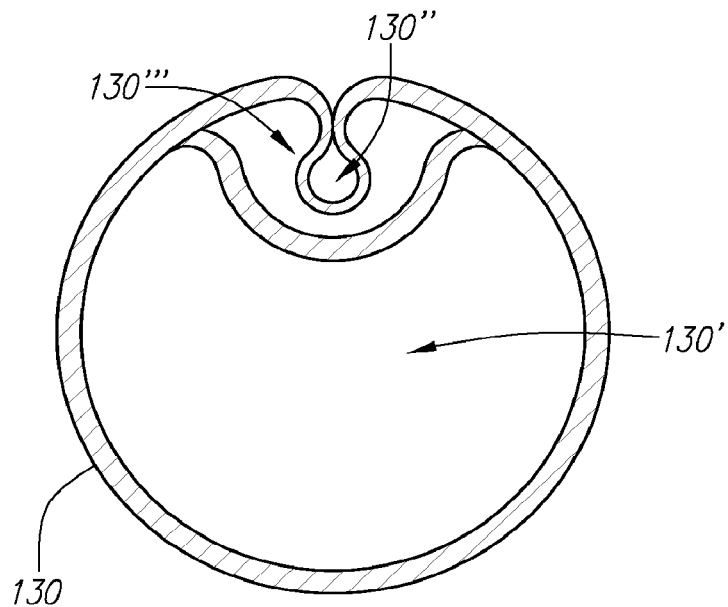
FIGS. 30A and 30B are cross-sectional views of additional alternative configurations of the sheath apparatus of FIGS. 24A and 24B.
Figure 30B:
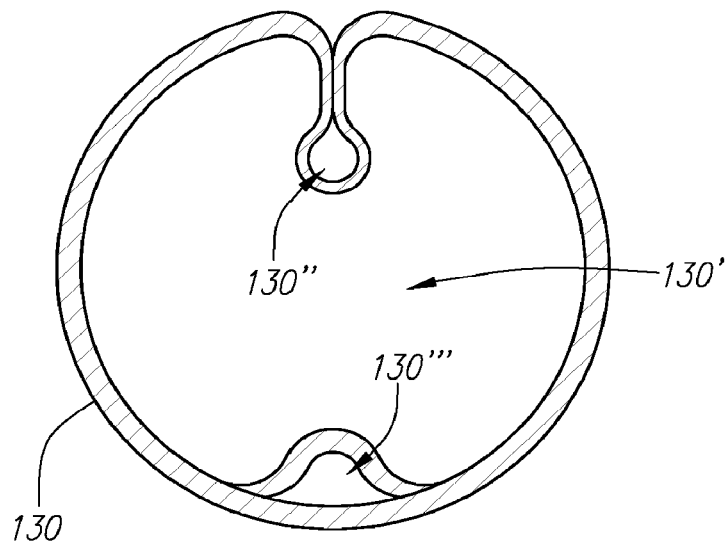

FIGS. 30A and 30B illustrate yet another configuration of the distal end of the apparatus 109. In this embodiment, the flexible sheath 130 forms first, second and third lumens 130,' 130," 130.'" The first or primary lumen 130' may be used to receive an instrument, such as an electrical pacing lead, and the like. The second lumen 130" may receive the elongate stiffening member 120 (not shown). The third lumen 130'" may be used, for example, to receive an instrument, such as a guidewire and the like. Alternatively, the third lumen 130''' may be used to receive or contain a contrast solution (not shown) for imaging the location of the apparatus 109 within a patient. The third lumen 130''' may enclose the second lumen 130," as is shown in FIG. 30A, or may be opposite the second lumen 130," shown in FIG. 30B.

FIGS. 31A, 31B, and 31C illustrate a method for constructing a flexible sheath 130 having first, second, and third lumens 130,' 130," and 130''' out of a cast film. With reference to FIG. 31A, a film 140 may be provided having a base layer 140(*a*) of PTFE and a surface layer of FEP 140(*b*). If a third lumen 130''' is desired, a separate layer of film 142 having a base layer 142(*a*) of PTFE and a surface layer of FEP 142(*b*) may be provided adjacent to film 140. The smaller layer of film 142 is oriented to place the two FEP surface layers 140(*b*), 142(*b*) in contact with one another. A space 143 or lumen may also be formed between the two layers of film 140, 142. The two layers of film 140, 142 may then be bonded to one another at the interfaces by, for example, heat bonding the two opposing FEP-FEP surfaces 140(*b*), 142(*b*).

After bonding the two opposing FEP-FEP surfaces 140(*b*), 142(*b*), the structure shown in FIG. 31B may be formed by folding the sheet 140 onto itself and heat bonding opposing FEP-FEP surfaces 140(*b*) at locations A and B as shown in FIG. 31B. In this regard, a sheath 130 may be formed having first, second, and third lumens 130,' 130," and 130.''' The first lumen 130' is preferably used to receive an instrument, such as an electrical pacing lead (not shown). The second lumen 130" is preferably used to house the elongate stiffening member 120. The third lumen 130''' is preferably used to receive or contain contrast solution for imaging the location of the apparatus 109.

FIG. 31C illustrates a sheath 130 created by inverting the structure shown in FIG. 31B. The sheath 130 may be created by pulling an end of the sheath 130 shown in FIG. 31B through the first or primary lumen 130.' This structure is particularly preferred because it places the lubricious PTFE layer 140(*a*) on the interior of the primary lumen 130.'

Figure 32:
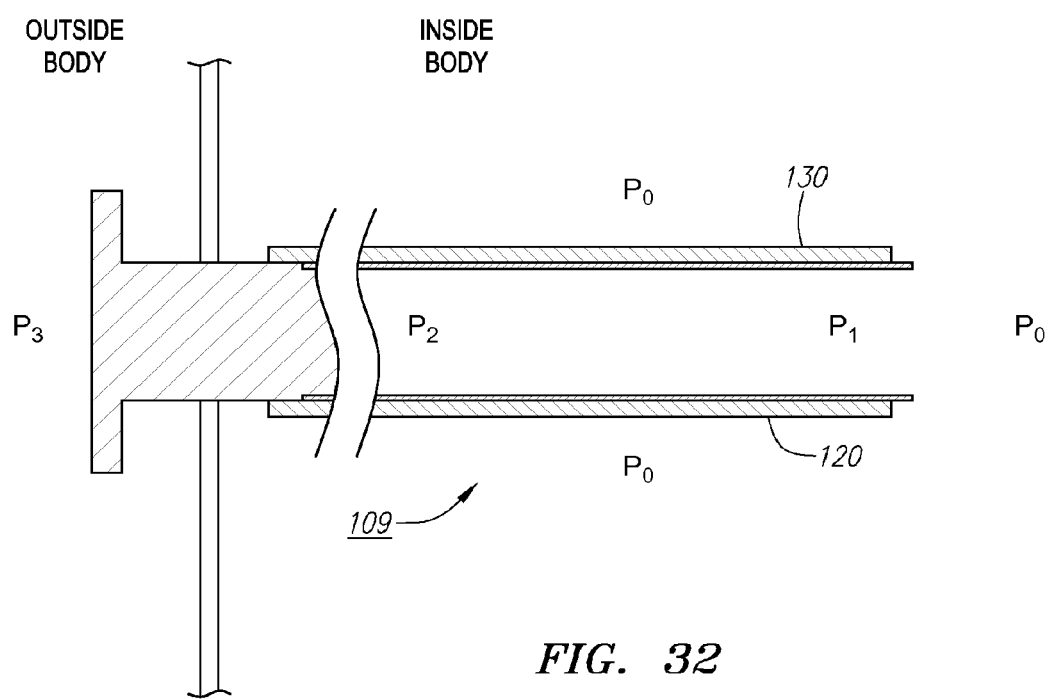
FIG. 32 is a cross-sectional side view of yet another embodiment of a flexible sheath providing an automatically sealing lumen.

FIG. 32 illustrates an auto-sealing nature of a flexible sheath 130, according to another embodiment. When placed inside a pressurized environment within the body (e.g., within a blood vessel), the flexible sheath 130 may collapse when the pressure differential between the outside of the sheath 130 and the inside of the sheath 130 is sufficient to overcome the "hoop" strength of the sheath 130.

FIG. 32 illustrates several different pressures experienced by the apparatus 109 100 located within a blood vessel. $P_0$ represents the blood pressure of the blood vessel. $P_1$ represents the pressure at the distal end of the sheath 130 while $P_2$ represents the pressure at a proximal region of the sheath 130. $P_3$ represents atmospheric pressure. Given that $P_1 > P_2 > P_3$ and at the distal tip of the sheath 130 $P_0 \approx P_1$, then the sheath 130 may collapse when the differential between P2 and $P_0$ is sufficient to overcome the resilient or "hoop" strength of the sheath 130.

In thin-walled materials with a low "hoop" strength, the collapse of the sheath 130 occurs readily. The collapse of the sheath 130 (either on itself or around another structure such as an elongate stiffening member 120) may prevent blood loss and/or further reinforce the pressure differential that keeps the sheath material in the collapsed configuration.

Figure 33:
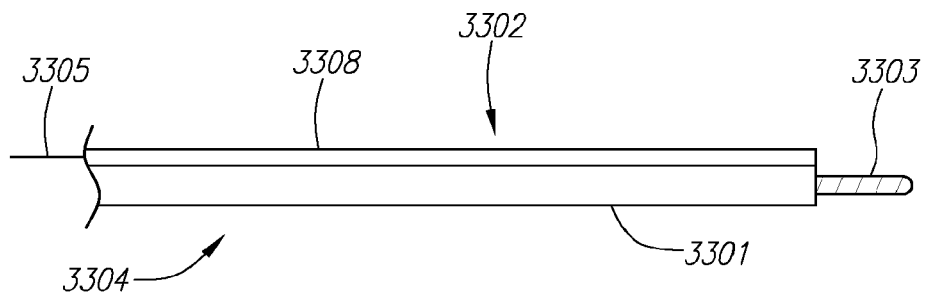
FIG. 33 is a side view of a steerable sleeve.

Turning to FIG. 33, illustrated is an elongate tubular flexible membrane sleeve 3301 having a peripherally attached steering element 3302. The sleeve 3301 may be made similar to any of the embodiments described elsewhere herein. The steering element 3302 may be made and/or secured to the sleeve 3301 similar to any of the embodiments described elsewhere herein. Optionally, any of the sleeves and/or steering elements described herein may have cross-sections and/or constructions similar to the devices described in applications Ser. No. 60/649,497 filed Feb. 3, 2005, 60/752,763 filed Dec. 20, 2005, Ser. No. 10/958,034 filed Oct. 4, 2004, Ser. No. 10/958,035 filed Oct. 4, 2004, Ser. No. 11/057,074 filed Feb. 11, 2005, and Ser. No. 11/062,074 filed Feb. 17, 2005, the entire disclosures of which are expressly incorporated by reference herein.

As shown in FIG. 33, the sleeve 3301 may be positioned over an elongate flexible device 3303, such as a guidewire, pacemaker lead, catheter, or sheath. The sleeve 3301 may be passively or actively attached to the device 3303. For example, the sleeve 3301 may be secured around the device 3303 by interference fit, e.g., friction between the outer surface of the device 3303 and the inner surface of the sleeve 3031. For example, the sleeve 3301 may be shrink-fit around the device 3303, e.g., using hot air. Alternatively, an interference fit may be accomplished using an inflatable internal lumen, e.g., as described elsewhere herein. In other alternative embodiments, the sleeve 3301 may be attached to the device 3303 using an adhesive, heat bonding, solvent bonding, and the like. Consequently, the sleeve 3301 may be permanently or removably attached to the device 3303.

In an exemplary embodiment, an apparatus 3304, including the sleeve 3301 and the steering element 3302 may be loaded over a standard device 3303 (such as a guidewire, pacing lead, catheter, and the like) immediately before or during a procedure to impart steerability to the device 3303. Alternatively, the apparatus 3304 may be loaded onto the device 3303 in advance, e.g., during manufacturing.

Figure 34:
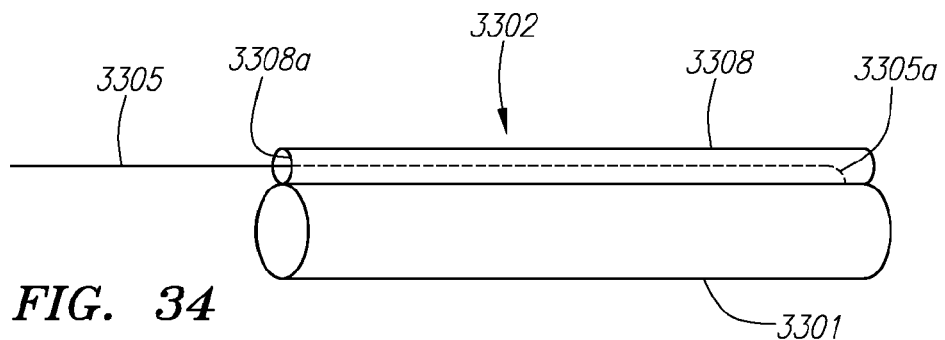
FIG. 34 is a perspective view of another embodiment of a steerable sleeve.

Turning to FIG. 34, the steering element 3302 may include an elongate tubular structure 3308 extending along at least a portion of the sleeve 3301 and a pull wire 3305 disposed within the tubular structure 3308. For example, the tubular structure 3308 may include a separate tubular member attached along the sleeve 3301 or may be integrally formed from the same material, e.g., using the methods and/or materials described elsewhere herein, thereby defining a lumen 3308*a*. The tubular structure 3308 may extend along an entire length of the sleeve 3301 or only along one or more desired portions, e.g., along a steerable distal portion. The pull wire 3305 may include a distal end 3305*a* attached or otherwise fixed relative to the sleeve 3301, but other may extend freely through the lumen 3308*a*, e.g., to a proximal end (not shown) of the sleeve 3301. Thus, when tension is applied, i.e., by pulling the pull wire 3305 from the proximal end, a bending moment may be applied to the sleeve 3301 (and consequently any device 3303 disposed within the sleeve 3301), causing the sleeve 3301 (and device 3303) to curve or otherwise bend adjacent the fixed distal end 3305*a* of the pull wire 3305.

In an alternative embodiment, the pull wire 3305 may be replaced with a shaped or shapeable stylet or wire, which may be inserted into the tubular structure 3308 to impart steerability. In a further alternative, the tubular structure 3308 may be omitted, and the pull wire 3305 may extend proximally along an outer surface of the sleeve 3301 from the fixed distal end 3305*a*. Optionally, in this alternative, one or more bands, receivers, or other elements (not shown) may be provided spaced apart along the sleeve 3301 to capture the pull wire 3305 and/or otherwise prevent the pull wire 3305 from twisting around the sleeve 3301 and/or separating from the sleeve 3301, while allowing the pull wire 3305 to be pulled from the proximal end of the sleeve 3301.

Figure 35:
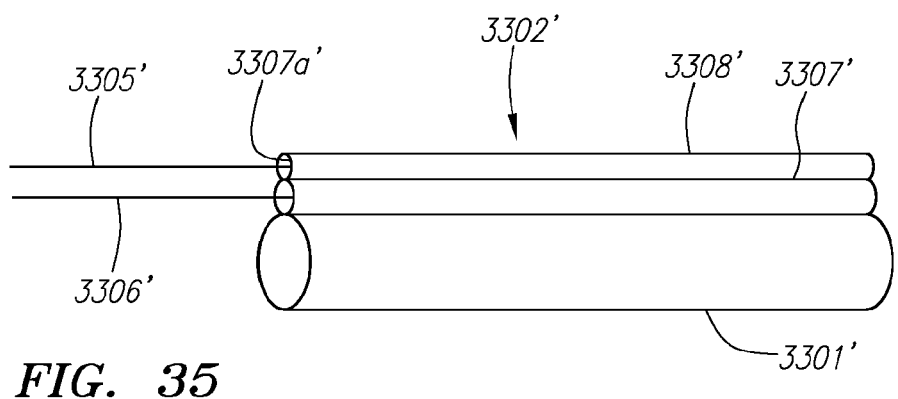
FIG. 35 is a perspective view of yet another embodiment of a steerable sleeve.

Turning to FIG. 35, in an alternative embodiment, another tubular structure 3307' may be provided along at least a portion of the sleeve 3301' for receiving a stiffening element

3306.' The tubular structure 3307' may be attached along an outer surface of the sleeve 3301' or may be integrally formed with the sleeve 3301' similar to the tubular structure 3308.' The stiffening element 3306' may be an elongate member within the tubular structure 3307' to modulate steering of the sleeve 3301' in a desired manner. For example, the stiffening element 3306' may be slidably disposed within a lumen 3307a' of the tubular structure 3307' to modulate steering as the stiffening element 3306' is moved within the tubular structure 3307.' Additional information on modulating steerability is disclosed in application Ser. No. 11/062,074, incorporated by reference above.

The tubular structures 3307' and 3308' may be disposed adjacent to one another around the periphery of the sleeve 3301' or aligned against one another such that one is disposed radially away from the sleeve 3301.' Alternatively, the stiffening element 3306' may be separated from the steering element 3302,' e.g., located opposite to the steering element 3302' or any other position on the sleeve 3301' (not shown). In further alternatives, there may be more than one steering element or stiffening element (not shown). While the steering element, stiffening element, and sleeve are shown as discrete lumens, the lumens may be formed such that they are segregated out of at least one or more major lumens (not shown).

Figure 36:
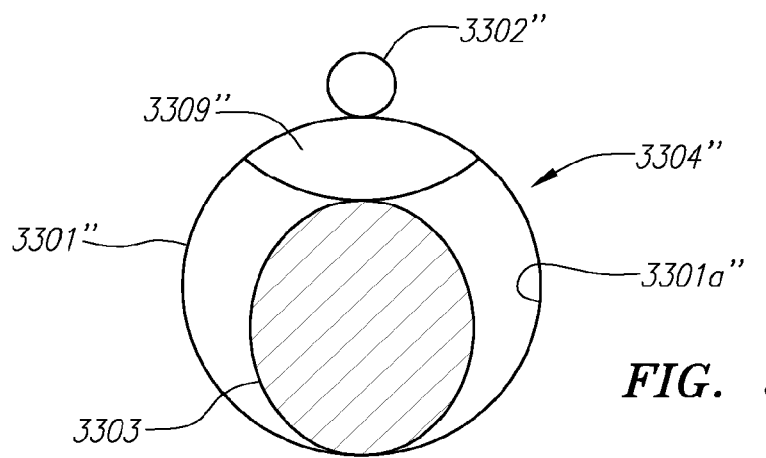
FIG. 36 is a cross-sectional view of yet another embodiment of a steerable sleeve.

Turning to FIG. 36, in yet another embodiment, an apparatus 3304" may include a tubular sleeve 3301" that includes a plurality of lumens therein, e.g., a device lumen 3301a" and a pressurization lumen 3309." As shown, the apparatus 3304" includes a steering element 3302," which may be similar to other embodiments herein, and/or may include a stiffening element (not shown). The pressurization lumen 3309" may extend along the sleeve 3301," e.g., along an interior of the sleeve 3301" from a proximal end to a steerable distal portion (not shown) of the sleeve 3301." The pressurization lumen 3309" may be created by attaching material to the sleeve 3301" or may be integrally formed with the sleeve 3301" similar to other embodiments described herein.

A distal end of the pressurization lumen 3309" is closed such that, when inflation media, e.g., saline or nitrogen, are introduced into the pressurization lumen 3309," the pressurization lumen 3309" may expand inwardly to engage a device 303 received in the device lumen 3301a." Thus, an interference or friction fit may be created between the sleeve 3301" and the device 3303, thereby securing the sleeve 3301" to the device 3303. Subsequently, if it is desired to remove the sleeve 3301," the pressurization lumen 3309" may be evacuated, allowing the sleeve 3301" to be removed, e.g., pulled from the proximal end (not shown) of the device 3303.

Figure 37:
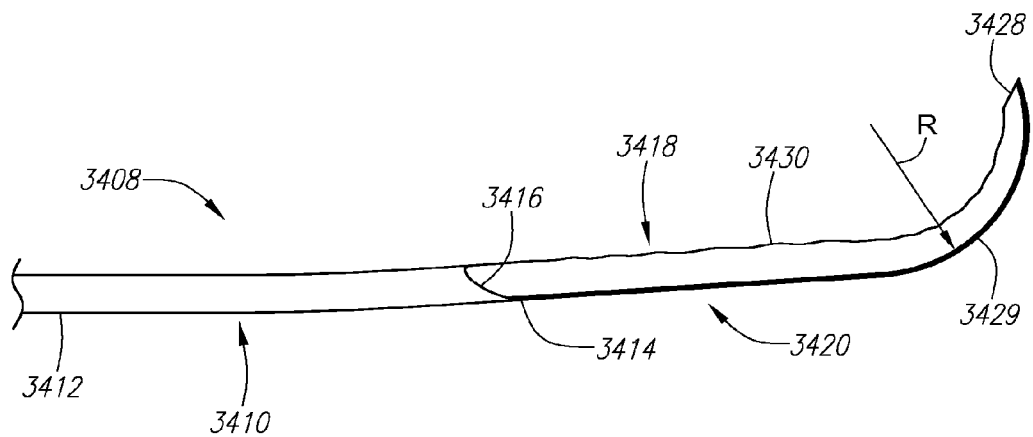
FIG. 37 is a side view of a flexible sheath with a shaped distal tip.
Figure 38:
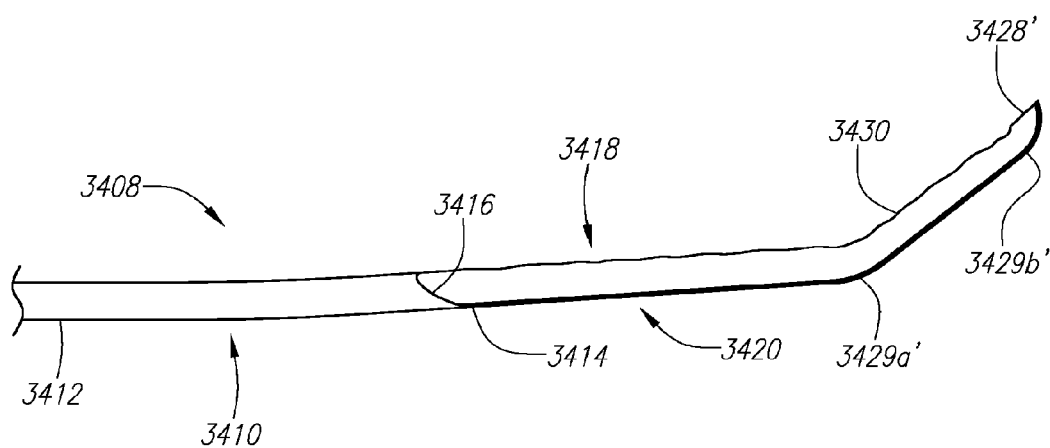
FIG. 38 is side view of another embodiment of a flexible sheath with a shaped distal tip.

Turning to FIGS. 37 and 38, an apparatus 3408 is shown that includes a tubular proximal portion 3410 and an expandable distal portion 3418. The tubular proximal portion 3410 is an elongate tubular member, e.g., a catheter, sheath, and the like, including a proximal end 3412, a distal end 3414 sized for insertion into a body lumen, and a lumen 3416 extending between the proximal and distal ends 3412, 3414.

With continued reference to FIGS. 37 and 38, the expandable distal portion 3418 generally includes an elongate stiffening member 3420 providing a "backbone" for the distal portion 3418 and an expandable sheath 3430. The elongate stiffening member 3420 has a proximal end and a distal tip 3428, which may terminate distal to, proximal to, or be approximately co-terminus with the distal expandable sheath 3430. Generally, the construction of the tubular proximal portion 3410 and the expandable distal portion 3418 is similar to other embodiments described herein.

Optionally, the distal tip 3428 of the stiffening member 3420 may be radiopaque, e.g., to enhance visibility of the distal tip 3428 under fluoroscopy. In addition or alternatively, the distal tip 3428 may be tapered and/or substantially flat, e.g., to facilitate trackability through a patient's anatomy. In a further option, the distal tip 3428 may be substantially flexible, e.g., to facilitate navigation and/or enhance atraumaticity. In yet another alternative, the distal tip 3428 may be substantially stiff, e.g., to enhance maintaining the distal tip 3428 in a desired position at a desired anatomical site.

Similar to the previous embodiments, the distal tip 3428 may be shaped and/or steerable to facilitate tracking or navigation within a body cavity or lumen. For example, as shown in FIG. 37, a distal portion 3429 of the stiffening member 3420 may be shape-set to a simple curve, e.g., including a radius "R" between about 0.5 and four inches (12.5-100 mm), and an arc between about twenty five and one hundred eighty degrees (25-180°).

Alternatively, as shown in FIG. 38, the distal tip 3428' may have multiple curvatures or bends in one or more planes. For example, the distal tip 3428' may have a first larger bend or curvature 3429a' and a second smaller bend or curvature 3429b.' The shape and/or size of these bends may be configured to facilitate navigation of or positioning within various body lumens or cavities. For example, the shapes may be optimized to facilitate cannulating the coronary sinus ostium within the right atrium (not shown) from either a superior or inferior approach. Alternatively, such shapes may be optimized for cannulation of tributaries within the coronary venous system, such as mid-cardiac, posterior, lateral, anterolateral or other suitable targets for placing pacemaking leads. In other alternatives, shapes may be selected that facilitate direct delivery of leads to right atrial, right ventricular, or other chambers of the heart. For example, in one embodiment, the shape may be optimized to direct the distal tip 3428' easily to the right ventricular septal wall for direct delivery of pacing leads to that location. In yet another embodiment, the distal tip 3428' may be shaped for ease of positioning in the right atrial appendage for delivery of pacing leads to that location.

Alternatively, or in addition to having a pre-shaped distal tip, the apparatus 3408 may have a steerable or deflectable distal tip (not shown). For example, the expandable sheath 3430 and/or stiffening member 3420 may include one or more steering elements, e.g., a pull wire, rotatable and/or translatable shaped stylet, or any other available means for steering or deflection. For example, similar to previous embodiments, a pull wire (not shown) may extend through a lumen or other tubular structure extending along the expandable sheath 3430. Alternatively, a pull wire (also not shown) may extend through a lumen in the stiffening member 3420. If the expandable sheath 3430 connects to a tubular member, e.g., a catheter or sheath (not shown), the pull wire may extend through a lumen in the tubular member to a proximal end of the apparatus. An actuator on a handle or other location on the proximal end may be coupled to the pull wire to actuate the pull wire, e.g., to cause the expandable sheath 3430 to curve or otherwise bend in a desired manner.

Optionally, the steering element may include one or more elements for providing variable steering, similar to those described elsewhere herein and/or in application Ser. No. 11/062,074, incorporated by reference above.

Figure 39:
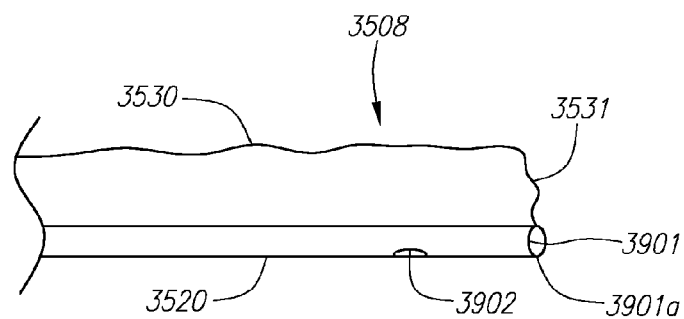
FIG. 39 is a perspective view of a distal tip of a flexible sheath adapted for tracking over a guidewire into a vessel.

Turning to FIG. 39, a distal portion of an apparatus 3408 is shown, which may be generally similar to the apparatus described above. Similar to the previous embodiments, an expandable sheath 3530 may be attached to an elongate stiffening member 3520. The stiffening member 3520 may be adapted to track directly into a vessel over a guidewire. For example the stiffening member may be back loaded onto a guidewire (not shown), e.g., by loading the guidewire into guidewire lumen 3901 through a distal opening 3901*a*.

The guidewire lumen 3901 may exit at the proximal end (not shown) of the apparatus 3508 or anywhere along the length of the apparatus 3508. For example, in a rapid-exchange configuration, the guidewire may exit through a proximal opening 3902 in the stiffening member 3520 disposed a predetermined distance from the distal opening 3901*a*.

The expandable sheath 3530 and its distal opening 3531 may be adapted, for example, by appropriate attachment, reinforcement, and/or lubricity (e.g., using a hydrophylic coating) to track into a dilated or undilated vessel puncture in conjunction with advancing the stiffening member 3520 into a vessel over a guidewire.

Turning to FIGS. 40A-40C, another embodiment of an apparatus 308 is shown that includes a tubular proximal portion 310, an expandable distal portion 318, and a stylet 370. The tubular proximal portion 310 is an elongate tubular member, e.g., a catheter, sheath, and the like, including a proximal end 312, e.g., with a handle 350, a distal end 314 sized for insertion into a body lumen, and one or more lumens 316 extending between the proximal and distal ends 312, 314.

The expandable distal portion 318 generally includes an elongate stiffening member, catheter, or "backbone" 320 and an expandable sheath 330. The stiffening member 320 includes a distal tip 328, which may terminate distal to, proximal to, or be approximately co-terminus with the expandable sheath 330. The distal tip 328 and/or other portions of the stiffening member 320 may be constructed of one or more polymeric materials, such as PEBAX, urethanes, polyethylenes, fluoro-polymers, polyesters, polyamides, polyimides, and the like. The expandable sheath 330 may be expandable from a contracted condition (not shown) to an expanded condition (e.g., as shown in FIG. 40A) defining a lumen communicating with the lumen 316 in the tubular member 310, e.g., to receive a pacing lead, electrode, fluid, and/or other similar medicaments and/or devices therethrough. Generally, the construction of the tubular proximal portion 310 and the expandable distal portion 318 may be similar to other embodiments described herein.

Similar to other embodiments described herein, the distal tip 328 may be shaped and/or steerable to facilitated tracking or navigation within a body cavity or lumen. For example, the distal tip 328 may be substantially flexible, e.g., relatively flexible compared to the stylet 370 such that the stylet 370 may be used to change the shape or otherwise manipulate the distal tip 328, as described further elsewhere herein. In addition or alternatively, the distal tip 328 and/or a distal portion 329 of the stiffening member 320 may be shape-set, i.e., may be biased to a predetermined nonlinear shape. For example, similar to the embodiments shown in FIGS. 37 and 38, the distal portion 329 may be shape-set to a simple curve, to multiple curvatures or bends in one or more planes, and the like. Alternatively, the distal tip 328 and/or distal portion 329 may be biased to a substantially straight orientation and/or may be "floppy," i.e., may have little radial and/or column strength.

The stylet 370 may be a substantially rigid, semi-rigid, or flexible elongate member that includes a proximal end 372, e.g., including a handle 373, a distal end 374 sized for insertion into the stiffening member 320, and a distal portion 376 including a nonlinear shape. As shown in FIGS. 40A and 40B, the stylet 370 may have sufficient length to be inserted into the stiffening member 320, e.g., into a side port 354 in the handle 350, through a lumen (not shown) in the tubular member 310, and into a lumen of the stiffening member 320. The stylet 370 may be formed from metal, such as stainless steel, Nitinol, and the like, plastic, or composite materials, e.g., similar to other embodiments described herein.

For example, in one embodiment, at least the distal portion 376 of the stylet 370 may be formed from malleable material, e.g., Nitinol, stainless steel, or other similar memory retaining materials, such that the stylet 370 may be manipulated into a desired shape and then remain biased to that shape. For example, at least the distal portion 376 of the stylet 370 may be bent, curved, or otherwise formed into a desired nonlinear shape while the stylet 370 is separate from the apparatus 308. The stylet 370 may then remember the shape while being advanced through the apparatus 308 and/or into the stiffening member 320, and/or while being delivered through a patient's vasculature and/or other tortuous anatomy, e.g., together with or separate from the apparatus 308. In addition or alternatively, the stylet 370 may include a pre-set shape, e.g., including one or more bends or other nonlinear shapes to which the stylet 370 is biased. The stylet 370 may be sufficiently flexible to allow the stylet 370 to conform to the shape of the apparatus 308 and/or surrounding anatomy, e.g., during delivery, but may be biased to the shape-set, e.g. upon being advanced into the distal tip 328 of the stiffening member 320 and/or otherwise deployed.

During use, the apparatus 308 may be introduced into a patient's vasculature or other body lumens during a procedure, e.g., to deliver a pacing lead, similar to other embodiments. The stylet 370 may be separate from the apparatus 308 during introduction or may be preloaded within the apparatus 308 proximal to at least the distal tip 328. If preloaded, the proximal portion of the stiffening member 320, e.g., proximal to the distal tip 328, may be sufficiently rigid to resist substantially adopting the shape of the stylet 370 or being affected by the shape-set of the stylet 370. Alternatively, the stylet 370 may be disposed within the tubular member 310 during delivery.

Once the stiffening member 320 is disposed within a first location, e.g., a vessel within a patient's coronary venous system, the stylet 370 may be inserted into the distal tip 328, thereby biasing the distal tip 328 towards a desired nonlinear shape. For example, the distal tip 328 of the stiffening member 320 may be sufficiently flexible to comply with the curvature of the stylet 376, e.g., such that the distal tip 328 may be biased to the shape-set of the stylet 376. Alternatively, the distal tip 328 may have a first shape-set, and the stylet 370 may have a second shape-set such that insertion of the stylet 370 causes the distal tip 328 to adopt a third shape based upon the combined geometries of the first and second shape-sets and/or the relative rigidities of the stylet 370 and the distal tip 328. Optionally, the stylet 370 may be rotated and/or directable axially within or otherwise relative to the distal tip 328, e.g., to change the shape and/or orientation of the distal tip 328 within a patient's vasculature or other body lumen.

In an alternative embodiment, the stylet 370 may not be removable entirely from the apparatus 308. For example, the handle 350 may include an actuator (not shown) to which the stylet 370 is coupled such that the stylet 370 is integrated with the tubular member 310 and/or stiffening member 320. For example, the actuator may limit movement of the stylet 370 between a proximal position, e.g., where the stylet 370 is removed from the distal tip 328, and a distal position, e.g., where the stylet 370 is inserted into the distal tip 328. Thus, during delivery, the stylet 370 may be maintained in the proximal position, but may be advanced to the distal position when desired using the actuator. Optionally, the stylet 370 may be movable to multiple preset distal positions, e.g., where the stylet 370 is moved relative to the distal tip 328 to modify a shape of the distal tip 328, or may be movable freely between the proximal and distal positions.

Optionally, as shown in FIG. 40D, the distal tip 328 and/or the stylet 370 may include one or more features to prevent the stylet 370 from being advanced beyond the distal tip 328. For example, as shown, the stylet 370 includes an enlarged tip, e.g., a round ball 378 or other feature that does not affect the shape of the stylet 370. In addition, the stiffening member 320 may include an internal ring 329 or other narrowing that may contact the ball 378 to prevent the stylet from being advanced beyond the distal tip. 328. Alternatively, the stylet 370 may be advanceable beyond the distal tip 328, if desired, e.g., including a rounded or otherwise substantially atraumatic tip (not shown).

Turning to FIG. 41, an exemplary method is shown for navigating through a first vessel or body lumen 95 into a side branch or second vessel or body lumen 95, e.g., using the apparatus 308 shown in FIGS. 40A-40C. As described above, the stylet 370 may have a shape-set distal portion 376, which may facilitate navigating vessels by acting as a directional guide to the stiffening member 320. The stiffening member 320 and stylet 370 may be advanced together to position the apparatus 308, e.g., with the stylet 370 advanced at least partially into the stiffening member 320, the stylet 370 enhancing column strength and/or torquability of the expandable distal portion 318. For example, when cannulating tortuous anatomy and/or complex geometries, the stylet 370 may help to overcome friction between the expandable distal portion 318 and surrounding anatomy during advancement. In addition, the stiffening member 320 with the stylet 370 therein may reduce and/or eliminate the need for a guidewire (not shown), which may otherwise be needed to access to deep recesses in the branch 96, e.g., in order to maintain a stable position. Alternatively, if the stiffening member 320 has sufficient column strength, the stylet 370 may be positioned within the proximal tubular portion 310 and/or may be withdrawn entirely from the apparatus 308.

FIGS. 42A and 42B show further details of a method for navigating a vessel 95 using an apparatus 308 including a stylet 370 with a shape-set distal portion 376, e.g., to navigate into a side-branch 96 extending from the vessel 95. The apparatus 308 may be introduced into the vessel 95, e.g., with the stylet 370 retracted from the distal tip 328. Once the distal tip 328 is positioned adjacent the branch, the stylet 370 may be inserted into the distal tip 328, thereby causing the distal tip 328 to bend, as shown in FIG. 42A.

The apparatus 308 may be manipulated to direct the distal tip 328 with the stylet 370 therein into the branch 96. For example, with the stylet 370 within the distal tip 328, the distal tip 328 may become biased to adopting an acute bend, as shown in FIG. 42A. The apparatus 308 may then be manipulated axially and/rotated to direct the bent distal tip 328 into the branch 96. If desired, the stylet 370 may be manipulated further, e.g., to change the shape of the distal tip 328 while manipulating the apparatus 308, e.g., to facilitate accessing the branch 96. Alternatively, the apparatus 308 may be manipulated before advancing the stylet 370, and the stylet 370 may be advanced and withdrawn repeatedly until the stylet 370 automatically directs the distal tip 328 into the branch 96. Optionally, the distal tip 328 and/or the distal portion 376 of the stylet 370 may include one or more radiopaque markers for monitoring the orientation and location of the distal tip 328, e.g., using fluoroscopy or other external imaging, to facilitate in positioning and cannulating the branch 96.

Once the stylet 370 and distal tip 328 have been positioned in the branch 96, the apparatus 308 may be advanced further into the branch 96 over the stylet 370. For example, the position of the stylet 370 may be maintained, e.g., by placing tension on the stylet 370 and/or otherwise holding the stylet 370 substantially stationary, while advancing the apparatus 308 distally over the stylet 376, as shown in FIG. 42B. Thus, the shape-set of the stylet 370 may be sufficiently rigid to cause the stiffening member 320 and/or other portion of the apparatus 308 to navigate the curvature of the branch 96, e.g., without substantial risk of the stiffening member 320 prolapsing. The stylet 376 may simply enter the ostium of the branch 96 or, alternatively, may contact a wall of the branch 96, e.g., to prevent undesired movement of the stylet 370 relative to the branch 96, which may stabilize the apparatus 308 during advancement into the branch 96. Optionally, once the expandable distal portion 318 of the apparatus 308 is advanced sufficiently into the branch 96, the stylet 370 may be removed from the distal tip 328 and/or stiffening member 320 and/or entirely from the apparatus 308 (if removable).

Turning to FIGS. 43A and 43B, an expandable distal portion of a catheter or other apparatus 308 is shown, which may be similar to the embodiment of FIG. 40A or any other embodiment described herein. As shown in FIG. 43A, a stylet 370 has been inserted into a distal tip 328 of a stiffening member 3220, thereby causing the distal tip 3218 to assume a nonlinear shape, e.g., a simple bend as shown. As shown in FIG. 43B, as the stylet 370 is removed from the distal tip 328 (and/or the apparatus 308 is advanced relative to the stylet 370), the shape of the distal tip 328 may change, e.g., becoming less curved or bent. For example, if the distal tip 328 also includes a shape-set, various curvatures and/or geometries may be attained by positioning the stylet 10 within the stiffening member 320, which may cause the distal tip 328 to curve and/or deflect for navigating branches and/or other pathways within a patient's vasculature.

Optionally, additional curvatures and/or shapes may be achieved by rotating the shape-set stylet 370 relative to the distal tip 328, and/or by a combination of relative rotation and/or advancement/retraction between the shape-set stylet 370 and the stiffening member 320. In addition or alternatively, the distal tip 328 may have a shape memory and/or may be malleable such that the distal tip 328 becomes biased towards a shape created when the stylet 370 is advanced into the distal tip 328. Thereafter, as the stylet 370 is retracted, the angle of the distal tip 328 may be maintained, as created by the shape-set of the stylet 370, e.g., as shown in FIGS. 45A and 45B.

Turning to FIGS. 44A-44D, various tips are shown that may be provided on a catheter, sheath apparatus, and the like, such as those described elsewhere herein. FIG. 44A shows a tapered tip 342 that inherently has multiple regions 342a, 342b, and 342c of varying stiffness, i.e., due to the varying thickness of the sidewall. Alternatively, FIG. 44B-44D show a distal tip 342' that include three regions 344, 346, 348 that have different properties from one another. For example, the three regions may be formed from three different materials or may be the same material but having different durometers. Each of the materials may have a different stiffness profile such that, when combined with a stylet 370 including a shape-set distal portion 376, the curvature and/or deflection of the distal tip 342' may vary. For example, in the embodiment shown in FIGS. 44B-44D, the first region 344 may have a lower stiffness profile than the second region 346, and the second region 346 may, in turn, have a lower stiffness profile than the third region 348. With the distal portion 376 of the stylet 50 positioned in the first region 44, as shown in FIG. 44B, the distal tip 342' may be biased to assume an acute angle, which may be useful for traversing a tight angle in a side branch. When the distal portion 376 of the stylet 370 is positioned in the second region 346, as shown in FIG. 44C (having a stiffer profile), the distal tip 342' may be biased to assume a bend including a slightly wider, more oblique angle. When the distal portion 376 of the stylet 370 is positioned in the third region 348 (having an even higher stiffness profile), the distal tip 342' may be biased to form another angle that is wider still, as shown in FIG. 44D. Each of these profiles may allow a clinician to optimize the curvature and/or geometry of the distal tip 342' as required for each particular anatomy encountered within a patient's vasculature. An actuator (not shown) may include set positions corresponding to the positions shown in FIGS. 44B-44D, or the actuator may allow the stylet 370 to be moved freely between the positions, e.g., while the user monitors the distal tip 342' to observe the shape assumed in any particular position of the stylet 370.

In addition and/or alternatively, a shape-set and/or varying stiffness distal tip in combination with a shape-set stylet may be combined to provide any desired degree of deflection and/or curvature in the embodiments described herein or in other catheter devices. For example, such shapes may be used for cannulating coronary vein tributaries within the coronary venous system, such as mid-cardiac, posterior, lateral, anterolateral, or other suitable target locations, e.g., for placing pacing leads. Optionally, other alternative shapes may be selected that may facilitate direct delivery of leads to the right atrial, right ventricular, or other chambers of the heart.

Optionally, in addition to having a shape-set tip and/or stylet, the embodiments described herein may include other components, materials, and/or constructions, such as those described elsewhere herein. The steerable and/or shapeable features described herein may be included in other catheters or tubular devices, e.g., not including an expandable sheath, if desired. In addition or alternatively, the embodiments described herein may be formed using methods of construction for slitting and/or peeling, e.g., with ripcords and/or tabs, such as those disclosed in U.S. application Ser. No. 11/563,142, filed Nov. 24, 2006, the entire disclosure of which is expressly incorporated by reference herein.

Turning to FIGS. 46A and 46B, an exemplary embodiment of a catheter 410 is shown that generally includes a proximal end (not shown), a distal end 414 sized and/or shaped for introduction into a patient's body, and a shape-set distal tip 428. The catheter 410 may include one or more lumens, e.g., lumen 416 for receiving a guidewire 470 or other elongate member therein. Optionally, the catheter 410 may include an expandable sheath (not shown), similar to other devices described herein. The catheter 410 may be constructed using any of the materials and/or methods described elsewhere herein.

Turning to FIGS. 47A and 47B, another embodiment of a catheter 510 is shown schematically that includes a proximal end with a handle 550, a distal end 514 with a shape-set distal tip 528, and an integrated stylet 570 with an actuator 554 on the handle 550. In this embodiment, the stylet 470 does not have a shape-set tip, e.g., may be biased to a substantially straight configuration, while the distal tip 528 is biased to a nonlinear shape, e.g., a simple curve approaching one hundred eighty degrees, as shown in FIG. 47A. As shown in FIG. 47B, as the stylet 570 is advanced, the curvature and/or deflection of the shape-set distal tip 528 may conform to a combination shape created by the interfacing of the non-shape-set stylet 570 and the shape-set distal tip 528 of the catheter 510. In one embodiment, the stiffness of the stylet 570 may be sufficient to completely overcome any shape-set of the distal tip 528, e.g., to substantially straighten the distal tip 528 when the stylet 570 is fully advanced. Alternatively, the relative stiffnesses may be such that the stylet 570 is curved slightly when advanced, thereby reducing the angle of the curve of the distal tip 528. In addition or alternatively, the non-shape-set stylet 570 may be removable, e.g., after positioning the catheter 510 within a targeted body cavity and/or body lumen, and a guidewire or other rail (not shown) may be advanced through the catheter 510, e.g., beyond the distal tip 528 to facilitate delivering one or more medical devices, e.g., pacing leads, electrodes, implantable fluid delivery catheters, and the like.

FIG. 48 shows a catheter 410, e.g., similar to that shown in FIGS. 46A and 46B, including a shape-set tip 428 and having a shape-set stylet 470' being inserted into the catheter 410. The shape-set stylet 470' may be either integrated with a handle (not shown) and/or may remain removable, as described further elsewhere herein. Various curvatures and/or geometries for the distal tip 428a-428d may be attained, e.g., by relative rotation of the shape-set stylet 470' within the distal tip 428, or by a combination of relative rotation and relative advancement/retraction between the stylet 470' and the distal tip 428. Although not shown, it will be appreciated that the distal tip 428 may adopt a nonlinear shape that extends out of the plane of the drawing, as the stylet 470' and/or distal tip 428 are rotated.

Turning to FIG. 49, another embodiment of a catheter 610 including a shape-set tip 628 is shown that includes an integrated stylet 670, which may or may not have a shape-set, and a guidewire 680. As previously disclosed, various curvatures and geometries may be achieved while retaining the ability to independently advance, rotate, and/or retract the guidewire 680, e.g., to facilitate cannulation and/or access to other venous side branches or tributaries.

Referring to FIGS. 50A and 50B, in accordance with another embodiment, a catheter 710 including non-shape-set distal tip 728 may be combined with a shape-set stylet 770 (which may and/or may not be integrated). The stylet 770 that may be rotated and/or advanced and retracted to form various curvatures and/or deflections, e.g., as previously described to facilitate access and/or navigation through body cavities and/or lumens. Optionally, the rotation, advancement, and/or retraction of the shape-set stylet 770 may also promote various geometries that are in various planes of deflection allowing further access and/or navigation of tortuous anatomical features in coronary venous tributaries and/or body cavities and/or lumens.

Turning to FIG. 51, a catheter 710' including a non-shape-set distal tip 728' is shown including a variable stiffness profile where one part 728a' of the distal tip 728' has more stiffness while a second part 728b' of the distal tip 728' has less stiffness. The catheter 710' may be combined with a shape-set stylet 770, as described above. Moreover, multiple stiffness transitions (not shown) may be incorporated into the distal tip 728' to achieve a more continuous stiffness transition. As disclosed previously, various deflections and/or geometries may be facilitated by advancing the stylet 770 partly into the variable stiffness distal tip 728' (as in A) and/or further advancement (as in B) wherein numerous bends and/or deflections may be promoted as previously disclosed. More particularly, the various stiffness profiles may be facilitated by combinations of materials, such as PEBAX, HDPE, Nitinol or other metals, PET, polyamides, polyimides, and the like. In addition, doping of materials, e.g., with glass, silicon, and the like may also contribute to varying the stiffness profile.

Figure 52:
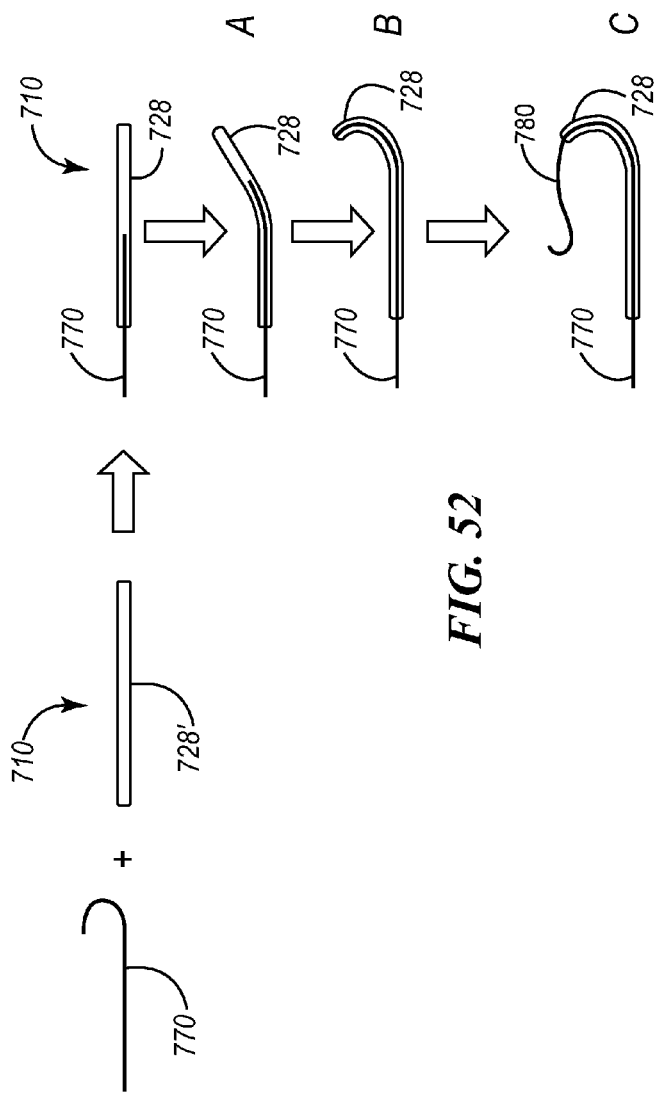
FIG. 52 shows yet another embodiment of a distal portion of a catheter, showing a stylet being advanced therein.

In FIG. 52, a further embodiment of a catheter 710 is shown that includes non-shape-set tip 728 (that may and/or may not have a varying stiffness profile), and a shape-set stylet 770.

The catheter 710 may include a guidewire lumen (not shown) for receiving a guidewire 780. The stylet 770 may be advanced to different positions, e.g., partially advanced as in A, advanced further as in B, and advanced completely as in C. The guidewire 780 may be advanced to enhance access to tortuous anatomical features while remaining independent of the stylet 770. The combination of non-shape-set distal tip 728 with a shape-set stylet 770 and guidewire 780 may form numerous bends and/or deflections, which may facilitate access and/or navigation into body cavities and/or lumens.

Figure 53:
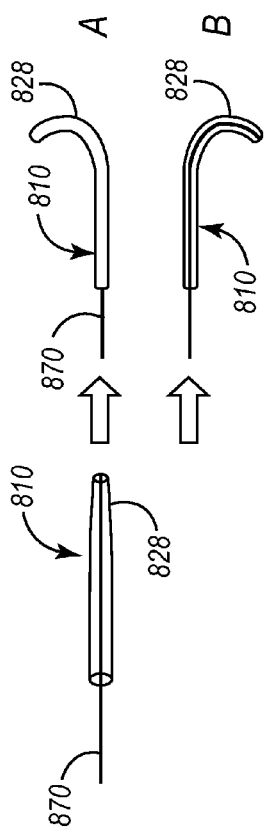
FIG. 53 shows still another embodiment of a distal portion of a catheter, showing a stylet being rotated therein.

Referring to FIG. 53, a catheter 810 is shown that includes a steerable distal tip 828 and a tension and compression member 870. The distal tip 828 may be selectively steerable using the tension and compression member 870. In compression, the distal tip 828 deflects away from the compression member (as shown in A), while, alternatively, in tension, the distal tip 828 deflects towards the tensile member (as shown in B). Optionally, the steerable tip 828 may also include a guidewire (not shown) and/or a variable stiffness profile, which may enhance the various curvatures and/or deflections, facilitated by the tensile and compression member 870.

It will be appreciated that elements or components shown with any embodiment herein are exemplary for the specific embodiment and may be used on or in combination with other embodiments disclosed herein.

While the invention is susceptible to various modifications, and alternative forms, specific examples thereof have been shown in the drawings and are herein described in detail. It should be understood, however, that the invention is not to be limited to the particular forms or methods disclosed, but to the contrary, the invention is to cover all modifications, equivalents and alternatives falling within the spirit and scope of the appended claims.

We claim:

1. An apparatus for providing access to a body lumen, comprising:

a tubular member extending from a proximal end thereof to a distal end thereof, the distal end being tapered and sized for insertion into the body lumen, and the tubular member defining a lumen that extends from the proximal end to the distal end;

an elongate stiffening member extending distally, from the distal end of the tubular member to a flexible distal terminal tip of the elongate stiffening member, the elongate stiffening member being fixedly attached to the tubular member and defining another lumen that extends into the flexible distal terminal tip;

an expandable sheath including a proximal end and a distal terminal end, the proximal end being fixedly attached directly to the distal end of the tubular member such that the proximal end of the sheath surrounds and overlies the distal end of the tubular member, the sheath extending distally from the distal end of the tubular member, over a length that is less than an overall length of the tubular member, and along at least a portion of the elongate stiffening member, the sheath being expandable from a contracted condition, to minimize a profile of the sheath to allow insertion along with the elongate stiffening member into a body lumen, to an enlarged condition, at which enlarged condition the sheath defines a lumen, the sheath lumen communicating with the tubular member lumen and including a distal opening, the distal opening terminating the sheath lumen and being defined by a portion of a perimeter of the distal terminal end of the sheath that becomes spaced apart from the elongate stiffening member, when the expandable sheath is expanded, and the distal opening allowing passage, therethrough, of a medical instrument into the body lumen, the medical instrument having been passed through the tubular member lumen and through the sheath lumen, alongside the elongate stiffening member; and a stylet insertable into, and removable from the elongate stiffening member lumen for changing a shape of the flexible distal terminal tip.

2. The apparatus of claim 1, wherein the proximal end of the tubular member includes a handle, the handle including a side port for inserting the stylet into, and removing the stylet from, the elongate stiffening member lumen.

3. The apparatus of claim 1, wherein at least a distal portion of the stylet is malleable such that the stylet is shapeable by a user before insertion into the elongate stiffening member lumen.

4. The apparatus of claim 1, wherein the flexible distal terminal tip of the elongate stiffening member is biased to assume a first nonlinear shape, and, when the stylet is inserted into the flexible distal terminal tip, the first nonlinear shape changes.

5. The apparatus of claim 4, wherein a distal portion of the stylet is biased to assume a second nonlinear shape, and the first nonlinear shape of the flexible distal terminal tip changes to the second nonlinear shape, when the stylet is inserted into the flexible distal terminal tip.

6. The apparatus of claim 4, wherein a distal portion of the stylet is biased to assume a second nonlinear shape, and the first nonlinear shape of the flexible distal terminal tip changes to a third nonlinear shape, when the stylet is inserted into the flexible distal terminal tip, the third nonlinear shape being based on the first and second nonlinear shapes.

7. The apparatus of claim 4, wherein a distal portion of the stylet is biased to assume a second nonlinear shape, the second nonlinear shape comprising an acute angle, and the first nonlinear shape of the flexible distal terminal tip changes according to the second nonlinear shape.

8. The apparatus of claim 1, wherein the flexible distal terminal tip of the elongate stiffening member includes a feature to prevent the stylet from extending beyond the flexible distal terminal tip of the elongate member, when the stylet is inserted into the elongate member lumen.

9. The apparatus of claim 1, further comprising an actuator on the tubular member proximal end for moving the stylet between a proximal position and a distal position, the stylet being disposed within the flexible distal terminal tip of the elongate member in the distal position and removed from the distal tip in the proximal position.

10. The apparatus of claim 1, wherein the tubular member has a length sufficient to reach at least one of the vena cava, right atrium, and coronary sinus of a patient's heart from a percutaneous entry location.

11. The apparatus of claim 1, wherein the elongate stiffening member extends beyond the distal end of the tubular member not more than about thirty centimeters (30 cm).

12. The apparatus of claim 1, wherein the elongate stiffening member extends beyond the distal end of the tubular member not more than about ten centimeters (10 cm).

13. The apparatus of claim 1, wherein the expandable sheath comprises a lubricious material.

* * * * *